United States Patent
Suzuki et al.

(10) Patent No.: US 10,741,769 B2
(45) Date of Patent: Aug. 11, 2020

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hiroki Suzuki, Kanagawa (JP); Satoshi Seo, Kanagawa (JP); Tatsuyoshi Takahashi, Kanagawa (JP); Hiromitsu Kido, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 210 days.

(21) Appl. No.: 15/730,065

(22) Filed: Oct. 11, 2017

(65) Prior Publication Data
US 2018/0108847 A1 Apr. 19, 2018

(30) Foreign Application Priority Data

Oct. 14, 2016 (JP) .................................. 2016-202251

(51) Int. Cl.
*H01L 51/50* (2006.01)
*H01L 51/00* (2006.01)
(Continued)

(52) U.S. Cl.
CPC ........ *H01L 51/0067* (2013.01); *C07D 405/10* (2013.01); *C07D 409/10* (2013.01);
(Continued)

(58) Field of Classification Search
None
See application file for complete search history.

(56) References Cited

U.S. PATENT DOCUMENTS 6,602,618 B2 * 8/2003 Watanabe ........... H01L 51/0081
313/504
7,906,226 B2 3/2011 Matsuura et al.
(Continued)

FOREIGN PATENT DOCUMENTS

JP 2010-182699 A 8/2010
JP 2016-019002 A 2/2016
(Continued)

*Primary Examiner* — Gregory D Clark
(74) *Attorney, Agent, or Firm* — Husch Blackwell LLP

(57) ABSTRACT

A novel organic compound is provided. That is, a novel organic compound that is effective in improving the element characteristics and reliability is provided. An organic compound has a benzonaphthofuran skeleton and a triazine skeleton and is represented by General Formula (G1) below.

(Continued)

(In the formula, $Ar^1$, $Ar^2$, and $Ar^3$ separately represent a substituted or unsubstituted phenylene group, and each of m and n is independently 0 or 1. $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $B^1$ to $B^3$ separately represent nitrogen or carbon, and at least one of $B^1$ to $B^3$ represents nitrogen. In addition, A is represented by General Formula (G1-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S or O.)

12 Claims, 31 Drawing Sheets

(51) Int. Cl.
| | |
|---|---|
| *C07D 405/10* | (2006.01) |
| *C07D 409/10* | (2006.01) |
| *H01L 51/52* | (2006.01) |
| *H01L 27/32* | (2006.01) |

(52) U.S. Cl.
CPC ...... *H01L 51/0072* (2013.01); *H01L 51/0073* (2013.01); *H01L 51/0074* (2013.01); *H01L 51/5036* (2013.01); *H01L 51/5218* (2013.01); *H01L 51/5237* (2013.01); H01L 27/3244 (2013.01); H01L 51/006 (2013.01); H01L 51/0052 (2013.01); H01L 51/0061 (2013.01); H01L 51/0085 (2013.01); H01L 51/5016 (2013.01)

(56) References Cited

U.S. PATENT DOCUMENTS

| | | |
|---|---|---|
| 8,652,654 B2 | 2/2014 | Inoue et al. |
| 2005/0225236 A1 | 10/2005 | Nomura et al. |
| 2006/0124924 A1* | 6/2006 | Suh ............ H01L 51/002 257/40 |
| 2007/0194692 A1 | 8/2007 | Nomura et al. |
| 2012/0274201 A1 | 11/2012 | Seo et al. |
| 2012/0277427 A1 | 11/2012 | Inoue et al. |
| 2013/0165653 A1 | 6/2013 | Inoue et al. |
| 2015/0031900 A1 | 1/2015 | Kawakami et al. |
| 2015/0060813 A1 | 3/2015 | Kawakami et al. |
| 2015/0318495 A1 | 11/2015 | Kawakami et al. |
| 2015/0329514 A1 | 11/2015 | Kawakami et al. |
| 2016/0028021 A1 | 1/2016 | Zeng et al. |
| 2016/0079314 A1 | 3/2016 | Seo et al. |
| 2016/0308139 A1 | 10/2016 | Seo et al. |
| 2016/0336519 A1 | 11/2016 | Seo et al. |
| 2017/0222156 A1 | 8/2017 | Kawakami et al. |
| 2017/0229648 A1 | 8/2017 | Kawakami et al. |
| 2017/0288154 A1 | 10/2017 | Seo et al. |
| 2018/0076394 A1 | 3/2018 | Kawakami et al. |
| 2019/0055222 A1* | 2/2019 | Han ............ C07D 235/06 |

FOREIGN PATENT DOCUMENTS

| | | | | |
|---|---|---|---|---|
| KR | 10-2015-0141236 | * | 10/2015 | ............ C09K 11/06 |
| KR | 10-2016-0041822 | * | 4/2016 | ............ C09K 11/06 |
| WO | WO 2011/132683 A1 | | 10/2011 | |

* cited by examiner

FIG. 4A
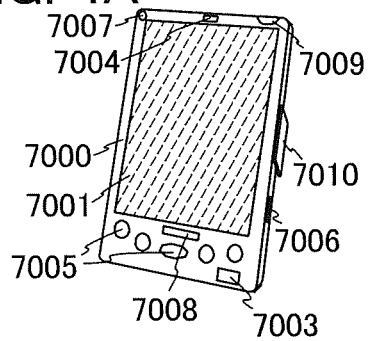
FIG. 4B
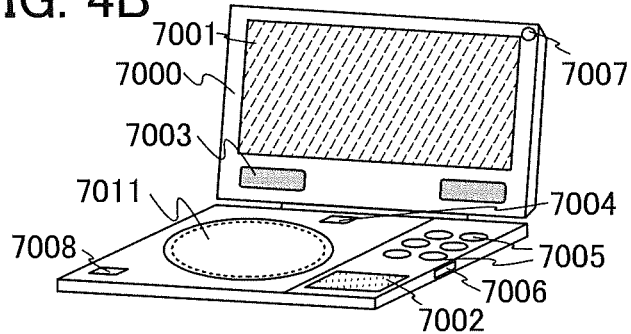
FIG. 4C
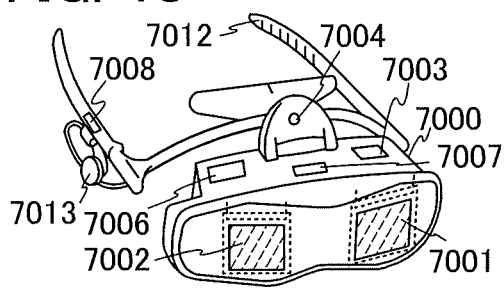
FIG. 4D
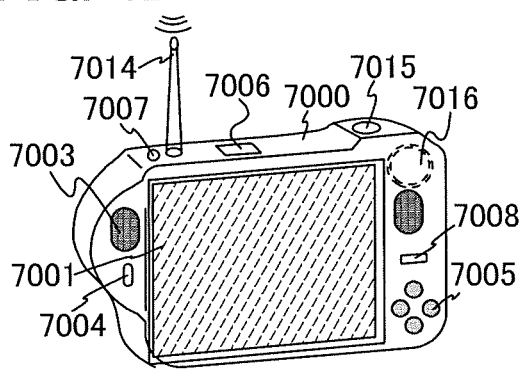
FIG. 4E
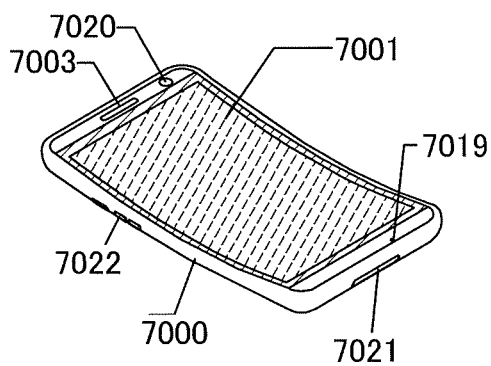
FIG. 4F
FIG. 4G
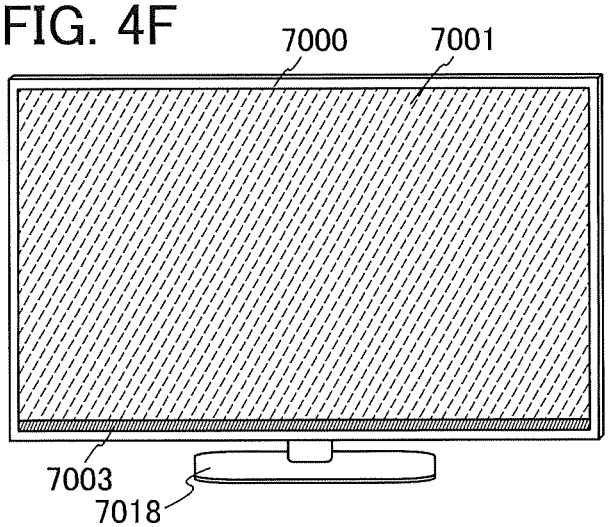

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organic compound, a light-emitting element, a light-emitting device, an electronic device, and a lighting device. Note that one embodiment of the present invention is not limited thereto. That is, one embodiment of the present invention relates to an object, a method, a manufacturing method, or a driving method. One embodiment of the present invention relates to a process, a machine, manufacture, or a composition of matter. Specific examples include a semiconductor device, a display device, a liquid crystal display device, and the like.

2. Description of the Related Art

A light-emitting element including an electroluminescent (EL) layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T'). Light emission from a singlet excited state is referred to as fluorescence, and light emission from a triplet excited state is referred to as phosphorescence. The statistical generation ratio thereof in the light-emitting element is considered to be S*:T*=1:3. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

[Patent Document 1] Japanese Published Patent Application No. 2010-182699

SUMMARY OF THE INVENTION

In development of light-emitting elements, organic compounds used in the light-emitting element are very important for improving the characteristics and reliability. Thus, an object of one embodiment of the present invention is to provide a novel organic compound. That is, an object is to provide a novel organic compound that is effective in improving the element characteristics and reliability. Another object of one embodiment of the present invention is to provide a novel organic compound that can be used in a light-emitting element. Another object of one embodiment of the present invention is to provide a novel organic compound that can be used in an EL layer of a light-emitting element. Another object is to provide a highly efficient, highly reliable, and novel light-emitting element using a novel organic compound of one embodiment of the present invention. Another object is to provide a novel light-emitting device, a novel electronic device, or a novel lighting device. Note that the description of these objects does not disturb the existence of other objects. In one embodiment of the present invention, there is not necessarily a need to achieve all the objects. Other objects will be apparent from and can be derived from the description of the specification, the drawings, the claims, and the like.

One embodiment of the present invention is an organic compound represented by General Formula (G1) below.

[Chemical Formula 1]

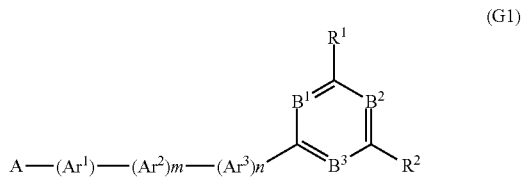

(G1)

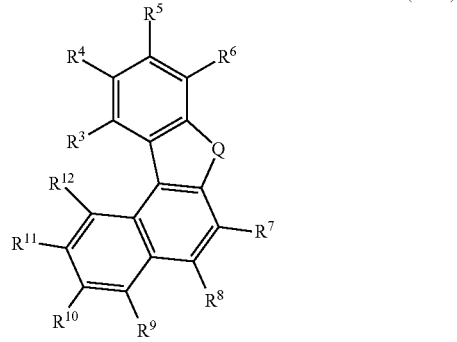

(G1-1)

In General Formula (G1), $Ar^1$, $Ar^2$, and $Ar^3$ separately represent a substituted or unsubstituted phenylene group, and each of m and n is independently 0 or 1. $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $B^1$ to $B^3$ separately represent nitrogen or carbon, and at least one of $B^1$ to $B^3$ represents nitrogen. In addition, A is represented by General Formula (G1-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S or O.

Another embodiment of the present invention is an organic compound represented by General Formula (G2) below.

[Chemical Formula 2]

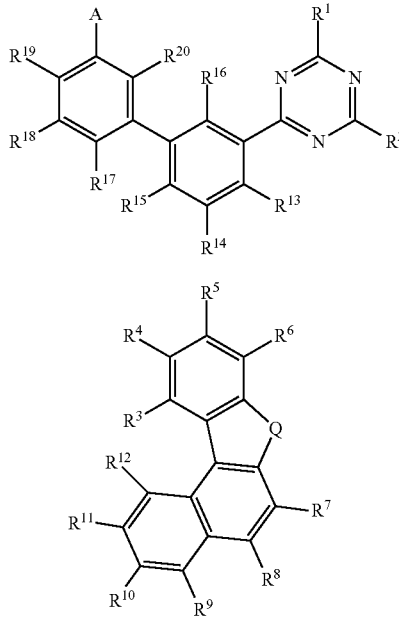

(G2)

(G2-1)

In General Formula (G2), $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $R^{13}$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, A is represented by General Formula (G2-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S or O.

Another embodiment of the present invention is an organic compound represented by General Formula (G3) below.

[Chemical Formula 3]

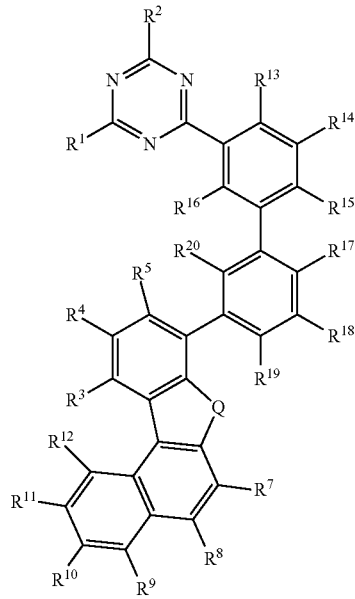

(G3)

In General Formula (G3), $R^1$, $R^2$, $R^3$ to $R^5$, and $R^7$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

Another embodiment of the present invention is an organic compound represented by General Formula (G4) below.

[Chemical Formula 4]

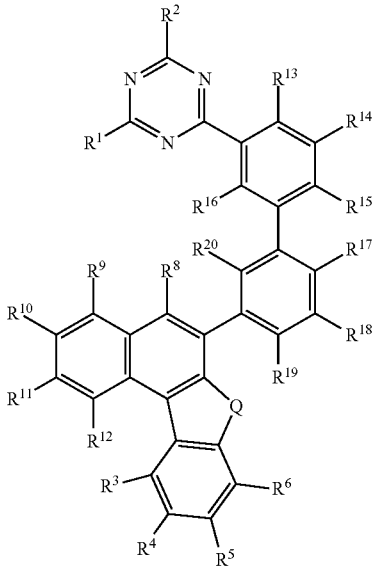

(G4)

In General Formula (G4), $R^1$, $R^2$, $R^3$ to $R^6$, and $R^8$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

Another embodiment of the present invention is an organic compound represented by General Formula (G5) below.

[Chemical Formula 5]

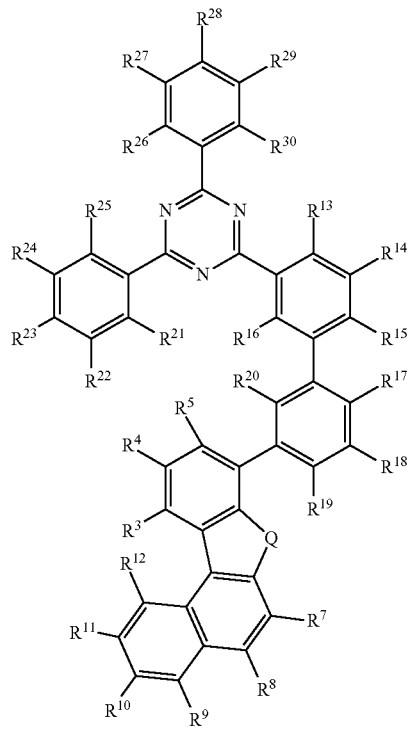

(G5)

In General Formula (G5), $R^3$ to $R^5$ and $R^7$ to $R^{30}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

Another embodiment of the present invention is an organic compound represented by General Formula (G6) below.

[Chemical Formula 6]

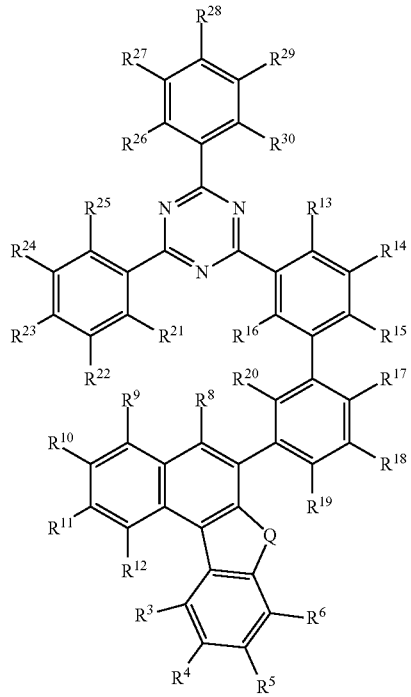

(G6)

In General Formula (G6), $R^3$ to $R^6$ and $R^8$ to $R^{30}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

The organic compound of each of the above embodiments of the present invention has a benzonaphthofuran structure or a benzonaphthothiophene structure. In the structure, dibenzofuran or dibenzothiophene, in which two benzene rings are fused to a heteroaromatic ring, is further fused. The organic compound having such a fused benzonaphthofuran structure or benzonaphthothiophene structure can improve reliability. In addition, by bonding a substituent to a benzene skeleton fused to a furan skeleton or a thiophene skeleton in a benzonaphthofuran structure or a benzonaphthothiophene structure, extension of conjugation can be suppressed, and broadening of spin density distribution at T1 (triplet excitation level) can be suppressed. This enables high reliability without lowering T1.

Another embodiment of the present invention is an organic compound represented by Structural Formula (100) or Structural Formula (121).

[Chemical Formula 7]

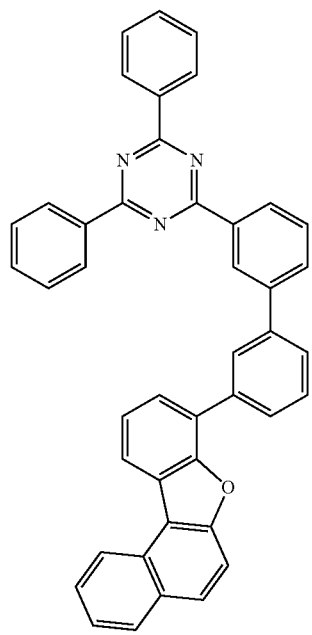

(100)

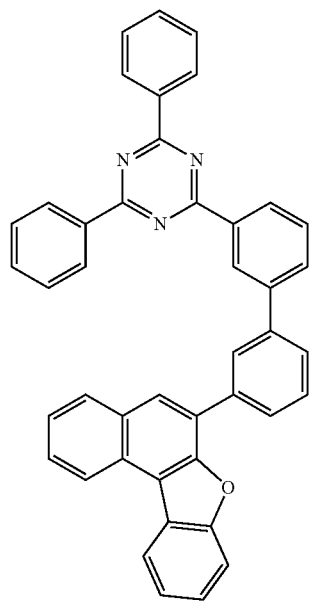

(121)

Another embodiment of the present invention is a light-emitting element containing an organic compound having a benzonaphthofuran skeleton and a triazine skeleton. The present invention also includes a light-emitting element containing the above organic compound and a substance that converts triplet excitation energy into light emission, such as a phosphorescent material including an organometallic complex or a thermally activated delayed fluorescence (TADF) material.

Another embodiment of the present invention is a light-emitting element containing the organic compound of one embodiment of the present invention. Note that the present invention also includes a light-emitting element in which an EL layer provided between a pair of electrodes or a light-emitting layer included in the EL layer contains the organic compound of one embodiment of the present invention. In addition to the above light-emitting elements, a light-emitting device including a transistor, a substrate, or the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

The organic compound of one embodiment of the present invention can be used as a light-emitting substance. Alternatively, the organic compound of one embodiment of the present invention can be used in combination with a light-emitting substance that emits phosphorescence (phosphorescent compound) for a light-emitting layer of a light-emitting element. That is, light emission from a triplet excited state can be obtained from the light-emitting layer; thus, the efficiency of the light-emitting element can be improved, which is very effective. Accordingly, one embodiment of the present invention also includes a light-emitting element in which the organic compound of one embodiment of the present invention and a phosphorescent compound are used in combination in a light-emitting layer. A structure in which the light-emitting layer further contains a third substance may also be employed.

One embodiment of the present invention includes, in its scope, a light-emitting device including a light-emitting element, and a lighting device including the light-emitting device. Accordingly, the light-emitting device in this specification refers to an image display device and a light source (including a lighting device). In addition, the light-emitting device includes, in its category, all of a module in which a connector such as a flexible printed circuit (FPC) or a tape carrier package (TCP) is connected to a light-emitting device, a module in which a printed wiring board is provided at the end of a TCP, and a module in which an integrated circuit (IC) is directly mounted on a light-emitting element by a chip on glass (COG) method.

According to one embodiment of the present invention, a novel organic compound can be provided. In other words, a novel organic compound that is effective in improving the element characteristics and reliability can be provided. According to one embodiment of the present invention, a novel organic compound that can be used in a light-emitting element can be provided. According to one embodiment of the present invention, a novel organic compound that can be used in an EL layer of a light-emitting element can be provided. According to one embodiment of the present invention, a highly efficient, highly reliable, and novel light-emitting element using a novel organic compound of one embodiment of the present invention can be provided. In addition, a novel light-emitting device, a novel electronic device, or a novel lighting device can be provided. Note that the description of these effects does not disturb the existence of other effects. In one embodiment of the present invention, there is not necessarily a need to achieve all the effects. Other effects will be apparent from and can be derived from the description of the specification, the drawings, the claims, and the like.

BRIEF DESCRIPTION OF THE DRAWINGS

FIGS. 4A to 4G illustrate electronic devices.

FIGS. 14A, 14B1, and 14B2 illustrate block diagrams of display devices.

DETAILED DESCRIPTION OF THE INVENTION

Figure 1A:
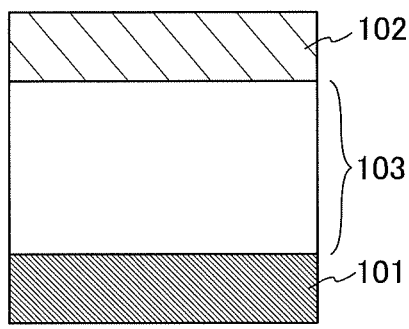
FIGS. 1A to 1D illustrate structures of light-emitting elements.

Embodiments of the present invention will be described below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In the description of modes of the present invention with reference to the drawings in this specification and the like, the same components in different diagrams are commonly denoted by the same reference numeral.

Embodiment 1

In this embodiment, organic compounds each of which is one embodiment of the present invention are described.

The organic compound of one embodiment of the present invention has a benzonaphthofuran skeleton and a triazine skeleton and has a structure represented by General Formula (G1) below.

[Chemical Formula 8]

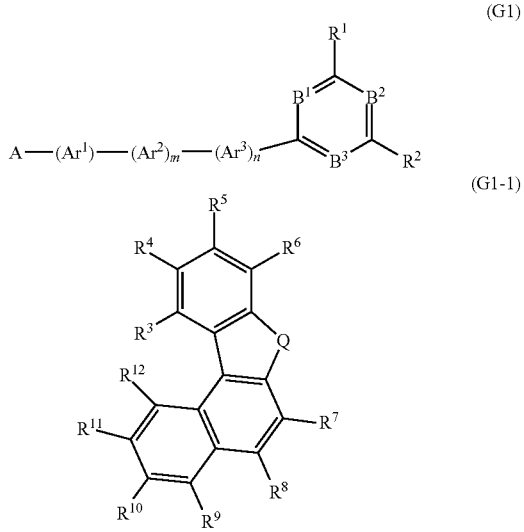

In General Formula (G1), $Ar^1$, $Ar^2$, and $Ar^3$ separately represent a substituted or unsubstituted phenylene group, and each of m and n is independently 0 or 1. $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $B^1$ to $B^3$ separately represent nitrogen or carbon, and at least one of $B^1$ to $B^3$ represents nitrogen. In addition, A is represented by General Formula (G1-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S or O.

An organic compound described in this embodiment is represented by General Formula (G2) below.

[Chemical Formula 9]

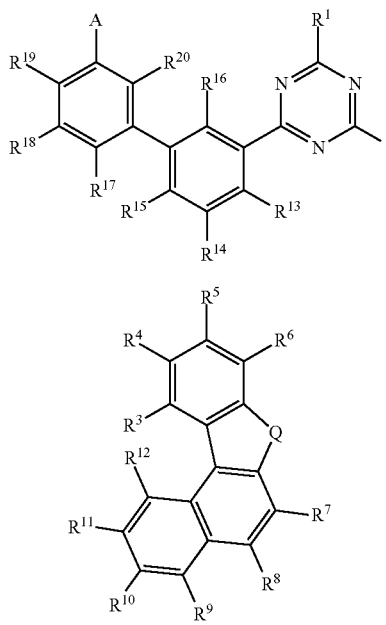

(G2)

(G2-1)

In General Formula (G2), $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $R^{13}$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, A is represented by General Formula (G2-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S or O.

An organic compound described in this embodiment is represented by General Formula (G3) below.

[Chemical Formula 10]

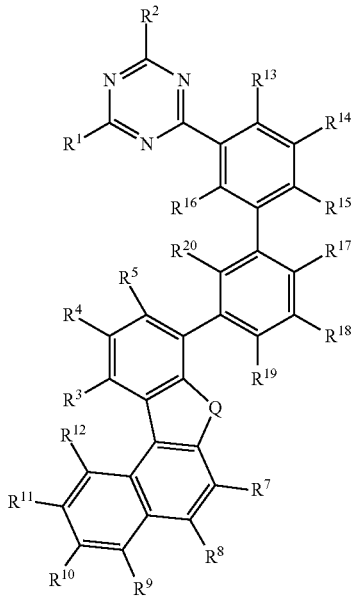

(G3)

In General Formula (G3), $R^1$, $R^2$, $R^3$ to $R^5$, and $R^7$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

An organic compound described in this embodiment is represented by General Formula (G4) below.

[Chemical Formula 11]

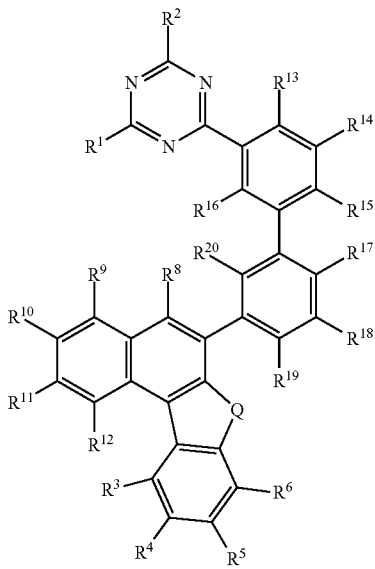

(G4)

In General Formula (G4), $R^1$, $R^2$, $R^3$ to $R^6$, and $R^8$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

An organic compound described in this embodiment is represented by General Formula (G5) below.

[Chemical Formula 12]

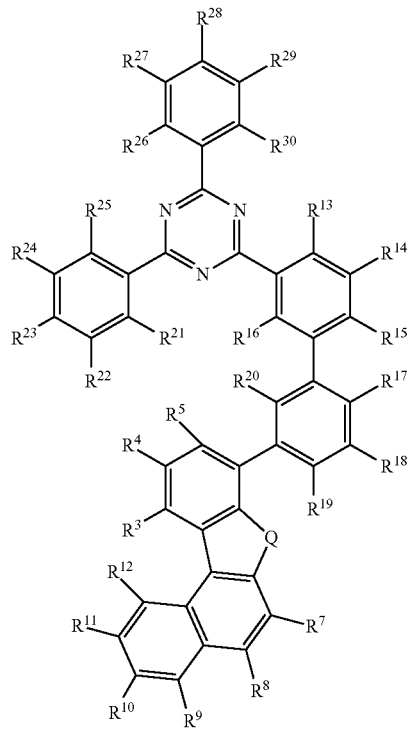

(G5)

In General Formula (G5), $R^3$ to $R^5$ and $R^7$ to $R^{30}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

An organic compound described in this embodiment is represented by General Formula (G6) below.

[Chemical Formula 13]

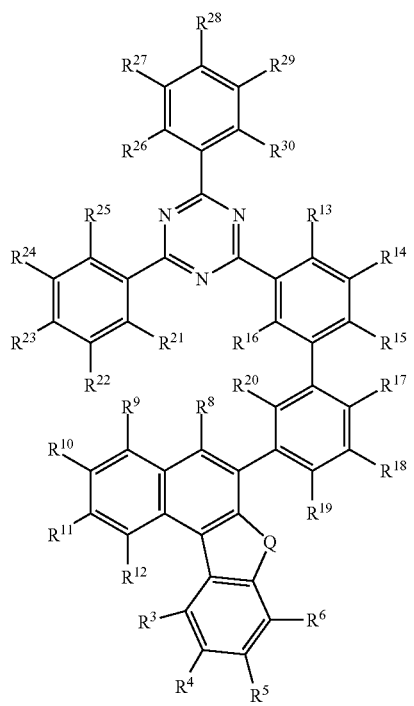

(G6)

In General Formula (G6), $R^3$ to $R^6$ and $R^8$ to $R^{30}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. In addition, Q represents S or O.

In any of General Formulae (G1) to (G6), when any of the substituted or unsubstituted phenyl group, the substituted or unsubstituted biphenyl group, the substituted or unsubstituted terphenyl group, the substituted or unsubstituted fluorenyl group, the substituted or unsubstituted methylfluorenyl group, the substituted or unsubstituted dimethylfluorenyl group, the substituted or unsubstituted spirofluorenyl group, the substituted or unsubstituted naphthyl group, or the substituted or unsubstituted phenanthrenyl group has a substituent, examples of the substituent include an alkyl group having 1 to 6 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, a 1-norbornyl group, or a 2-norbornyl group; and an aryl group having 6 to 12 carbon atoms, such as a phenyl group or a biphenyl group. These substituents may be bonded to each other to form a ring.

Specific examples of the alkyl group having 1 to 6 carbon atoms which is represented by any of $R^1$ to $R^{30}$ in General Formulae (G1) to (G6) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and the like.

The organic compound of one embodiment of the present invention which is represented by any of General Formulae (G1) to (G6) has a benzonaphthofuran structure or a benzonaphthothiophene structure. In the structure, dibenzofuran or dibenzothiophene, in which two benzene rings are fused to a heteroaromatic ring, is further fused. The organic compound having such a fused benzonaphthofuran structure or benzonaphthothiophene structure can improve reliability. In addition, by bonding a substituent to a benzene skeleton fused to a furan skeleton or a thiophene skeleton in a benzonaphthofuran structure or a benzonaphthothiophene structure, extension of conjugation can be suppressed, and broadening of spin density distribution at T1 (triplet excitation level) can be suppressed. This enables high reliability without lowering T1.

Next, specific structural formulae of the above-described organic compounds, each of which is one embodiment of the present invention, are shown below. Note that the present invention is not limited to these formulae.

[Chemical Formula 14]

(100)
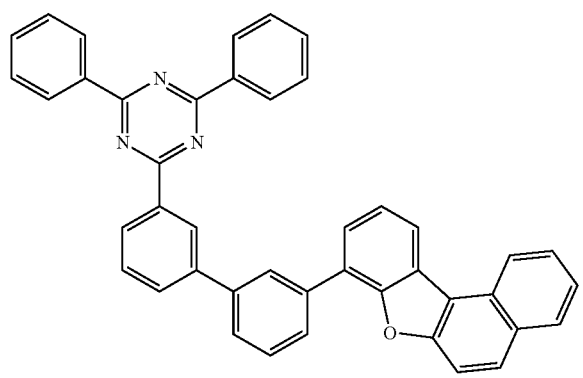

(101)
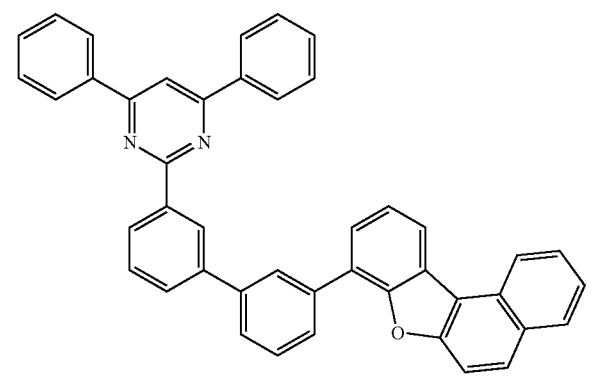

(102)
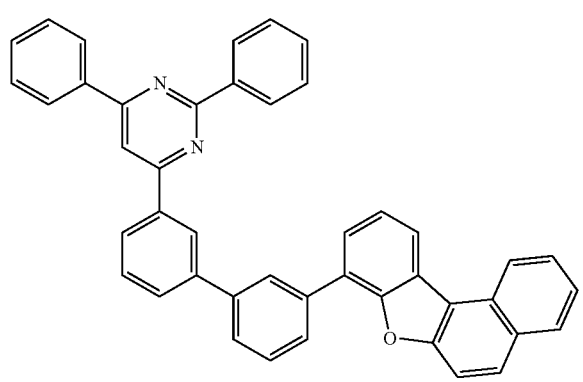

(103)
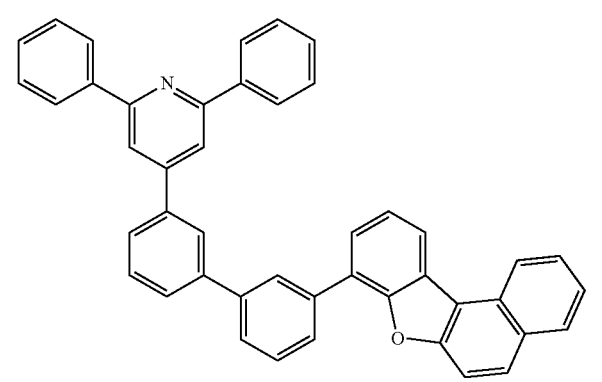

(104)
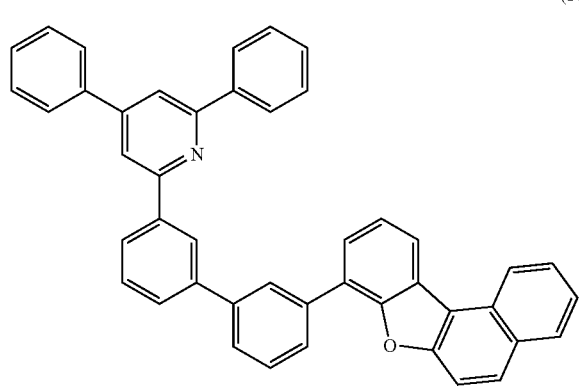

(105)
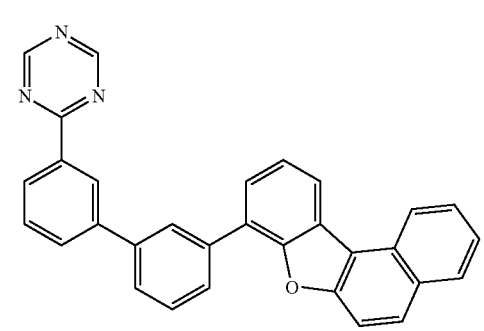

-continued
(106)
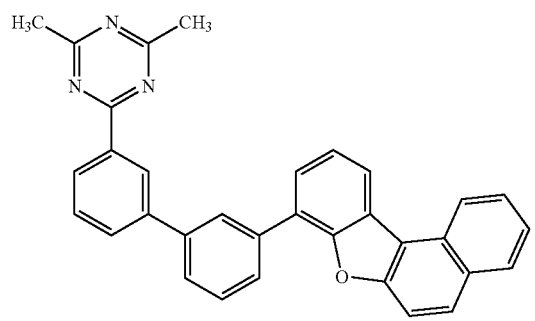
(107)
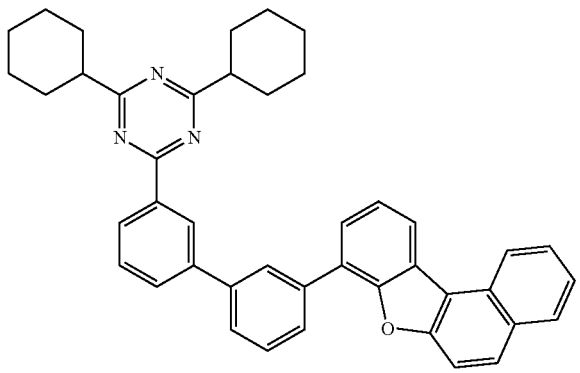
(108)
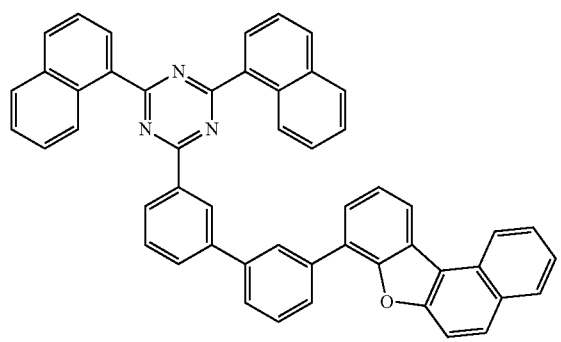
(109)
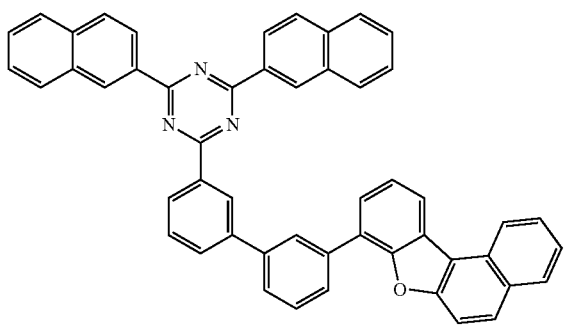
(110)
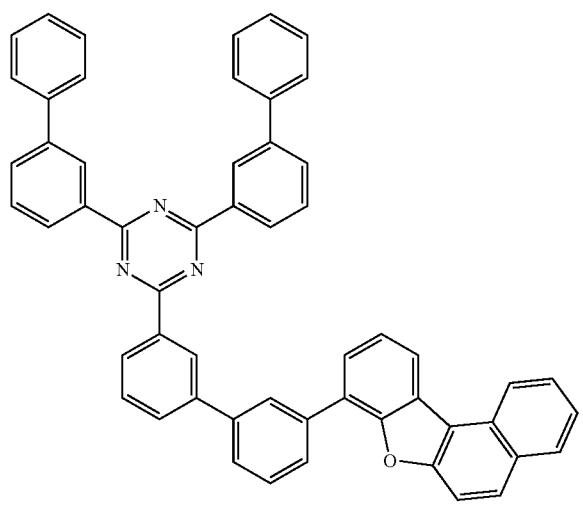

[Chemical Formula 15]
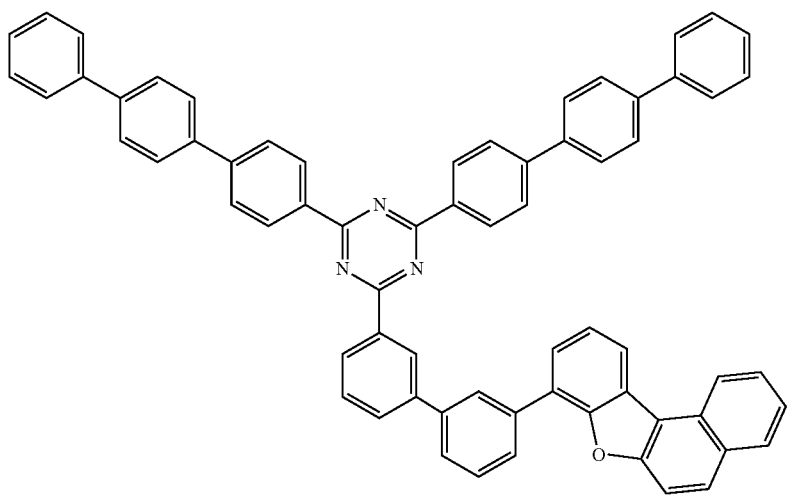
(111)
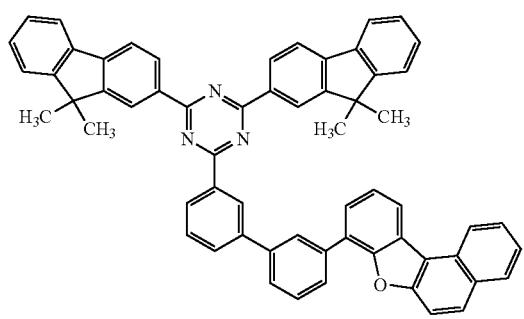
(112)
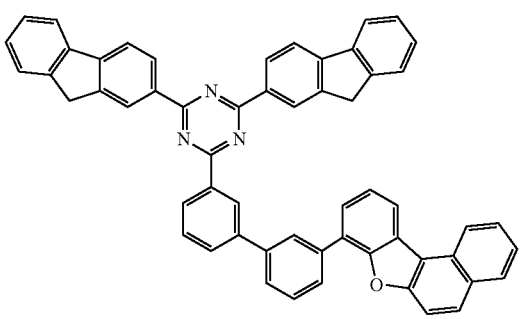
(113)
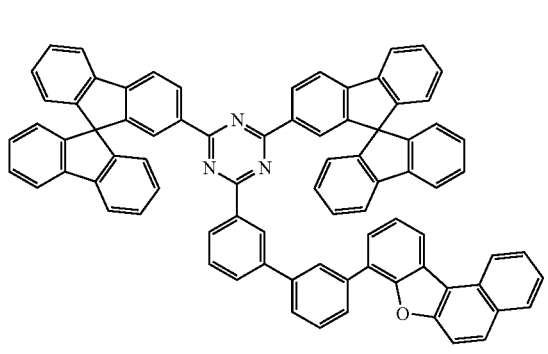
(114)
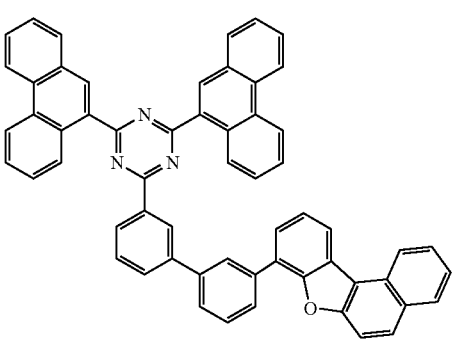
(115)

-continued
(116)
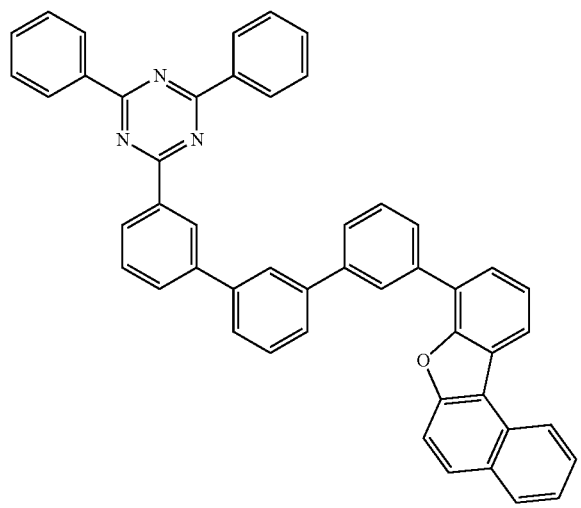
(117)
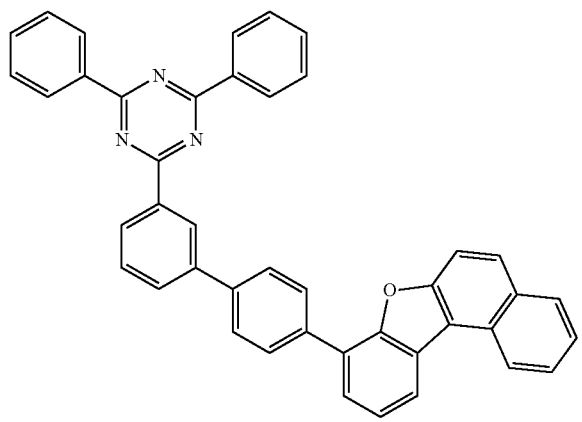
(118)
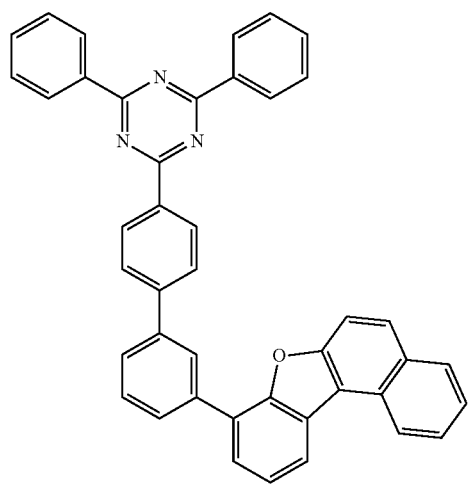
(119)
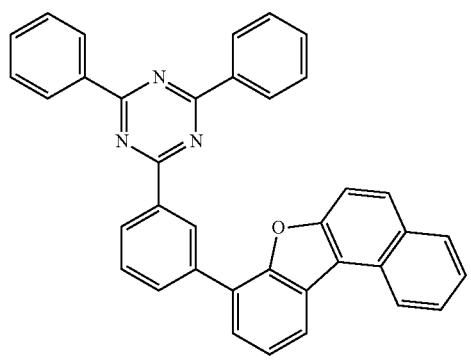
(120)
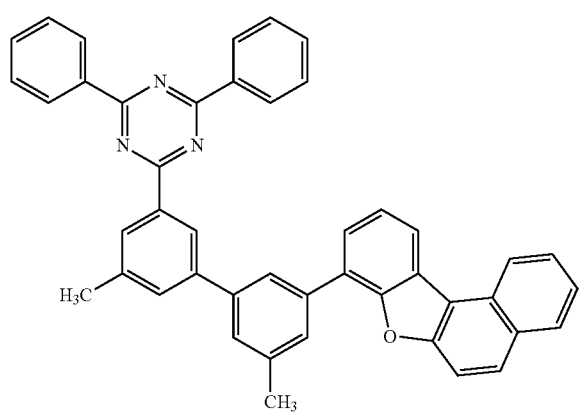

[Chemical Formula 16]
(121)
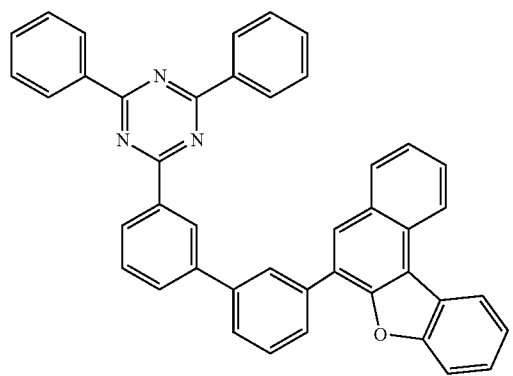
(122)
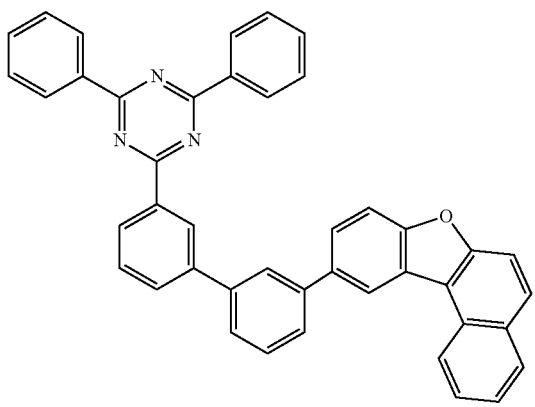
(123)
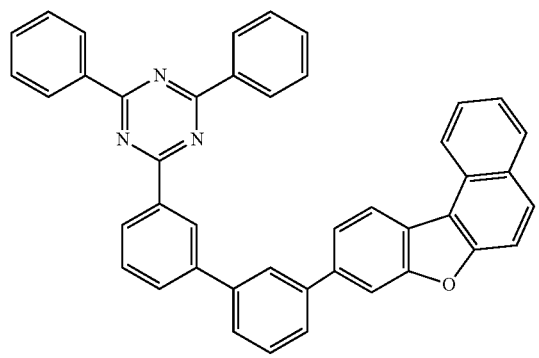
(124)
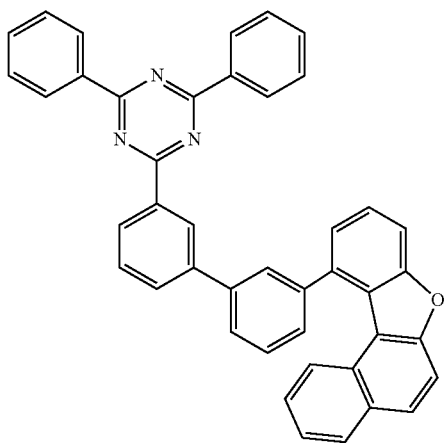
(125)
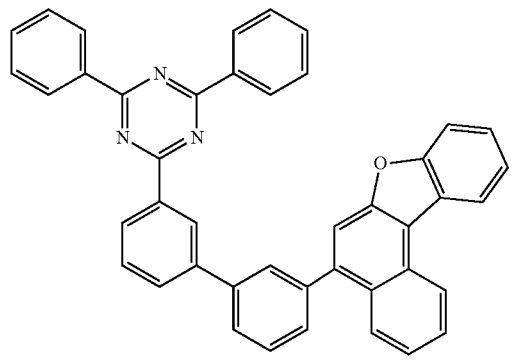
(126)
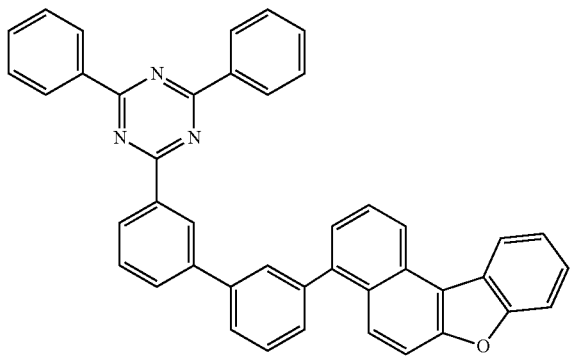

(127)
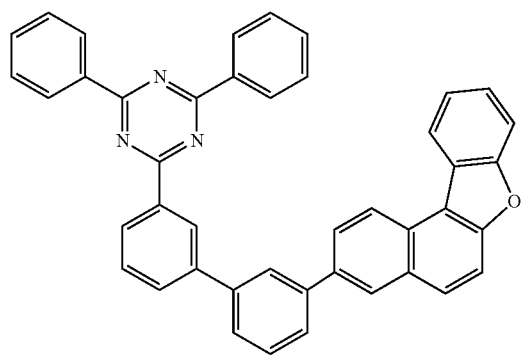
(128)
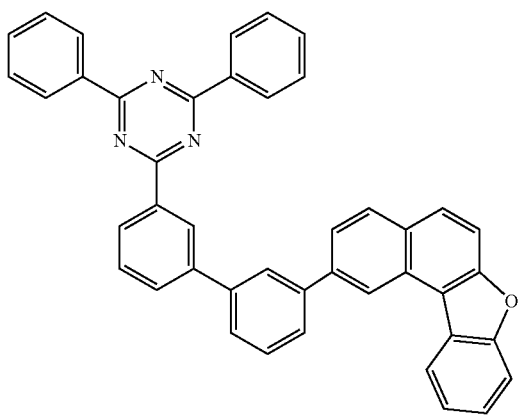
(129)
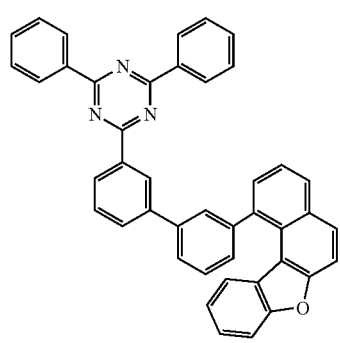
(130)
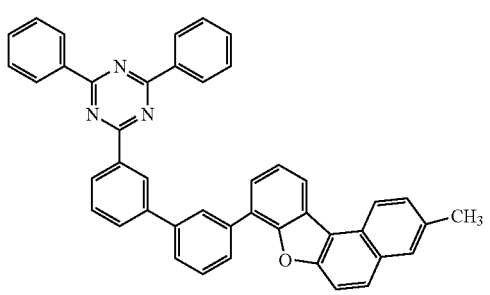
(131)
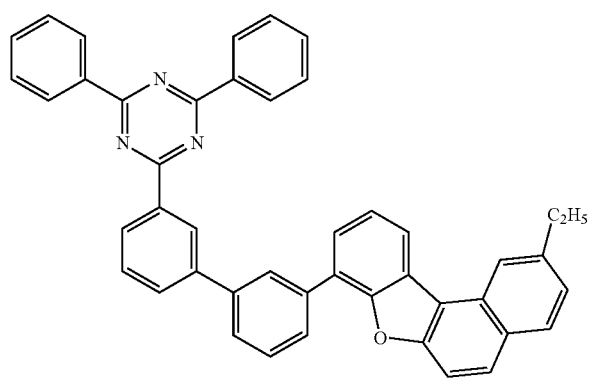
[Chemical Formula 17]
(132)
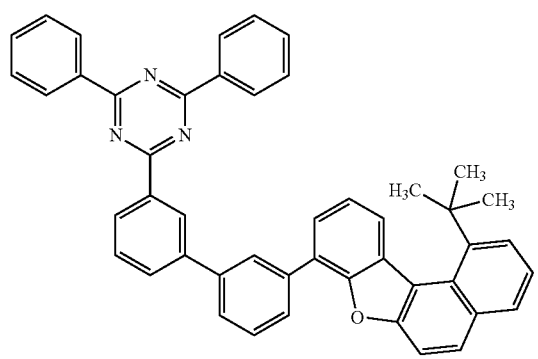
(133)
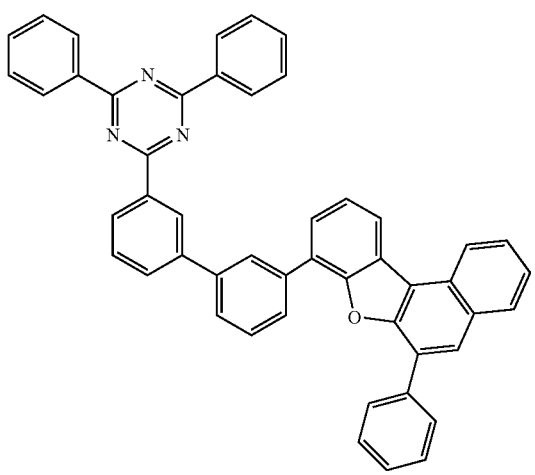

-continued
(134)
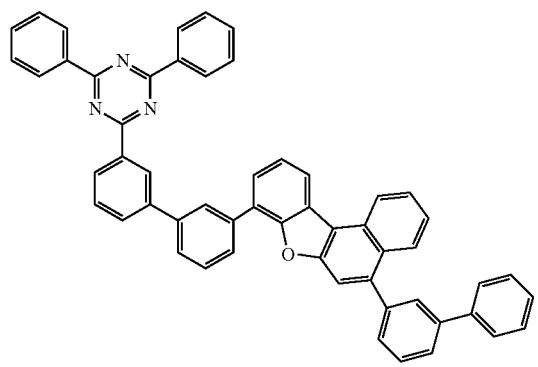
(135)
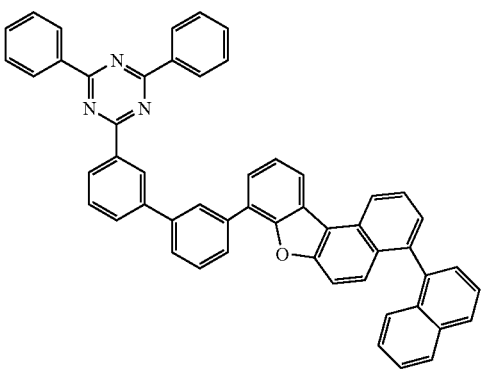
(136)
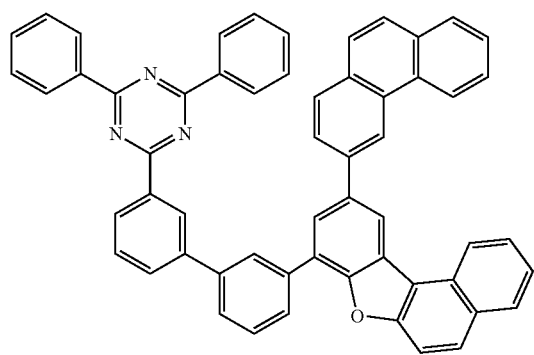
(137)
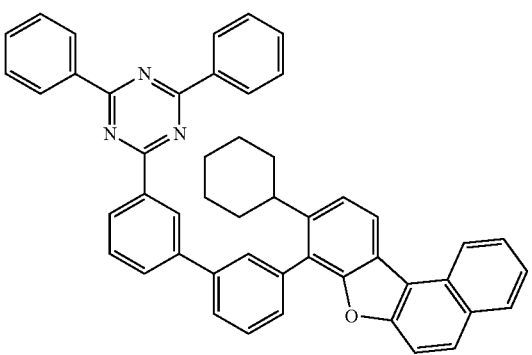
(138)
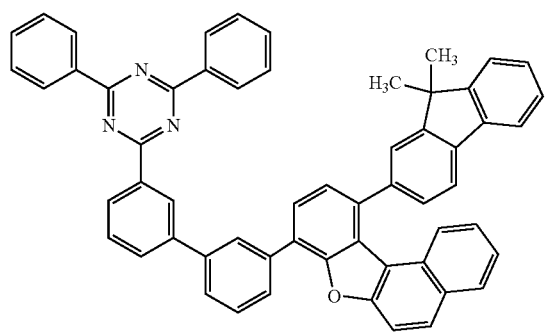
(139)
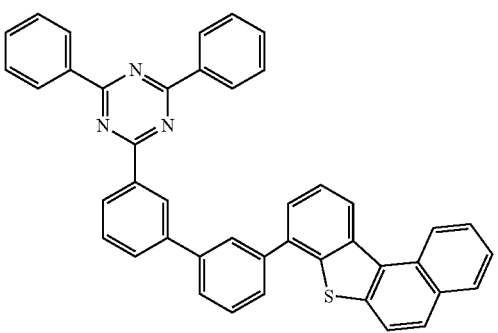
[Chemical Formula 18]
(140)
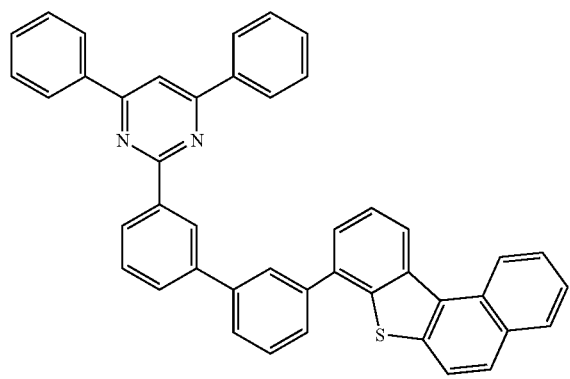
(141)
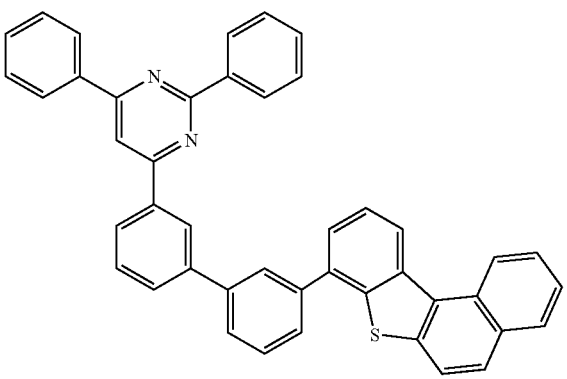

-continued
(142) 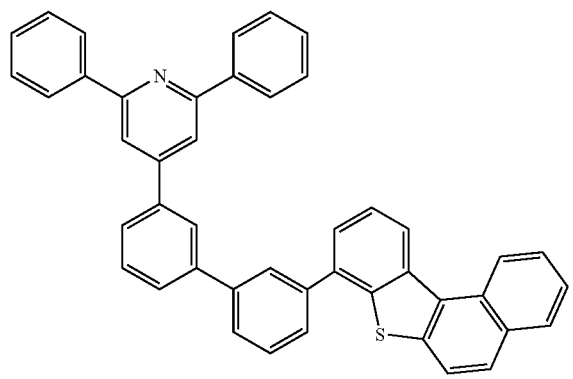
(143) 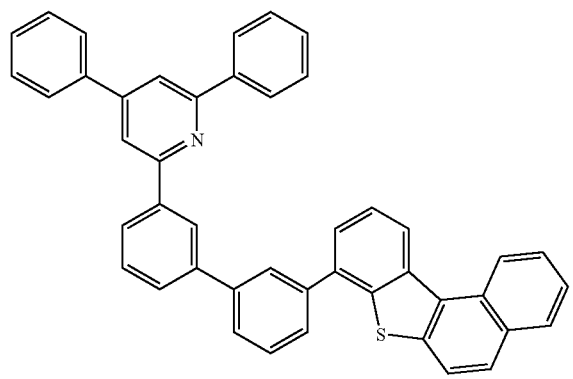
(144) 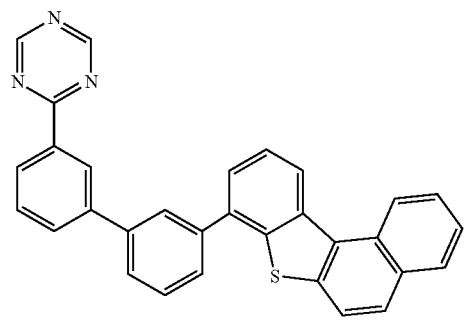
(145) 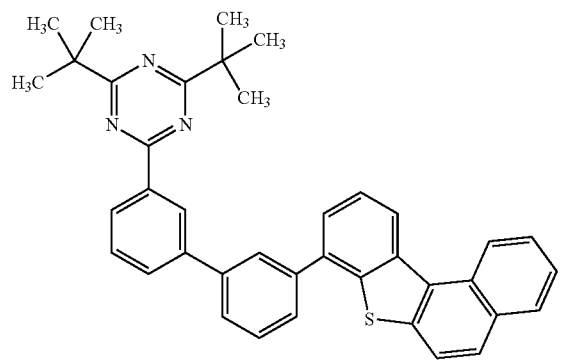
(146) 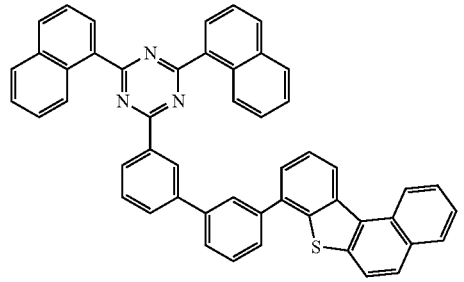
(147) 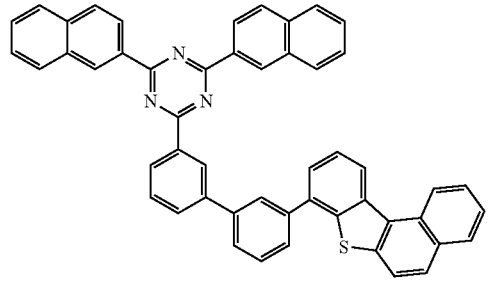
(148) 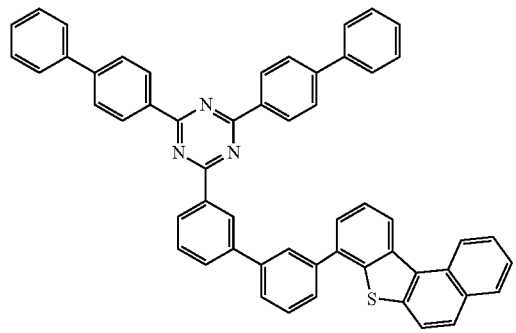
(149) 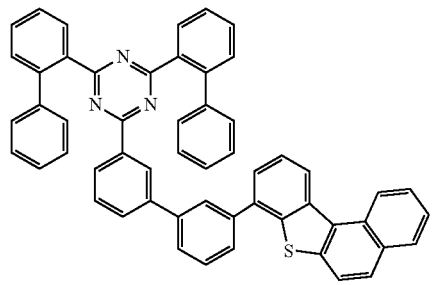

[Chemical Formula 19]
(150)
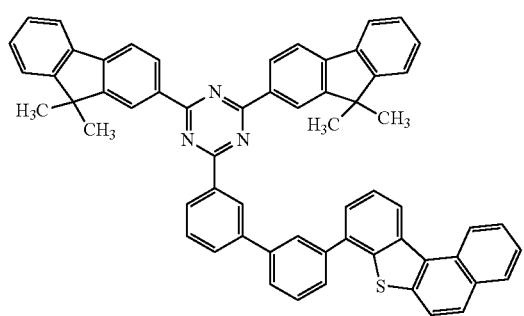
(151)
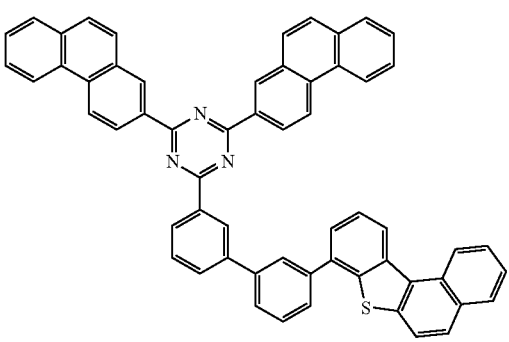
(152)
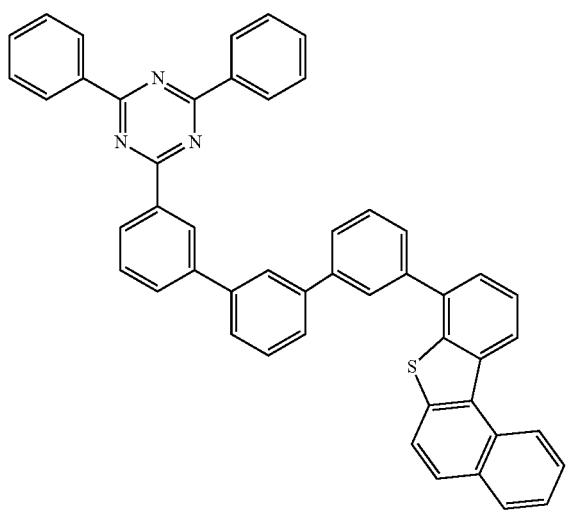
(153)
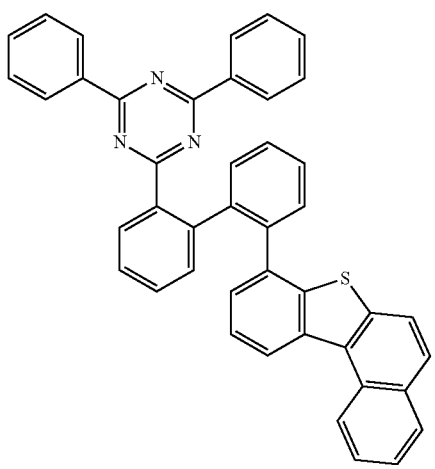
(154)
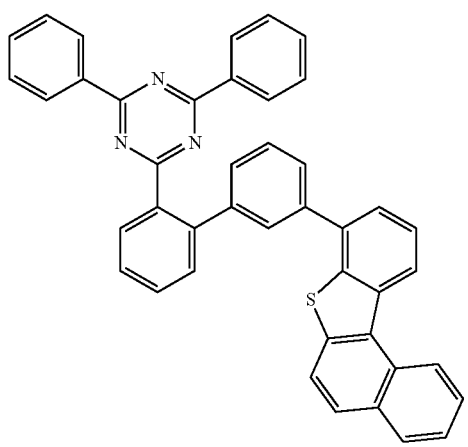
(155)
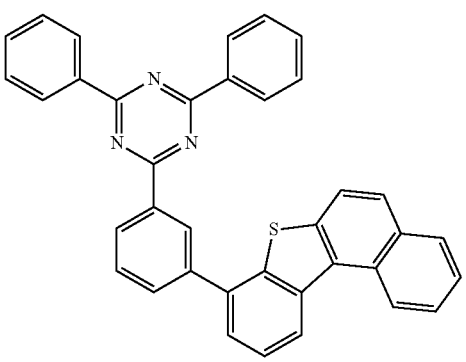

(156)
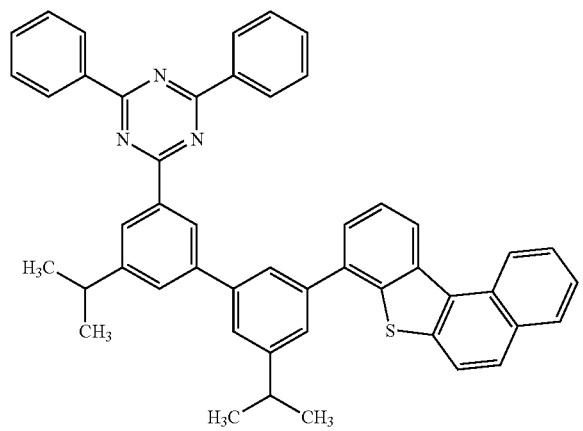
(157)
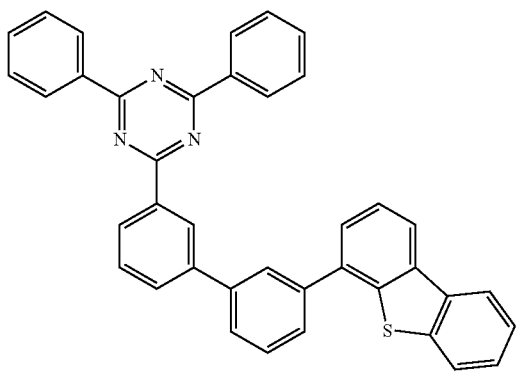
(158)
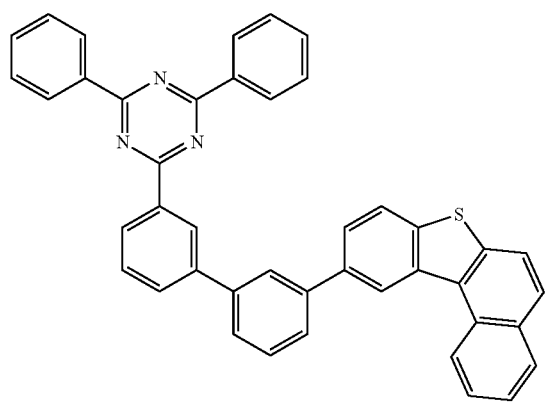
(159)
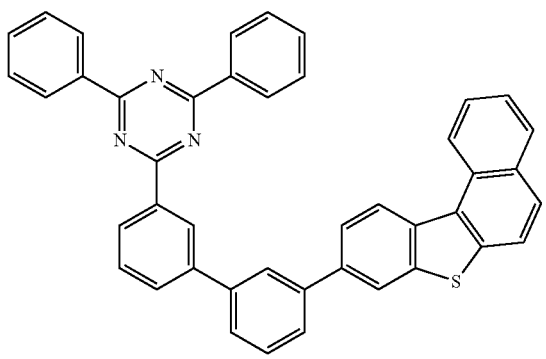
(160)
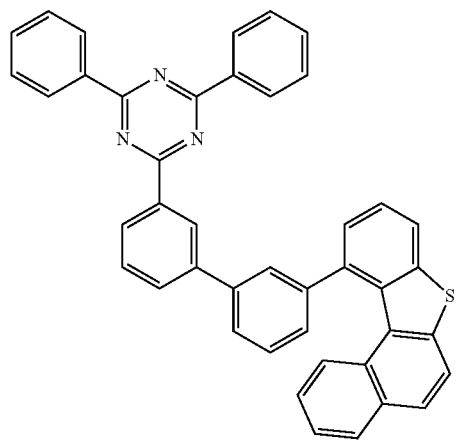

[Chemical Formula 20]
(161)
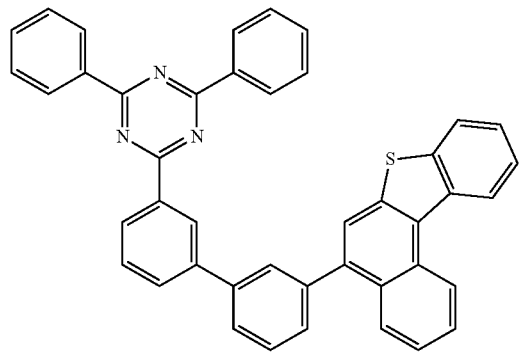
(162)
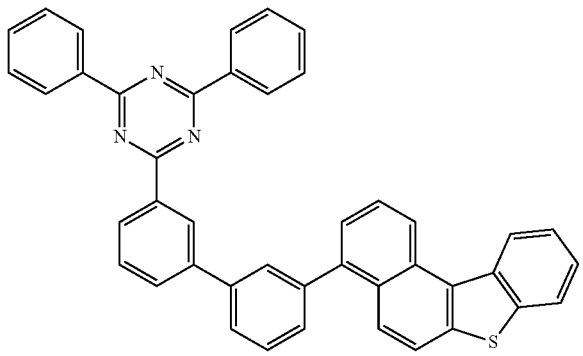
(163)
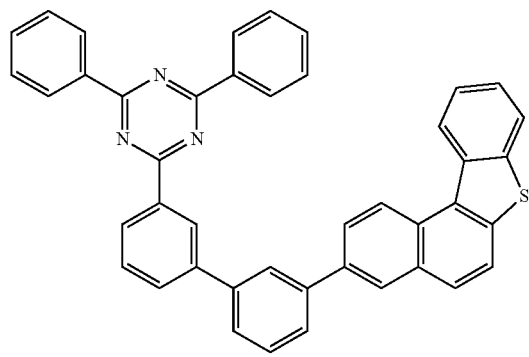
(164)
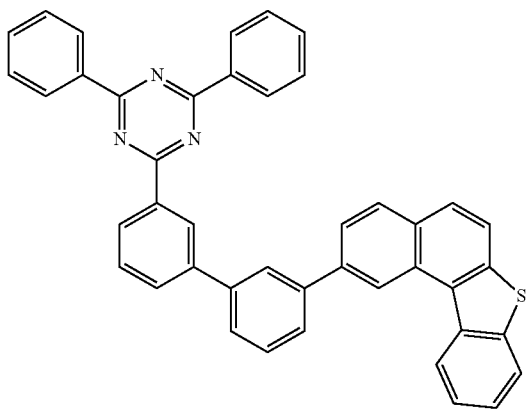
(165)
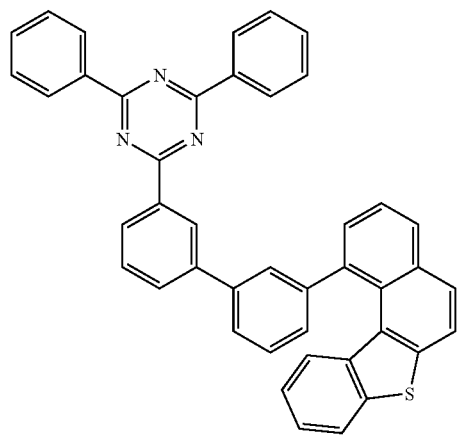
(166)
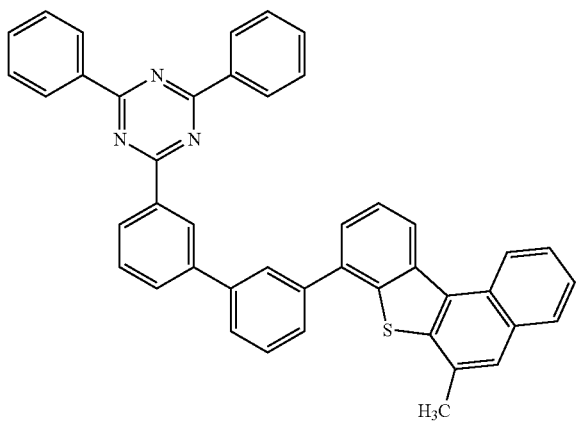

-continued
(167)
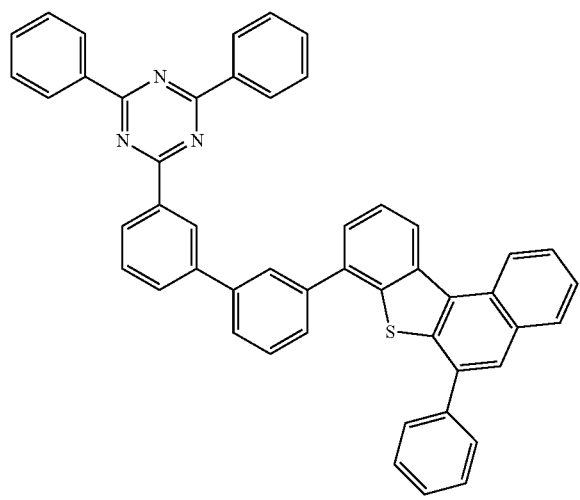
(168)
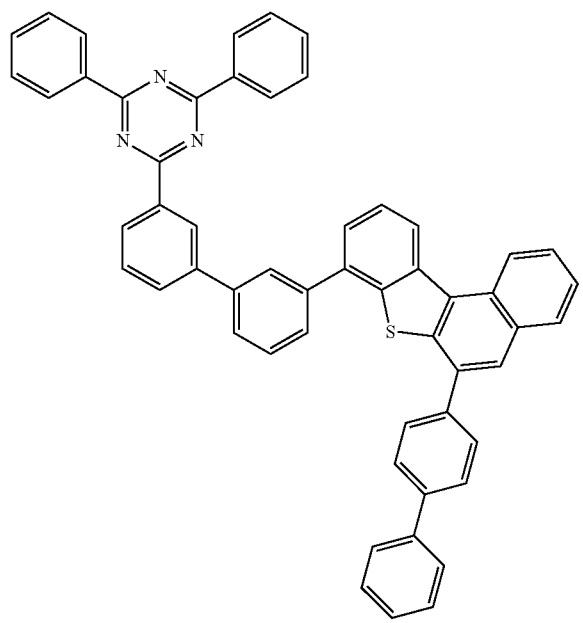
(169)
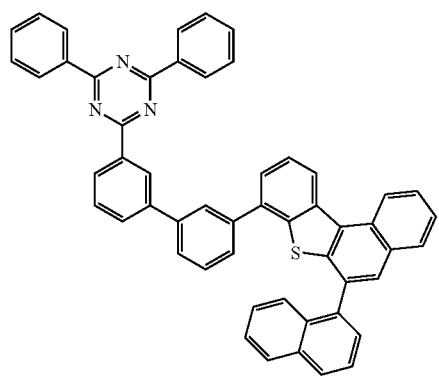
(170)
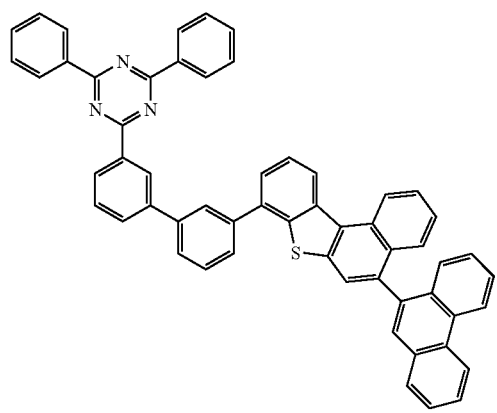
(171)
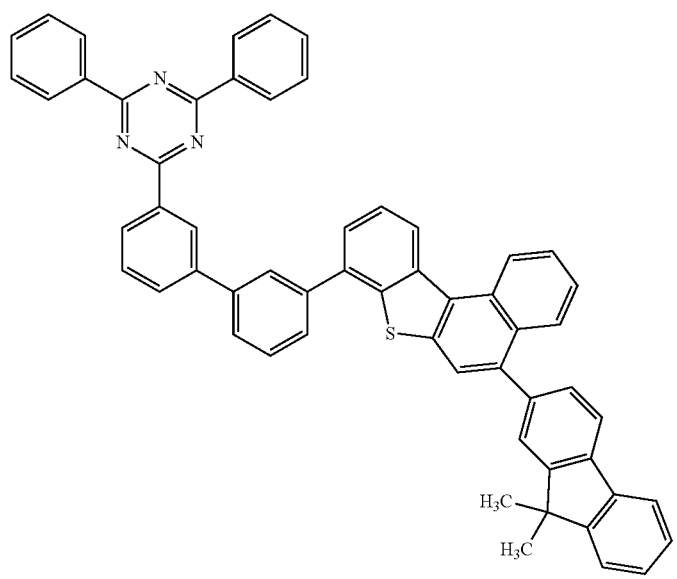

Note that organic compounds represented by Structural Formulae (100) to (171) are examples of the organic compound represented by General Formula (G1). The organic compound of one embodiment of the present invention is not limited thereto.

Next, an example of a method for synthesizing the organic compound of one embodiment of the present invention is described.

<<Method for Synthesizing Organic Compound Represented by General Formula (G1)>>

First, an example of a method for synthesizing the organic compound represented by General Formula (G1) will be described.

[Chemical Formula 21]

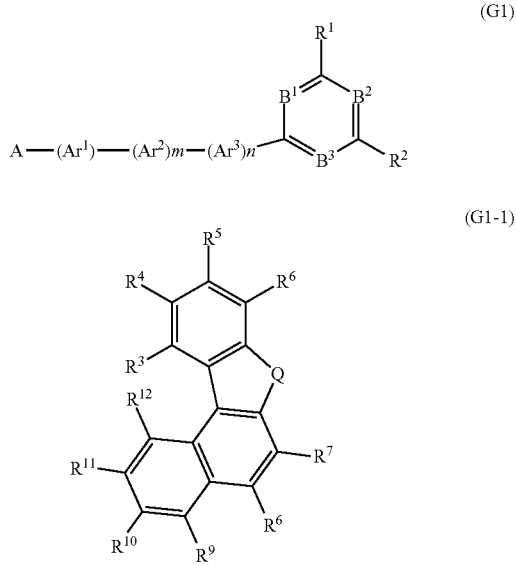

In General Formula (G1), $Ar^1$, $Ar^2$, and $Ar^3$ separately represent a substituted or unsubstituted phenylene group, and each of m and n is independently 0 or 1. $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $B^1$ to $B^3$ separately represent nitrogen or carbon, and at least one of $B^1$ to $B^3$ represents nitrogen. In addition, A is represented by General Formula (G1-1). Any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S (sulfur) or O (oxygen).

The organic compound (G1) of one embodiment of the present invention can be synthesized by Synthesis Scheme (A-1) shown below. That is, a halogen compound or a compound having a triflate group of a heterocyclic compound (a1) is coupled with a boronic acid or an organoboron compound of a benzo[b]naphtho[1,2-d]furan compound or a benzo[b]naphtho[1,2-d]thiophene compound (a2) by the Suzuki-Miyaura reaction using a palladium catalyst, whereby the organic compound (G1) of one embodiment of the present invention can be obtained.

[Chemical Formula 22]

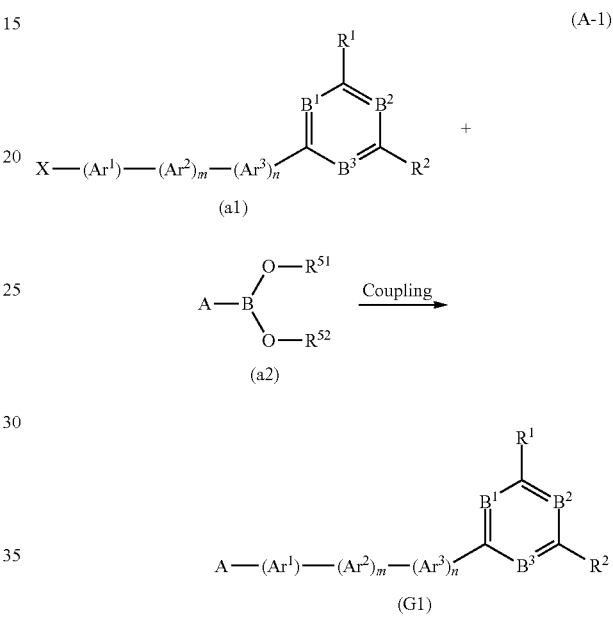

In Synthesis Scheme (A-1), $Ar^1$, $Ar^2$, and $Ar^3$ in the compound (a1) separately represent a substituted or unsubstituted phenylene group, and each of m and n is independently 0 or 1. $R^1$ and $R^2$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. $B^1$ to $B^3$ separately represent nitrogen or carbon, and at least one of $B^1$ to $B^3$ represents nitrogen. In addition, X represents a halogen or a triflate group. When X represents a halogen, chlorine, bromine, or iodine is particularly preferable as the halogen.

In addition, A in the compound (a2) is represented by General Formula (G1-1) below. In the case where the compound (a2) is a boronic acid, $R^{51}$ and $R^{52}$ each represent hydrogen. The boronic acid of the compound (a2) may be protected by ethylene glycol or the like, and in this case, $R^{51}$ and $R^{52}$ in the compound (a2) each represent an alkyl group having 1 to 6 carbon atoms. In the case where the compound (a2) is an organoboron compound, $R^{51}$ and $R^{52}$ may be the same or different and may be bonded to each other to form a ring.

[Chemical Formula 23]

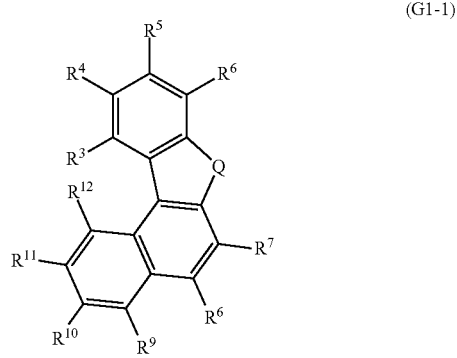

(G1-1)

In General Formula (G1-1), any one of $R^3$ to $R^{12}$ is bonded to $Ar^1$, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group. Furthermore, Q represents S (sulfur) or O (oxygen).

For Synthesis Scheme (A-1), palladium(II) acetate, tetrakis(triphenylphosphine)palladium(0), or the like can be used as the palladium catalyst. Examples of a ligand of the palladium catalyst include tri(ortho-tolyl)phosphine, triphenylphosphine, and tricyclohexylphosphine. As a base, an organic base such as sodium tert-butoxide, an inorganic base such as potassium carbonate or sodium carbonate, or the like can be used. As a solvent, any of the following can be used: toluene, xylene, benzene, an ether (e.g., 1,2-dimethoxyethane), an alcohol (e.g., ethanol), water, and a mixed solvent of any of them (e.g., a mixed solvent of toluene and ethanol, a mixed solvent of toluene and water, a mixed solvent of xylene and ethanol, a mixed solvent of xylene and water, or a mixed solvent of benzene and ethanol).

An organoboron compound or a boronic acid of a quinoxaline derivative may be coupled with a halogen compound or a compound having a triflate group of an aryl derivative by the Suzuki-Miyaura reaction shown by Synthesis Scheme (A-1).

The above is the description of a method for synthesizing the organic compound (G1) of one embodiment of the present invention; however, the present invention is not limited thereto, and another synthesis method may be employed.

Note that the above organic compounds which are embodiments of the present invention each have an electron-transport property and a hole-transport property and can thus be used as a host material in a light-emitting layer or can be used in an electron-transport layer or a hole-transport layer. Furthermore, the above organic compounds are preferably used in combination with a substance that emits phosphorescence (phosphorescent material), as host materials. In addition, the above organic compounds emit fluorescence and can thus be used as light-emitting substances of light-emitting elements. Accordingly, light-emitting elements containing these organic compounds are also included as embodiments of the present invention.

With the use of the organic compound of one embodiment of the present invention, a light-emitting element, a light-emitting device, an electronic device, or a lighting device with high emission efficiency can be obtained. In addition, a light-emitting element, a light-emitting device, an electronic device, or a lighting device with low power consumption can be obtained.

In this embodiment, one embodiment of the present invention has been described. Other embodiments of the present invention are described in the other embodiments. Note that one embodiment of the present invention is not limited thereto. In other words, since various embodiments of the invention are described in this embodiment and the other embodiments, one embodiment of the present invention is not limited to a particular embodiment. For example, although an example of use in a light-emitting element is described in this embodiment, one embodiment of the present invention is not limited thereto. Depending on circumstances, one embodiment of the present invention may be used in objects other than a light-emitting element. Furthermore, depending on circumstances, one embodiment of the present invention does not necessarily need to be used in a light-emitting element.

The structures described in this embodiment can be combined with any of the structures described in the other embodiments as appropriate.

Embodiment 2

In this embodiment, a light-emitting element including any of the organic compounds described in Embodiment 1 is described with reference to FIGS. 1A to 1D.

<<Basic Structure of Light-Emitting Element>>

A basic structure of a light-emitting element will be described. FIG. 1A illustrates a light-emitting element including, between a pair of electrodes, an EL layer having a light-emitting layer. Specifically, an EL layer 103 is provided between a first electrode 101 and a second electrode 102.

Figure 1B:
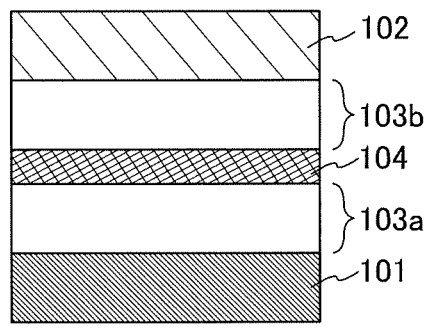

FIG. 1B illustrates a light-emitting element that has a stacked-layer structure (tandem structure) in which a plurality of EL layers (two EL layers 103a and 103b in FIG. 1B) are provided between a pair of electrodes and a charge-generation layer 104 is provided between the EL layers. With the use of such a tandem light-emitting element, a light-emitting device which can be driven at low voltage with low power consumption can be obtained.

The charge-generation layer 104 has a function of injecting electrons into one of the EL layers (103a or 103b) and injecting holes into the other of the EL layers (103b or 103a) when voltage is applied between the first electrode 101 and the second electrode 102. Thus, when voltage is applied in FIG. 1B such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a property of transmitting visible light (specifically, the charge-generation layer 104 has a visible light transmittance of 40% or more). The charge-generation layer 104 functions even when it has lower conductivity than the first electrode 101 or the second electrode 102.

Figure 1C:
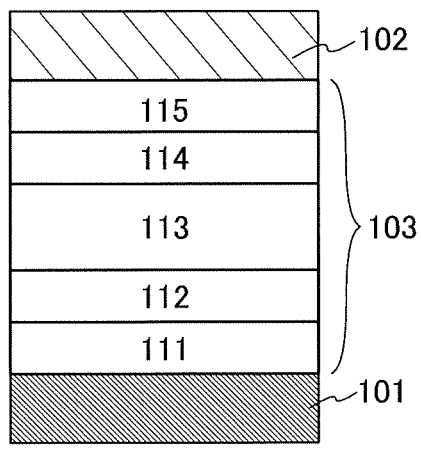

FIG. 1C illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1B, the layers in each EL layer are sequentially stacked from the anode side as described above. When the first electrode 101 is a cathode and the second electrode 102 is an anode, the stacking order is reversed.

The light-emitting layer 113 included in the EL layers (103, 103a, and 103b) contains an appropriate combination of a light-emitting substance and a plurality of substances, so that fluorescence or phosphorescence of a desired emission color can be obtained. The light-emitting layer 113 may have a stacked-layer structure having different emission colors. In that case, the light-emitting substance and other substances are different between the stacked light-emitting layers. Alternatively, the plurality of EL layers (103a and 103b) in FIG. 1B may exhibit their respective emission colors. Also in that case, the light-emitting substance and other substances are different between the light-emitting layers.

In the light-emitting element of one embodiment of the present invention, for example, a micro optical resonator (microcavity) structure in which the first electrode 101 is a reflective electrode and the second electrode 102 is a transflective electrode can be employed in FIG. 1C, whereby light emission from the light-emitting layer 113 in the EL layer 103 can be resonated between the electrodes and light emission obtained through the second electrode 102 can be intensified.

Note that when the first electrode 101 of the light-emitting element is a reflective electrode having a structure in which a reflective conductive material and a light-transmitting conductive material (transparent conductive film) are stacked, optical adjustment can be performed by controlling the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to exactly determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer emitting the desired light is, to be exact, the optical path length between the reflective region in the first electrode 101 and the light-emitting region in the light-emitting layer emitting the desired light. However, it is difficult to precisely determine the reflective region in the first electrode 101 and the light-emitting region in the light-emitting layer emitting the desired light; thus, it is assumed that the above effect can be sufficiently obtained wherever the reflective region and the light-emitting region may be set in the first electrode 101 and the light-emitting layer emitting the desired light.

The light-emitting element in FIG. 1C has a microcavity structure, so that light (monochromatic light) with different wavelengths can be extracted even if the same EL layer is used. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, and preferably higher than or equal to 40% and lower than or equal to 70%. These electrodes preferably have a resistivity of $1\times10^{-2}$ $\Omega$cm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, and preferably higher than or equal to 70% and lower than or equal to 100%. This electrode preferably has a resistivity of $1\times10^{-2}$ $\Omega$cm or less.

<<Specific Structure and Fabrication Method of Light-Emitting Element>>

Specific structures and specific fabrication methods of light-emitting elements of embodiments of the present invention will be described. Here, a light-emitting element having the tandem structure in FIG. 1B and a microcavity structure will be described with reference to FIG. 1D. In the light-emitting element in FIG. 1D, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

Figure 1D:
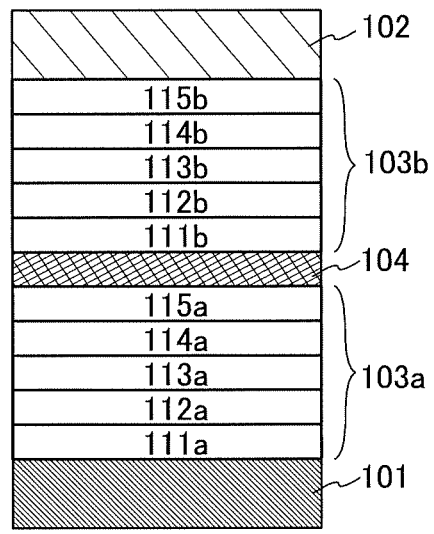

In the light-emitting element in FIG. 1D, when the first electrode 101 is an anode, a hole-injection layer 111a and a hole-transport layer 112a of the EL layer 103a are sequentially stacked over the first electrode 101 by a vacuum evaporation method. After the EL layer 103a and the charge-generation layer 104 are formed, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) inject holes from the first electrode 101 that is an anode and the charge-generation layer (104) to the EL layers (103, 103a, and 103b) and each contain a material with a high hole-injection property.

As examples of the material with a high hole-injection property, transition metal oxides such as molybdenum oxide, vanadium oxide, ruthenium oxide, tungsten oxide, and manganese oxide can be given. Alternatively, it is possible to use any of the following materials: phthalocyanine-based compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material with a high hole-injection property, a composite material containing a hole-transport material and an acceptor material (an electron-accepting material) can also be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed to have a single-layer structure using a composite material containing a hole-transport material and an acceptor material (electron-accepting material), or a stacked-layer structure in which a layer including a hole-transport material and a layer including an acceptor material (electron-accepting material) are stacked.

The hole-transport layers (112, 112a, and 112b) transport the holes, which are injected from the first electrode 101 and the charge-generation layer (104) by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 111a, and 111b) include an oxide of a metal belonging to any of Groups 4 to 8 of the periodic table. Specifically, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and the like can be used.

The hole-transport materials used for the hole-injection layers (111, 111a, and 111b) and the hole-transport layers (112, 112a, and 112b) are preferably substances with a hole mobility of greater than or equal to $10^{-6}$ cm$^2$/Vs. Note that other substances may be used as long as the substances have a hole-transport property higher than an electron-transport property.

Preferred hole-transport materials are π-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluor en-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl) triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4''-tris(carbazol-9-yl)triphenylamine (abbreviation: TCTA), 4,4',4''-tris(N,N-diphenylamino)triphenylamine (abbreviation: TDATA), and 4,4',4''-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis (3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4''-(benzene-1,3,5-triyl)tri (dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

A high molecular compound such as poly(N-vinylcarbazole) (abbreviation: PVK), poly(4-vinyltriphenylamine) (abbreviation: PVTPA), poly[N-(4-{N'-[4-(4-diphenylamino) phenyl]phenyl-N-phenylamino}phenyl)methacryla mide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b).

Next, in the light-emitting element in FIG. 1D, the light-emitting layer 113a is formed over the hole-transport layer 112a of the EL layer 103a by a vacuum evaporation method. After the EL layer 103a and the charge-generation layer 104 are formed, the light-emitting layer 113b is formed over the hole-transport layer 112b of the EL layer 103b by a vacuum evaporation method.

<Light-Emitting Layer>

The light-emitting layers (113, 113a, and 113b) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a and 113b) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

The light-emitting layers (113, 113a, and 113b) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

There is no particular limitation on light-emitting substances other than the above that can be used for the light-emitting layers (113, 113a, and 113b), and a light-emitting substance that converts singlet excitation energy into light emission in the visible light range or a light-emitting substance that converts triplet excitation energy into light emission in the visible light range can be used. Examples of the light-emitting substance are given below.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine](abbreviation: 1,6BnfAPrn), N,N'-(pyrene-1,6-diyl)bis[(N-phenylbenzo[b]naphtho[1,2-d]furan)-8-amine](abbreviation: 1,6BnfAPrn-02), and N,N'-(pyrene-1,6-diyl)bis[(6,N-diphenylbenzo[b]naphtho[1,2-d]furan)-8-amine](abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl) triphenylamine (abbreviation: PCBAPBA), perylene, 2,5,8, 11-tetra(tert-butyl)perylene (abbreviation: TBP), N,N'-(2-tert-butylanthracene-9,10-diyldi-4,1-phenylene)bis[N,N', N'-triphenyl-1,4-phenylenediamine] (abbreviation: DPABPA), N,9-diphenyl-N-[4-(9,10-diphenyl-2-anthryl) phenyl]-9H-carbazol-3-amine (abbreviation: 2PCAPPA), N-[4-(9,10-diphenyl-2-anthryl)phenyl]-N,N',N'-triphenyl-1, 4-phenylenediamine (abbreviation: 2DPAPPA), or the like.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN2]phenyl-κ C}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1, 2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H- imidazole]iridium(III) (abbreviation: [Ir(iPrpmi)₃]) and tris [3-(2,6-dimethylphenyl)-7-methylimidazo[1,2-f]phenanthridinato]iridium(III) (abbreviation: [Ir(dmpimpt-Me)₃]); organometallic complexes in which a phenylpyridine derivative having an electron-withdrawing group is a ligand, such as bis[2-(4',6'-difluorophenyl)pyridinato-N,$C^{2'}$]iridium (III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis {2-[3',5'-bis(trifluoromethyl)phenyl]pyridinato-N,$C^{2'}$}iridium(III) picolinate (abbreviation: [Ir(CF₃ppy)₂(pic)]), and bis[2-(4',6'-difluorophenyl)pyridinato-N,$C^{2'}$]iridium(III) acetylacetonate (abbreviation: FIr(acac)); and the like can be given.

As examples of a phosphorescent material which emits green or yellow light and whose emission spectrum has a peak wavelength at greater than or equal to 495 nm and less than or equal to 590 nm, the following substances can be given.

For example, organometallic complexes having a pyrimidine skeleton, such as tris(4-methyl-6-phenylpyrimidinato)iridium(III) (abbreviation: [Ir(mppm)₃]), tris(4-t-butyl-6-phenylpyrimidinato)iridium(III) (abbreviation: [Ir(tBuppm)₃]), (acetylacetonato)bis(6-methyl-4-phenylpyrimidinato)iridium(III) (abbreviation: [Ir(mppm)₂(acac)]), (acetylacetonato)bis(6-tert-butyl-4-phenylpyrimidinato)iridium (III) (abbreviation: [Ir(tBuppm)₂(acac)]), (acetylacetonato)bis[6-(2-norbornyl)-4-phenylpyrimidinato]iridium(III) (abbreviation: [Ir(nbppm)₂(acac)]), (acetylacetonato)bis[5-methyl-6-(2-methylphenyl)-4-phenylpyrimidinato]iridium (III) (abbreviation: [Ir(mpmppm)₂(acac)]), (acetylacetonato) bis {4,6-dimethyl-2-[6-(2,6-dimethylphenyl)-4-pyrimidinyl-κN3]phenyl-κC}iridium(III) (abbreviation: [Ir(dmppm-dmp)₂(acac)]), and (acetylacetonato)bis(4,6-diphenylpyrimidinato)iridium(III) (abbreviation: [Ir(dppm)₂(acac)]); organometallic complexes having a pyrazine skeleton, such as (acetylacetonato)bis(3,5-dimethyl-2-phenylpyrazinato)iridium(III) (abbreviation: [Ir(mppr-Me)₂(acac)]) and (acetylacetonato)bis(5-isopropyl-3-methyl-2-phenylpyrazinato)iridium(III) (abbreviation: [Ir(mppr-iPr)₂(acac)]); organometallic complexes having a pyridine skeleton, such as tris(2-phenylpyridinato-N,$C^{2'}$)iridium(III) (abbreviation: [Ir(ppy)₃]), bis(2-phenylpyridinato-N,$C^{2'}$)iridium(III) acetylacetonate (abbreviation: [Ir(ppy)₂(acac)]), bis(benzo[h]quinolinato)iridium(III) acetylacetonate (abbreviation: [Ir(bzq)₂(acac)]), tris(benzo[h]quinolinato)iridium (III) (abbreviation: [Ir(bzq)₃]), tris(2-phenylquinolinato-N,$C^{2'}$)iridium(III) (abbreviation: [Ir(pq)₃]), and bis(2-phenylquinolinato-N,$C^{2'}$)iridium(III) acetylacetonate (abbreviation: [Ir(pq)₂(acac)]); organometallic complexes such as bis(2,4-diphenyl-1,3-oxazolato-N,$C^{2'}$)iridium(III) acetylacetonate (abbreviation: [Ir(dpo)₂(acac)]), bis {2-[4'-(perfluorophenyl)phenyl]pyridinato-N,$C^{2'}$ }iridium(III) acetylacetonate (abbreviation: [Ir(p-PF-ph)₂(acac)]), and bis (2-phenylbenzothiazolato-N,$C^{2'}$)iridium(III) acetylacetonate (abbreviation: [Ir(bt)₂(acac)]); and rare earth metal complexes such as tris(acetylacetonato)(monophenanthroline)terbium(III) (abbreviation: [Tb(acac)₃(Phen)]) can be given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), and (dipivaloylmethanato)bis[4,6-di(naphthalen-1-yl)pyrimidinato]iridium(III) (abbreviation: [Ir(d1npm)₂(dpm)]); organometallic complexes having a pyrazine skeleton, such as (acetylacetonato) bis(2,3,5-triphenylpyrazinato)iridium(III) (abbreviation: [Ir(tppr)₂(acac)]), bis(2,3,5-triphenylpyrazinato) (dipivaloylmethanato)iridium(III) (abbreviation: [Ir(tppr)₂(dpm)]), bis {4,6-dimethyl-2-[3-(3,5-dimethylphenyl)-5-phenyl-2-pyrazinyl-κN]phenyl-κC}(2,6-dimethyl-3,5-heptanedionato-$κ^2$O,O')iridium(III) (abbreviation: [Ir(dmdppr-P)₂(dibm)]), bis{4,6-dimethyl-2-[5-(4-cyano-2,6-dimethylphenyl)-3-(3,5-dimethylphenyl)-2-pyrazin yl-κN] phenyl-κC}(2,2,6,6-tetramethyl-3,5-heptanedionato-$κ^2$O, O')iridium(III) (abbreviation: [Ir(dmdppr-dmCP)₂(dpm)]), (acetylacetonato)bis[2-methyl-3-phenylquinoxalinato-N, $C^{2'}$]iridium(III) (abbreviation: [Ir(mpq)₂(acac)]), (acetylacetonato)bis(2,3-diphenylquinoxalinato-N,$C^{2'}$)iridium(III) (abbreviation: [Ir(dpq)₂(acac)]), and (acetylacetonato)bis[2, 3-bis(4-fluorophenyl)quinoxalinato]iridium(III) (abbreviation: [Ir(Fdpq)₂(acac)]); organometallic complexes having a pyridine skeleton, such as tris(1-phenylisoquinolinato-N, $C^{2'}$)iridium(III) (abbreviation: [Ir(piq)₃]) and bis(1-phenylisoquinolinato-N,$C^{2'}$)iridium(III) acetylacetonate (abbreviation: [Ir(piq)₂(acac)]); platinum complexes such as 2,3, 7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)₃ (Phen)]) and tris[1-(2-thenoyl)-3,3,3-trifluoroacetonato] (monophenanthroline)europium(III) (abbreviation: [Eu (TTA)₃(Phen)]) can be given.

As the organic compounds (the host material and the assist material) used in the light-emitting layers (113, 113*a*, and 113*b*), one or more kinds of substances having a larger energy gap than the light-emitting substance (the guest material) are used. Note that any of the hole-transport materials listed above and the electron-transport materials given below may be used as the organic compounds (the host material and the assist material).

When the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

Specific examples include metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)-tris(1-phenyl-1H-benzimidazole) (abbreviation: TPBI), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), and 9-[4-(5-phenyl-1,3,4-oxadiazol-2-yl)phenyl]-9H-carbazole (abbreviation: CO11); and aromatic amine compounds such as NPB, TPD, and BSPB.

In addition, condensed polycyclic aromatic compounds such as anthracene derivatives, phenanthrene derivatives, pyrene derivatives, chrysene derivatives, and dibenzo[g,p]chrysene derivatives can be used. Specifically, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N",N",N''',N'''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), or the like can be used.

In the case where a plurality of organic compounds are used for the light-emitting layers (113, 113a, and 113b), compounds that form an exciplex are preferably used in combination with a phosphorescent substance. With such a structure, light emission can be obtained by exciplex-triplet energy transfer (ExTET), which is energy transfer from an exciplex to a phosphorescent substance. In that case, although any of various organic compounds can be used in an appropriate combination, in order to form an exciplex efficiently, it is particularly preferable to combine a compound that easily accepts holes (hole-transport material) and a compound that easily accepts electrons (electron-transport material). As the hole-transport material and the electron-transport material, specifically, any of the materials described in this embodiment can be used.

The TADF material is a material that can up-convert a triplet excited state into a singlet excited state (i.e., reverse intersystem crossing is possible) using a little thermal energy and efficiently exhibits light emission (fluorescence) from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), and an octaethylporphyrin-platinum chloride complex (abbreviation: PtCl$_2$OEP).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be combined with another organic compound.

In the light-emitting element in FIG. 1D, the electron-transport layer 114a is formed over the light-emitting layer 113a of the EL layer 103a by a vacuum evaporation method. After the EL layer 103a and the charge-generation layer 104 are formed, the electron-transport layer 114b is formed over the light-emitting layer 113b of the EL layer 103b by a vacuum evaporation method.

<Electron-Transport Layer>

The electron-transport layers (114, 114a, and 114b) transport the electrons, which are injected from the second electrode 102 and the charge-generation layer (104) by the electron-injection layers (115, 115a, and 115b), to the light-emitting layers (113, 113a, and 113b). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1\times10^{-6}$ cm$^2$/Vs. Note that other substances may also be used as long as the substances have an electron-transport property higher than a hole-transport property.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, bis[2-(2-hydroxyphenyl)benzoxazolato]zinc(II) (abbreviation: Zn(BOX)$_2$), and bis[2-(2-hydroxyphenyl)benzothiazolato]zinc (abbreviation: Zn(BTZ)$_2$), heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[fh]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Alternatively, a high molecular compound such as poly(2,5-pyridinediyl) (abbreviation: PPy), poly[(9,9-dihexylfluorene-2,7-diyl)-co-(pyridine-3,5-diyl)](abbreviation: PF-Py), or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, but may be a stack of two or more layers each containing any of the above substances.

Next, in the light-emitting element in FIG. 1D, the electron-injection layer 115a is formed over the electron-transport layer 114a of the EL layer 103a by a vacuum evaporation method. Subsequently, the EL layer 103a and the charge-generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound like erbium fluoride (ErF$_3$) can also be used. Electride may also be used for the electron-injection layers (115, 115a, and 115b). Examples of the electride include a substance in which electrons are added at high concentration to calcium oxide-aluminum oxide. Any of the substances for forming the electron-transport layers (114, 114a, and 114b), which are given above, can also be used.

A composite material in which an organic compound and an electron donor (donor) are mixed may also be used for the electron-injection layers (115, 115a, and 115b). Such a composite material is excellent in an electron-injection property and an electron-transport property because electrons are generated in the organic compound by the electron donor. The organic compound here is preferably a material excellent in transporting the generated electrons; specifically, for example, the electron-transport materials for forming the electron-transport layers (114, 114a, and 114b) (e.g., a metal complex or a heteroaromatic compound) can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Further alternatively, an organic compound such as tetrathiafulvalene (abbreviation: TTF) can be used.

In the case where light obtained from the light-emitting layer 113b is amplified in the light-emitting element illustrated in FIG. 1D, for example, the optical path length between the second electrode 102 and the light-emitting layer 113b is preferably less than one fourth of the wavelength λ of light emitted from the light-emitting layer 113b. In that case, the optical path length can be adjusted by changing the thickness of the electron-transport layer 114b or the electron-injection layer 115b.

<Charge-Generation Layer>

The charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 by using any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F$_4$-TCNQ), chloranil, and the like. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is used.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

<Substrate>

The light-emitting element described in this embodiment can be formed over any of a variety of substrates. Note that the type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111a and 111b), the hole-transport layers (112a and 112b), the light-emitting layers (113a and 113b), the electron-transport layers (114a and 114b), the electron-injection layers (115a and 115b)) included in the EL layers and the charge-generation layer 104 of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nanoimprinting), or the like.

Note that materials that can be used for the functional layers (the hole-injection layers (111a and 111b), the hole-transport layers (112a and 112b), the light-emitting layers (113a and 113b), the electron-transport layers (114a and 114b), and the electron-injection layers (115a and 115b)) that are included in the EL layers (103a and 103b) and the charge-generation layer 104 in the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot may be a colloidal quantum dot, an alloyed quantum dot, a core-shell quantum dot, a core quantum dot, or the like.

The structures described in this embodiment can be combined with any of the structures described in the other embodiments as appropriate.

Embodiment 3

Figure 2A:
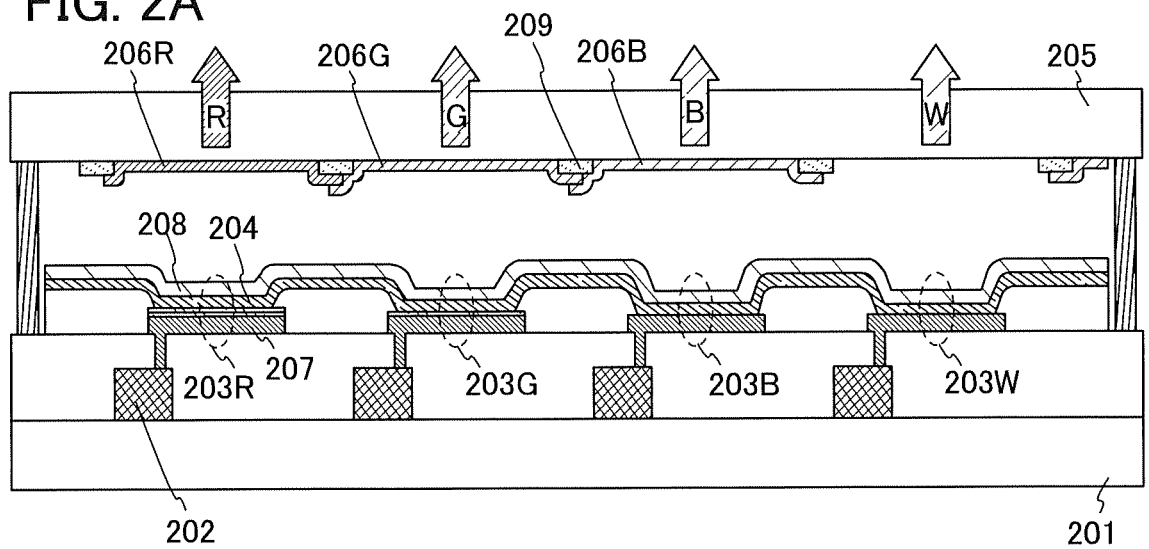
FIGS. 2A to 2C illustrate light-emitting devices.

In this embodiment, a light-emitting device of one embodiment of the present invention is described. Note that a light-emitting device illustrated in FIG. 2A is an active-matrix light-emitting device in which transistors (FETs) 202 are electrically connected to light-emitting elements (203R, 203G, 203B, and 203W) over a first substrate 201. The light-emitting elements (203R, 203G, 203B, and 203W) include a common EL layer 204 and each have a microcavity structure in which the optical path length between electrodes is adjusted depending on the emission color of the light-emitting element. The light-emitting device is a top-emission light-emitting device in which light is emitted from the EL layer 204 through color filters (206R, 206G, and 206B) formed on a second substrate 205.

The light-emitting device illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
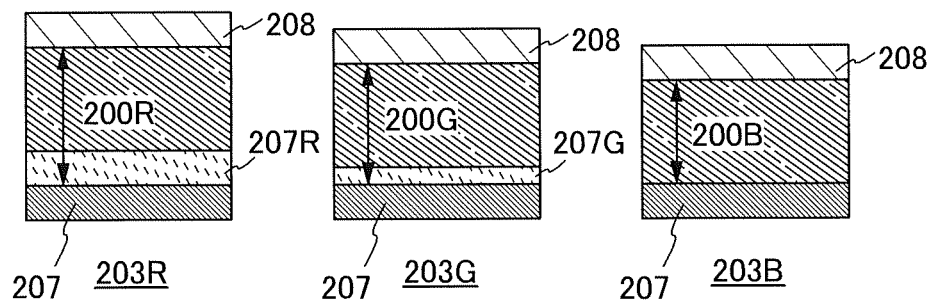

In the case where the light-emitting element 203R functions as a red light-emitting element, the light-emitting element 203G functions as a green light-emitting element, the light-emitting element 203B functions as a blue light-emitting element, and the light-emitting element 203W functions as a white light-emitting element in FIG. 2A, for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2B. Note that optical adjustment can be performed in such a manner that a conductive layer 207R is stacked over the first electrode 207 in the light-emitting element 203R and a conductive layer 207G is stacked over the first electrode 207 in the light-emitting element 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting element 203R, whereby red light emission can be obtained from the light-emitting element 203R. Furthermore, the color filter 206G that transmits only light in the green wavelength range is provided in a position overlapping with the light-emitting element 203G, whereby green light emission can be obtained from the light-emitting element 203G. Moreover, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
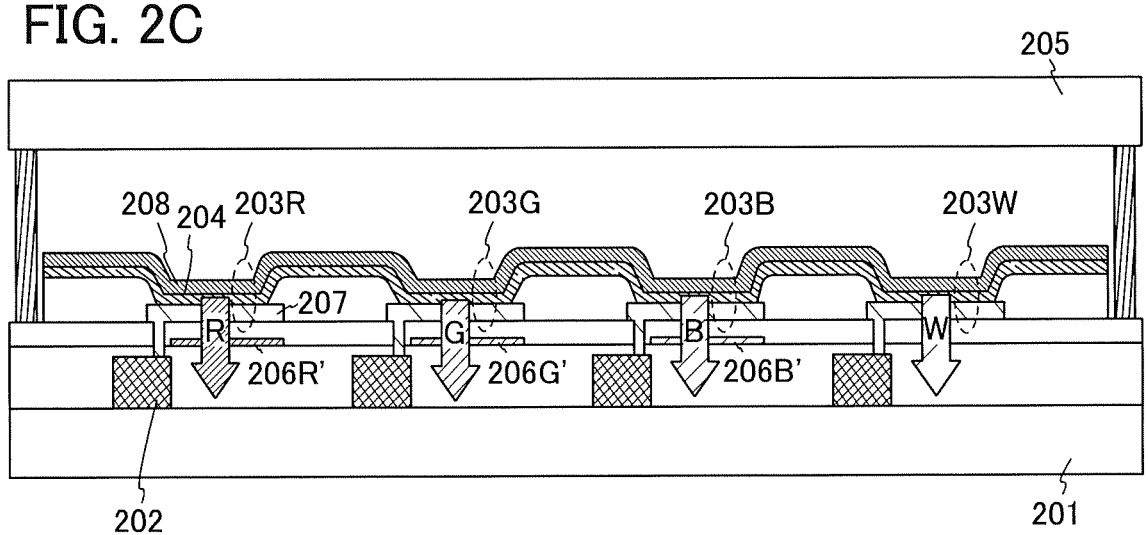

Although the light-emitting device in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting device, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B') are provided so as to be closer to the first substrate 201 than the light-emitting elements (203R, 203G, and 203B) are.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected depending on the emission color of the light-emitting element.

With the above structure, a light-emitting device including light-emitting elements that exhibit a plurality of emission colors can be fabricated.

Note that the structures described in this embodiment can be combined with any of the structures described in the other embodiments as appropriate.

Embodiment 4

In this embodiment, a light-emitting device of one embodiment of the present invention is described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is one embodiment of the present invention. Note that any of the light-emitting elements described in other embodiments can be used in the light-emitting device described in this embodiment.

In this embodiment, an active-matrix light-emitting device will be described with reference to FIGS. 3A and 3B.

Figure 3A:
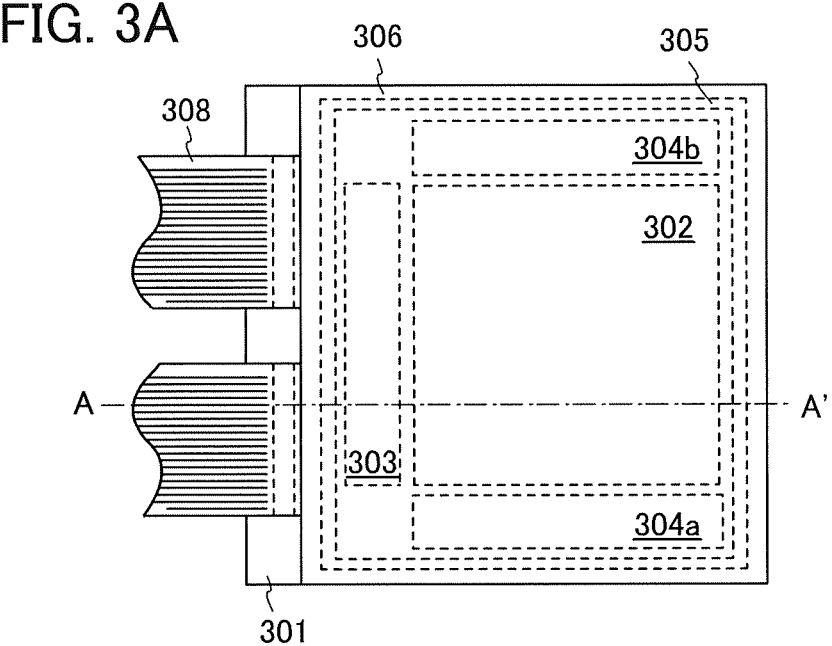
FIGS. 3A and 3B illustrate a light-emitting device.
Figure 3B:
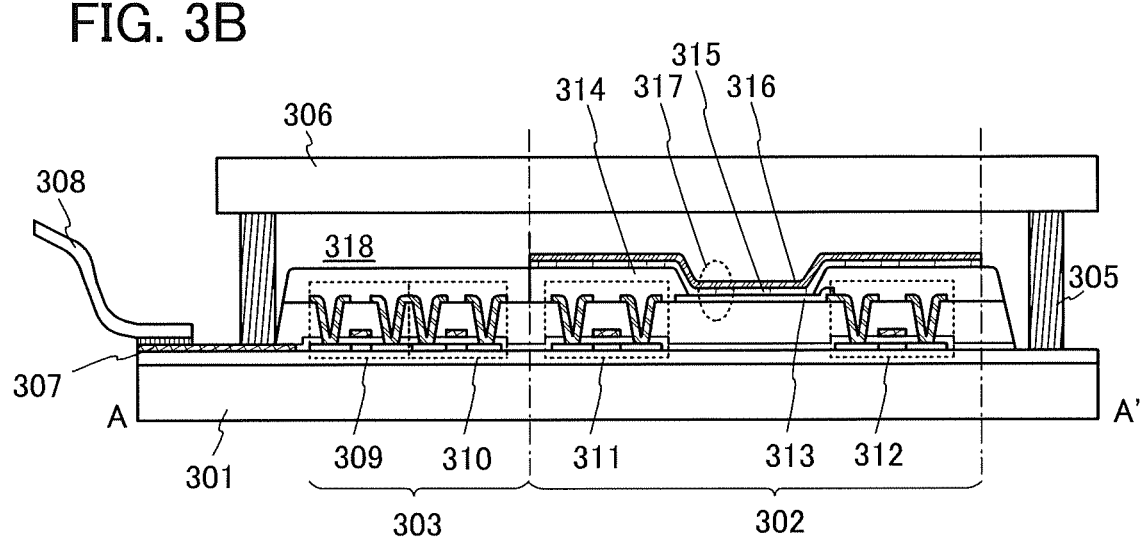

FIG. 3A is a top view illustrating the light-emitting device, and FIG. 3B is a cross-sectional view taken along chain line A-A' in FIG. 3A. The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting element 317 described in this embodiment. Although not illustrated, the second electrode 316 is electrically connected to the FPC 308 that is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, acrylic, or the like can be used. In the case where glass frit is used for the sealant, the first substrate 301 and the second substrate 306 are preferably glass substrates in terms of adhesion.

Accordingly, the active-matrix light-emitting device can be obtained.

In the case where the active-matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments as appropriate.

Embodiment 5

In this embodiment, examples of a variety of electronic devices and an automobile manufactured using the light-emitting device of one embodiment of the present invention or a display device including the light-emitting element of one embodiment of the present invention are described.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4A illustrates a mobile computer that can include a switch 7009, an infrared port 7010, and the like in addition to the above components.

FIG. 4B illustrates a portable image reproducing device (e.g., a DVD player) that is provided with a recording medium and can include a second display portion 7002, a recording medium reading portion 7011, and the like in addition to the above components.

FIG. 4C illustrates a goggle-type display that can include the second display portion 7002, a support 7012, an earphone 7013, and the like in addition to the above components.

FIG. 4D illustrates a digital camera that has a television reception function and can include an antenna 7014, a shutter button 7015, an image receiving portion 7016, and the like in addition to the above components.

FIG. 4E illustrates a cellular phone (including a smartphone) and can include the display portion 7001, a microphone 7019, the speaker 7003, a camera 7020, an external connection portion 7021, an operation button 7022, the like in the housing 7000.

FIG. 4F illustrates a large-size television set (also referred to as TV or a television receiver) and can include the housing 7000, the display portion 7001, the speaker 7003, and the like. In addition, here, the housing 7000 is supported by a stand 7018.

The electronic devices illustrated in FIGS. 4A to 4F can have a variety of functions, such as a function of displaying a variety of data (a still image, a moving image, a text image, and the like) on the display portion, a touch panel function, a function of displaying a calendar, date, time, and the like, a function of controlling a process with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, an electronic device including a plurality of display portions can have a function of displaying image data mainly on one display portion while displaying text data on another display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that can be provided for the electronic devices illustrated in FIGS. 4A to 4F are not limited to those described above, and the electronic devices can have a variety of functions.

FIG. 4G illustrates a smart watch, which includes the housing 7000, the display portion 7001, operation buttons 7022 and 7023, a connection terminal 7024, a band 7025, a clasp 7026, and the like.

The display portion 7001 mounted in the housing 7000 serving as a bezel includes a non-rectangular display region. The display portion 7001 can display an icon 7027 indicating time, another icon 7028, and the like. The display portion 7001 may be a touch panel (an input/output device) including a touch sensor (an input device).

The smart watch illustrated in FIG. 4G can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting device of one embodiment of the present invention or the display device including the light-emitting element of one embodiment of the present invention can be used in the display portion of each electronic device described in this embodiment, enabling display with high color purity.

Figure 5A:
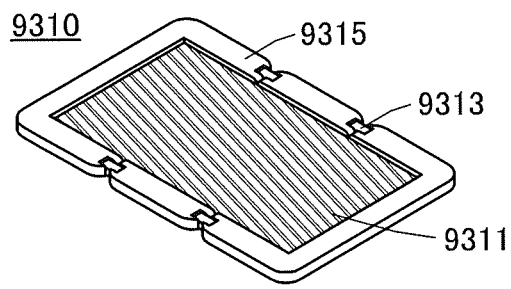
FIGS. 5A to 5C illustrate an electronic device.
Figure 5B:
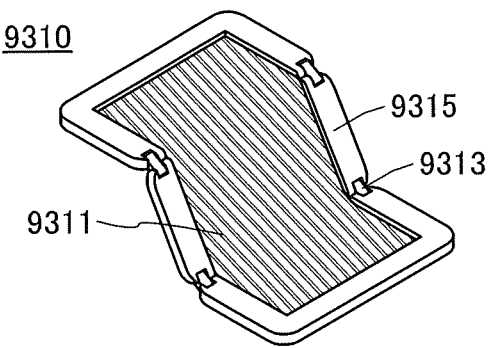
Figure 5C:
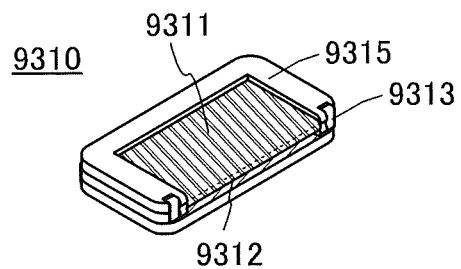

Another electronic device including the light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, display with high color purity can be performed. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 35A:
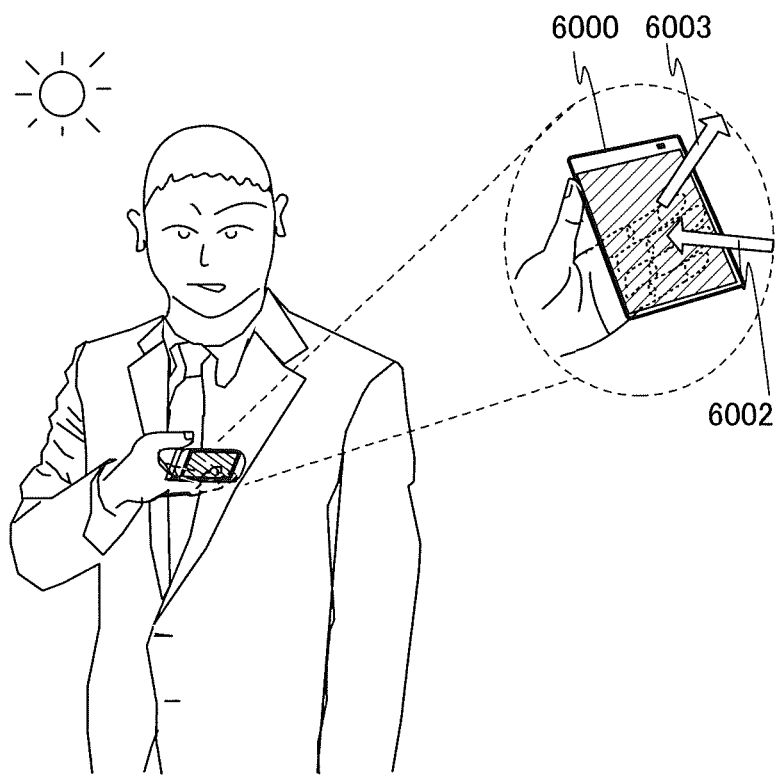
FIGS. 35A and 35B illustrate examples of the use of an electronic device.

Examples of the use of an electronic device will be described with reference to FIGS. 35A and 35B. Note that the electronic device described here includes the display device including the light-emitting element of one embodiment of the present invention in a display portion thereof. Thus, the display portion can perform display both in a reflective mode with a reflective liquid crystal element and in a transmissive mode with the light-emitting element. FIG. 35A illustrates an example of the use of the electronic device in an outdoor environment in the daytime with high illuminance, and FIG. 35B illustrates an example of the use of the electronic device in an outdoor environment at night with low illuminance.

In the high-illuminance environment, an electronic device 6000 is operated in a reflective display mode or a reflective-emissive display mode, and display is performed using reflected light 6003 obtained by reflecting external light 6002, as illustrated in FIG. 35A. This operation enables high visibility to be ensured also in the high-illuminance environment, and can achieve high display quality and low power consumption.

Figure 35B:
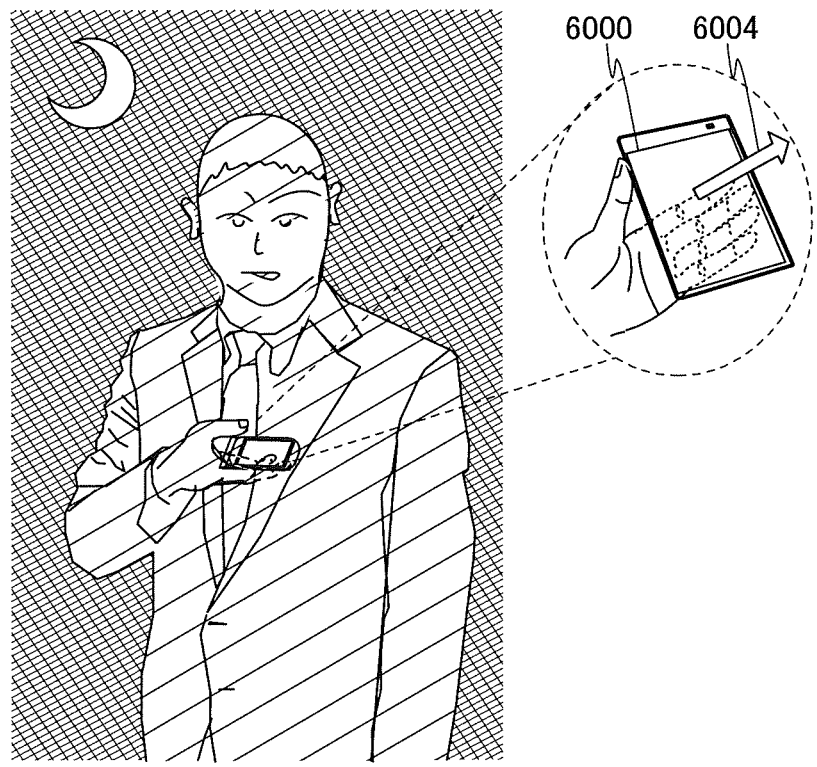

In the low-illuminance environment, the electronic device 6000 is operated in an emissive display mode or a reflective-emissive display mode, and display is performed using emitted light 6004 from the display device, as illustrated in FIG. 35B. This operation enables high visibility to be ensured also in the low-illuminance environment.

Figure 6A:
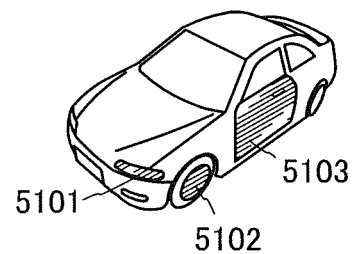
FIGS. 6A and 6B illustrate an automobile.
Figure 6B:
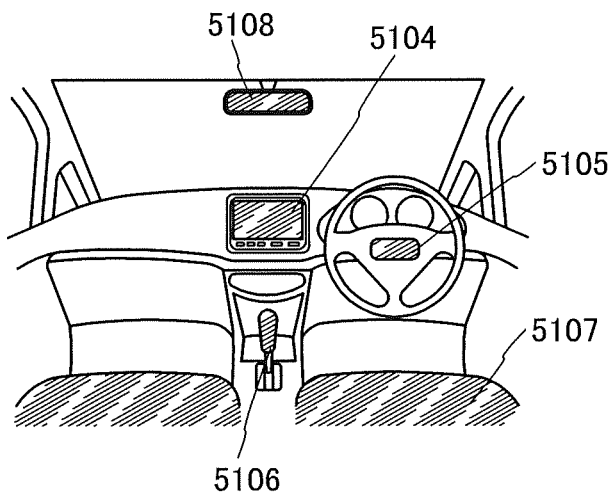

FIGS. 6A and 6B illustrate an automobile including the light-emitting device. The light-emitting device can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

As described above, the electronic devices and automobiles can be obtained using the light-emitting device or the display device of one embodiment of the present invention. In that case, display with high color purity can be performed. Note that the light-emitting device or the display device can be used for electronic devices and automobiles in a variety of fields without being limited to those described in this embodiment.

Note that the structures described in this embodiment can be combined with any of the structures described in the other embodiments as appropriate.

Embodiment 6

In this embodiment, a structure of a lighting device fabricated using the light-emitting device of one embodiment of the present invention or the light-emitting element which is a part of the light-emitting device is described with reference to FIGS. 7A to 7D.

Figure 7A:
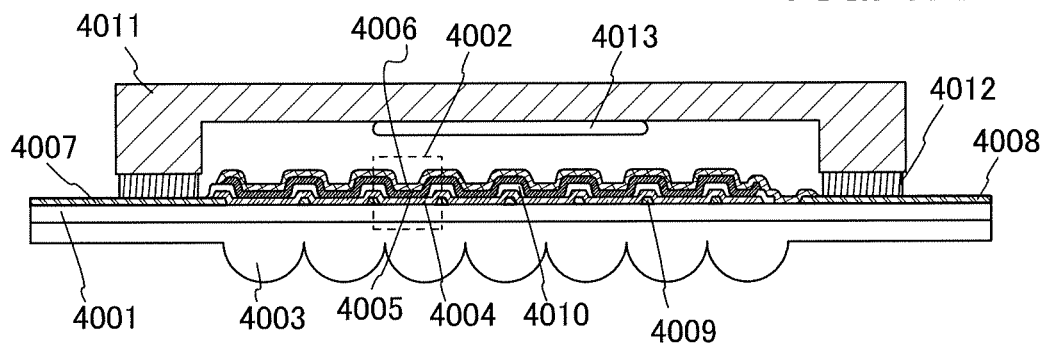
FIGS. 7A to 7D illustrate lighting devices.
Figure 7B:
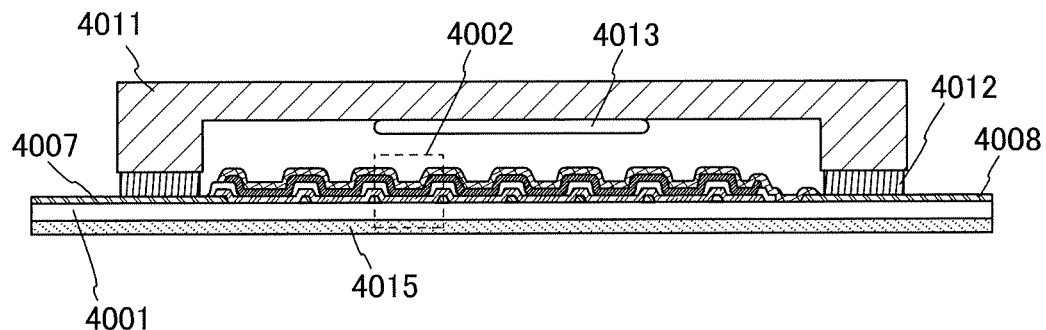
Figure 7C:
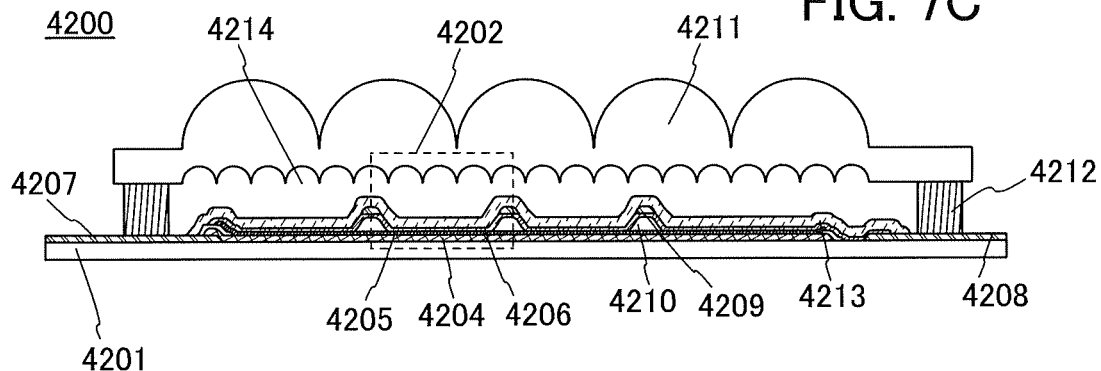
Figure 7D:
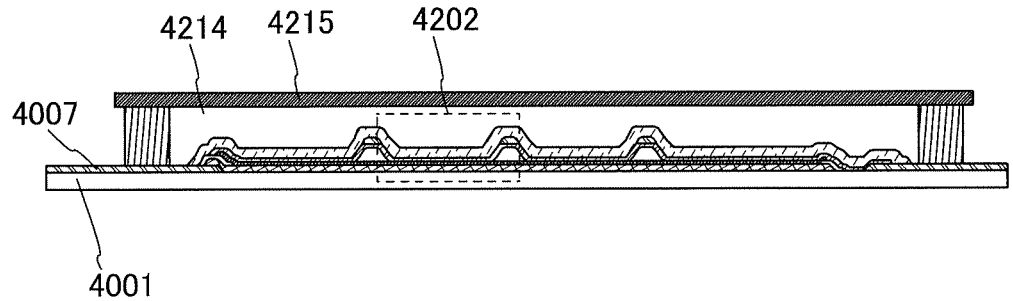

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 7D.

Note that with the use of the light-emitting device of one embodiment of the present invention or the light-emitting element which is a part of the light-emitting device as described in this embodiment, a lighting device having desired chromaticity can be provided.

Note that the structures described in this embodiment can be combined with any of the structures described in the other embodiments as appropriate.

Embodiment 7

Figure 8:
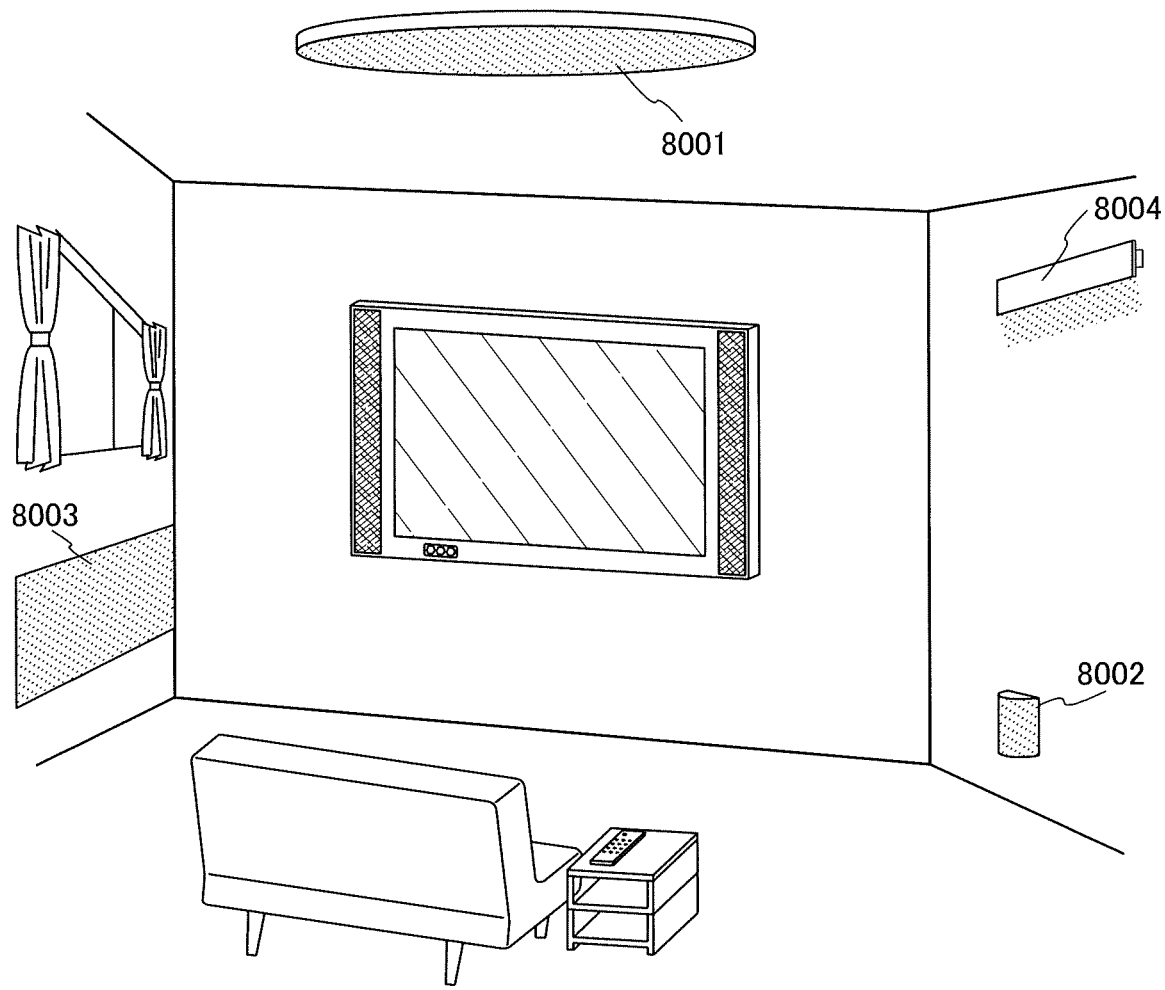
FIG. 8 illustrates lighting devices.

In this embodiment, application examples of lighting devices fabricated using the light-emitting device of one embodiment of the present invention or the light-emitting element which is a part of the light-emitting device will be described with reference to FIG. 8.

A ceiling light 8001 can be used as an indoor lighting device. Examples of the ceiling light 8001 include a direct-mount light and an embedded light. Such a lighting device is fabricated using the light-emitting device and a housing or a cover in combination. Besides, application to a cord pendant light (light that is suspended from a ceiling by a cord) is also possible.

A foot light 8002 lights a floor so that safety on the floor can be improved. For example, it can be effectively used in a bedroom, on a staircase, or on a passage. In that case, the size or shape of the foot light can be changed depending on the area or structure of a room. The foot light 8002 can be a stationary lighting device fabricated using the light-emitting device and a support base in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

In addition, a lighting device 8004 in which the direction of light from a light source is controlled to be only a desired direction can be used.

Besides the above examples, when the light-emitting device of one embodiment of the present invention or the light-emitting element which is a part of the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structures described in this embodiment can be combined with any of the structures described in the other embodiments as appropriate.

Embodiment 8

In this embodiment, touch panels including the light-emitting device of one embodiment of the present invention will be described with reference to FIGS. 9A and 9B, FIGS. 10A and 10B, FIGS. 11A and 11B, FIGS. 12A and 12B, and FIG. 13.

Figure 9A:
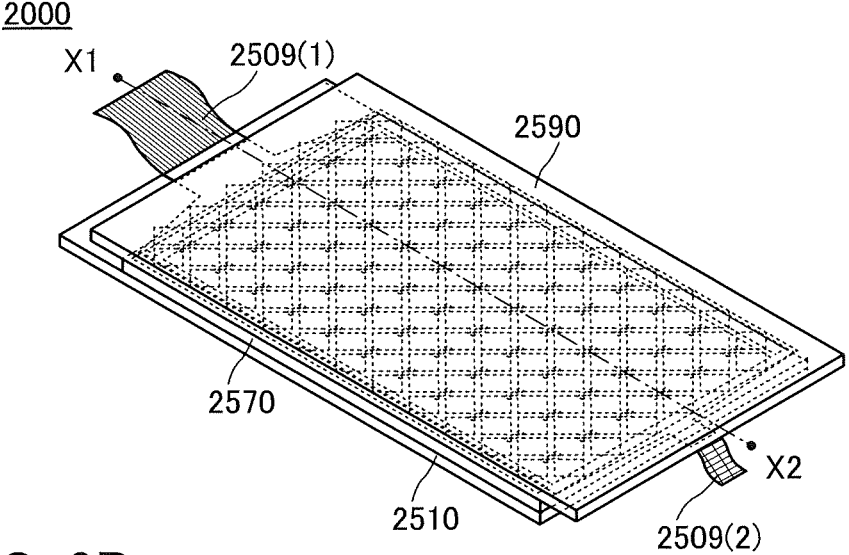
FIGS. 9A and 9B illustrate an example of a touch panel.
Figure 9B:
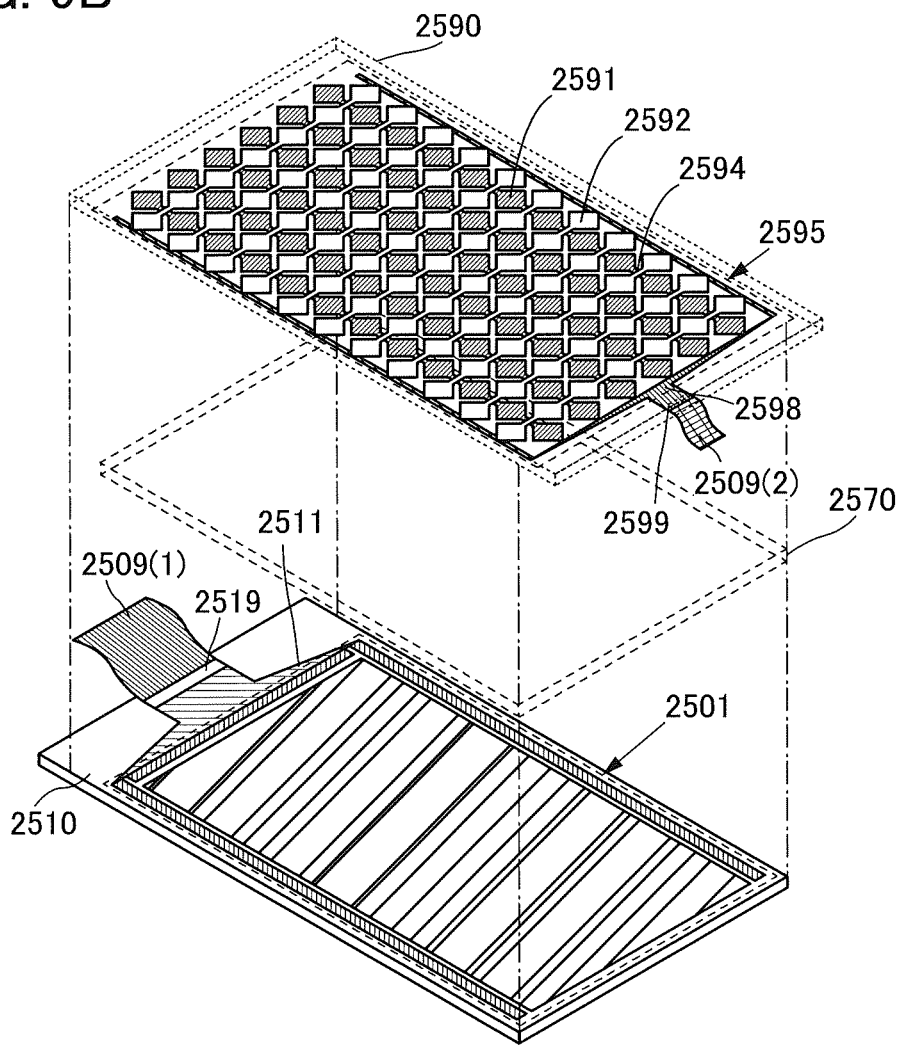

FIGS. 9A and 9B are perspective views of a touch panel 2000. Note that FIGS. 9A and 9B illustrate only main components of the touch panel 2000 for simplicity.

The touch panel 2000 includes a display panel 2501 and a touch sensor 2595 (see FIG. 9B). The touch panel 2000 includes a substrate 2510, a substrate 2570, and a substrate 2590.

The display panel 2501 includes, over the substrate 2510, a plurality of pixels and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal 2599. The terminal 2599 is electrically connected to an FPC 2509(2). Note that in FIG. 9B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor include a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive type is preferable because multiple points can be sensed simultaneously.

First, an example of using a projected capacitive touch sensor will be described below with reference to FIG. 9B. Note that in the case of a projected capacitive touch sensor, a variety of sensors that can sense proximity or touch of a sensing target such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594, as illustrated in FIGS. 9A and 9B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Note that the shapes of the electrodes 2591 and the electrodes 2592 are not limited thereto and can be any of a variety of shapes. For example, the plurality of electrodes 2591 may be provided so that a space between the electrodes 2591 is reduced as much as possible, and the plurality of electrodes 2592 may be provided with an insulating layer located between the electrodes 2591 and 2592. In this case, it is preferable to provide, between two adjacent electrodes 2592, a dummy electrode electrically insulated from these electrodes because the area of regions having different transmittances can be reduced.

Figure 10A:
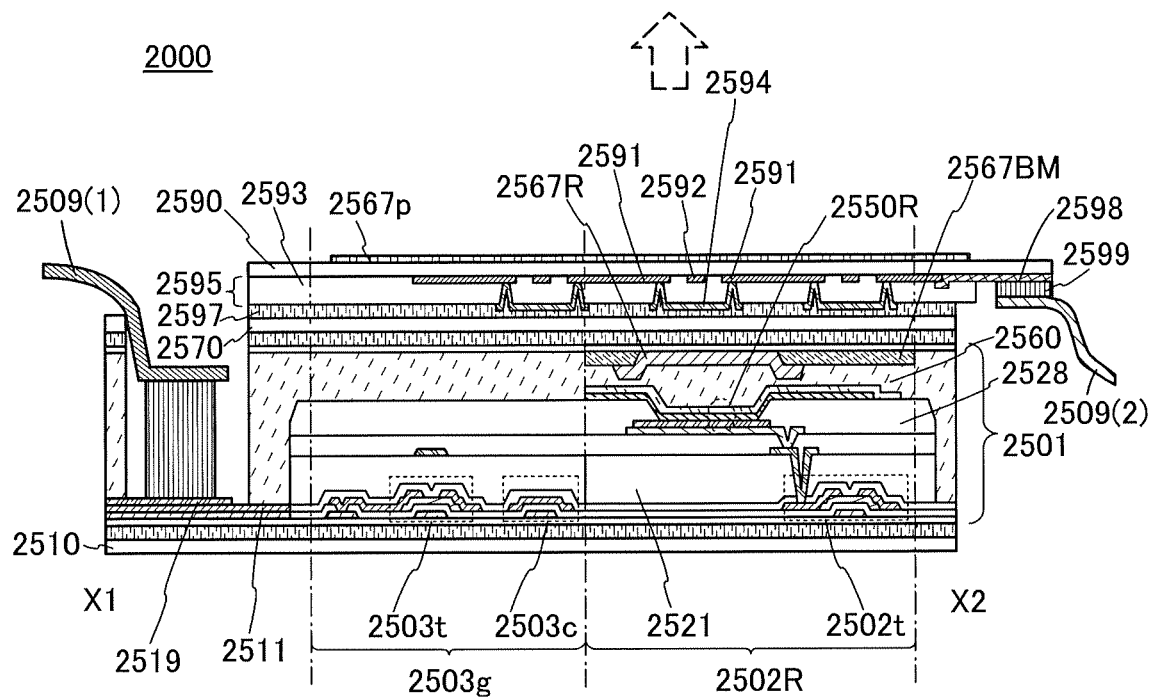
FIGS. 10A and 10B illustrate an example of a touch panel.
Figure 10B:
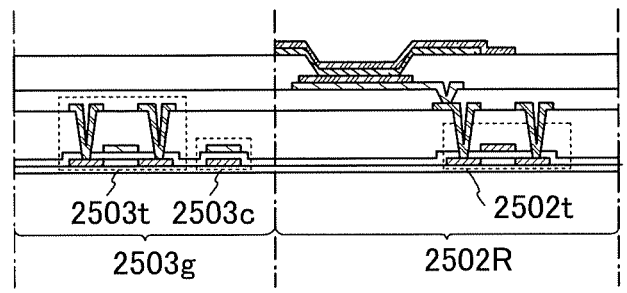

Next, the touch panel 2000 will be described in detail with reference to FIGS. 10A and 10B. FIGS. 10A and 10B correspond to cross-sectional views taken along dashed-dotted line X1-X2 in FIG. 9A.

The touch panel 2000 includes the touch sensor 2595 and the display panel 2501.

The touch sensor 2595 includes the electrodes 2591 and the electrodes 2592 provided in a staggered arrangement in contact with the substrate 2590, an insulating layer 2593 covering the electrodes 2591 and the electrodes 2592, and the wiring 2594 that electrically connects the adjacent electrodes 2591 to each other. Between the adjacent electrodes 2591, the electrode 2592 is provided.

The electrodes 2591 and the electrodes 2592 can be formed using a light-transmitting conductive material. As the light-transmitting conductive material, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 include a resin such as an acrylic resin or an epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrodes 2591 and 2592 to reduce electrical resistance.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 10A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 10A includes, between the substrate 2510 and the substrate 2570, a plurality of pixels arranged in a matrix and a driver circuit. Each pixel includes a light-emitting element and a pixel circuit that drives the light-emitting element.

In FIG. 10A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 has a function of providing a flat surface by covering unevenness caused by the transistor and the like that have been already formed. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (the scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 10A includes a bottom-gate transistor is described, the structure of the transistor is not limited thereto, and any of transistors with various structures can be used. In each of the transistors 2502t and 2503t illustrated in FIG. 10A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 10B illustrates the structure that includes a top-gate transistor instead of the bottom-gate transistor illustrated in FIG. 10A. The kind of the semiconductor layer that can be used for the channel region does not depend on the structure of the transistor.

In the touch panel 2000 illustrated in FIG. 10A, an anti-reflection layer 2567p overlapping with at least the pixel is preferably provided on a surface of the touch panel on the side from which light from the pixel is extracted, as illustrated in FIG. 10A. As the anti-reflection layer 2567p, a circular polarizing plate or the like can be used.

For the substrates 2510, 2570, and 2590 in FIG. 10A, for example, a flexible material having a vapor permeability of $1\times10^{-5}$ g/(m$^2$·day) or lower, preferably $1\times10^{-6}$ g/(m$^2$·day) or lower, can be favorably used. Alternatively, it is preferable to use the materials that make these substrates have substantially the same coefficient of thermal expansion. For example, the coefficients of linear expansion of the materials are $1\times10^{-3}$/K or lower, preferably $5\times10^{-5}$/K or lower, and further preferably $1\times10^{-5}$/K or lower.

Next, a touch panel 2000' having a structure different from that of the touch panel 2000 illustrated in FIGS. 10A and 10B will be described with reference to FIGS. 11A and 11B. It can be used as a touch panel like the touch panel 2000.

Figure 11A:
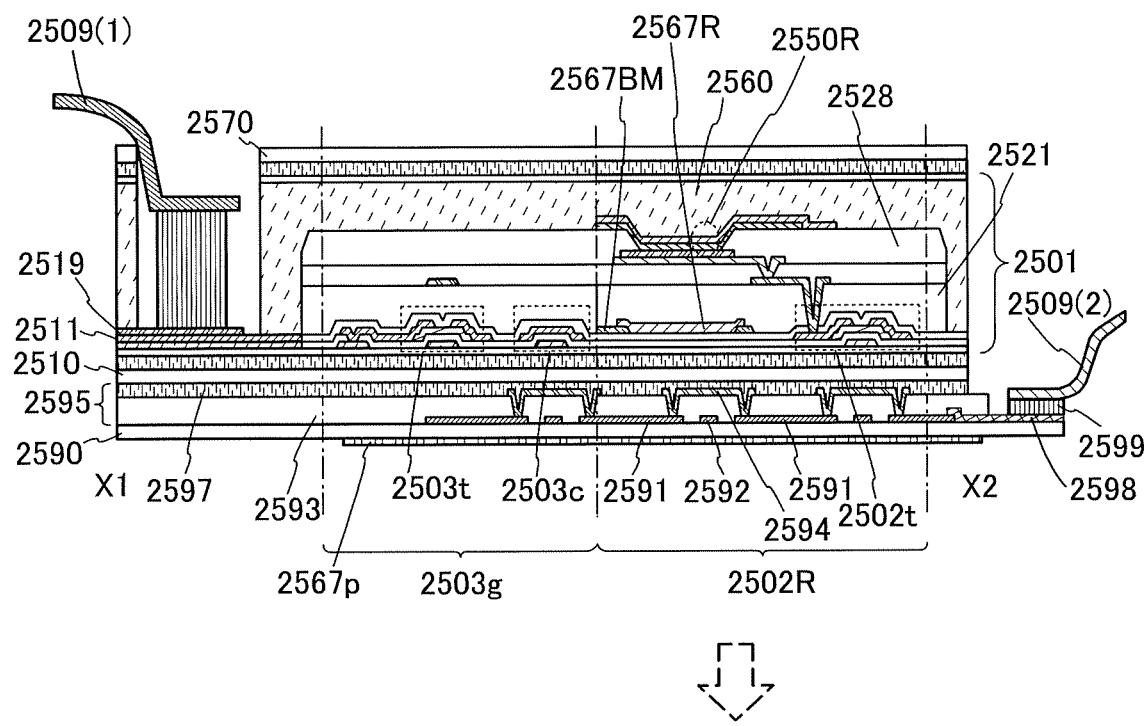
FIGS. 11A and 11B illustrate an example of a touch panel.
Figure 11B:
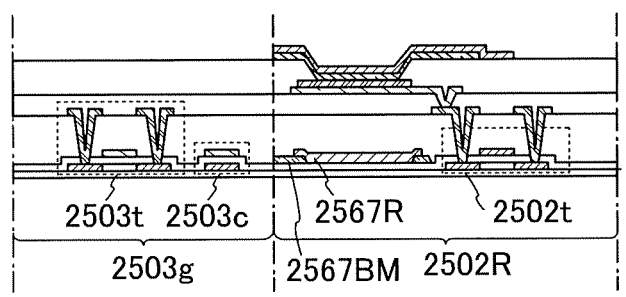

FIGS. 11A and 11B are cross-sectional views of the touch panel 2000'. In the touch panel 2000' illustrated in FIGS. 11A and 11B, the position of the touch sensor 2595 relative to the display panel 2501 is different from that in the touch panel 2000 illustrated in FIGS. 10A and 10B. Only different structures will be described below, and the above description of the touch panel 2000 can be referred to for the other similar structures.

The coloring layer 2567R overlaps with the light-emitting element 2550R. The light-emitting element 2550R illustrated in FIG. 11A emits light to the side where the transistor 2502t is provided. That is, (part of) light emitted from the light-emitting element 2550R passes through the coloring layer 2567R and is extracted in the direction indicated by an arrow in FIG. 11A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 11A).

The adhesive layer 2597 is in contact with the substrate 2510 of the display panel 2501 and attaches the display panel 2501 and the touch sensor 2595 to each other in the structure illustrated in FIG. 11A. The substrate 2510 is not necessarily provided between the display panel 2501 and the touch sensor 2595 that are attached to each other by the adhesive layer 2597.

As in the touch panel 2000, transistors with any of a variety of structures can be used for the display panel 2501 in the touch panel 2000'. Although a bottom-gate transistor is used in FIG. 11A, a top-gate transistor may be used as illustrated in FIG. 11B.

An example of a driving method of the touch panel will be described with reference to FIGS. 12A and 12B.

Figure 12A:
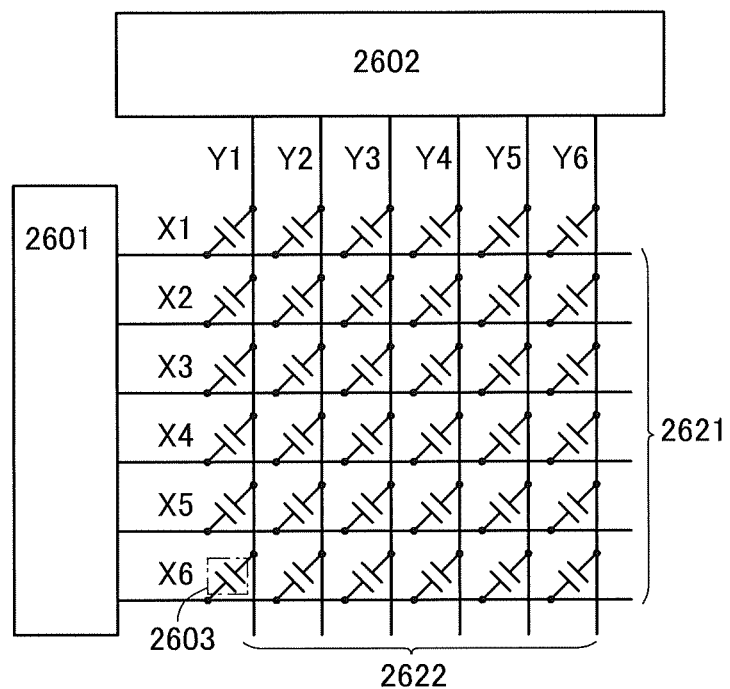
FIGS. 12A and 12B are a block diagram and a timing chart of a touch sensor.

FIG. 12A is a block diagram illustrating the structure of a mutual capacitive touch sensor. FIG. 12A illustrates a pulse voltage output circuit 2601 and a current sensing circuit 2602. Note that in FIG. 12A, six wirings X1 to X6 represent electrodes 2621 to which a pulse voltage is applied, and six wirings Y1 to Y6 represent electrodes 2622 that detect changes in current. FIG. 12A also illustrates capacitors 2603 that are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 12B:
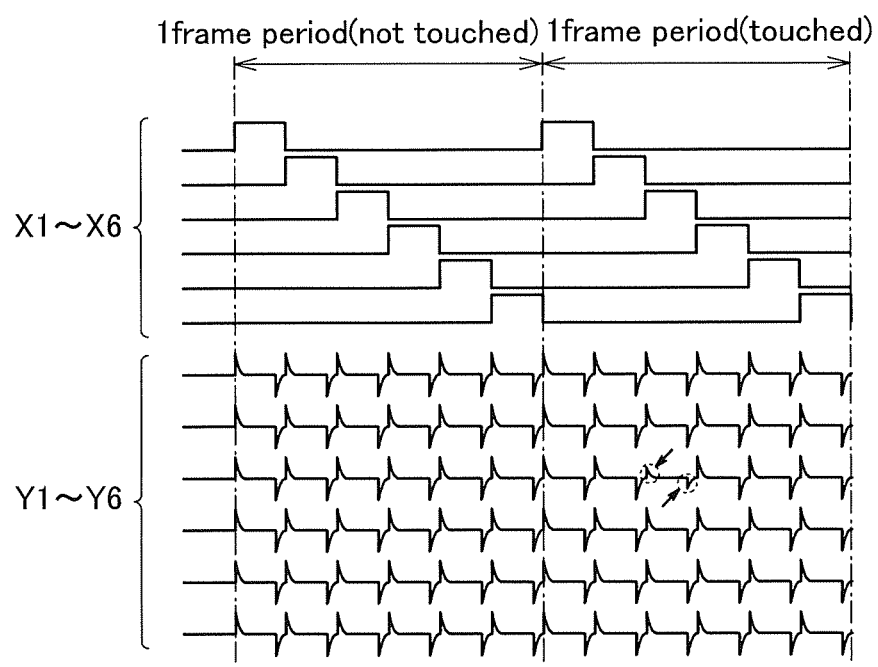

FIG. 12B is a timing chart showing input and output waveforms in the mutual capacitive touch sensor illustrated in FIG. 12A. In FIG. 12B, sensing of a sensing target is performed in all the rows and columns in one frame period. FIG. 12B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in response to the pulse voltage. When there is no approach or contact of a sensing target, the waveforms of the wirings Y1 to Y6 change uniformly in response to changes in the voltages of the wirings X1 to X6. The current value is decreased at the point of approach or contact of a sensing target and accordingly the waveform of the voltage value changes. By detecting a change in mutual capacitance in this manner, the approach or contact of a sensing target can be sensed.

Figure 13:
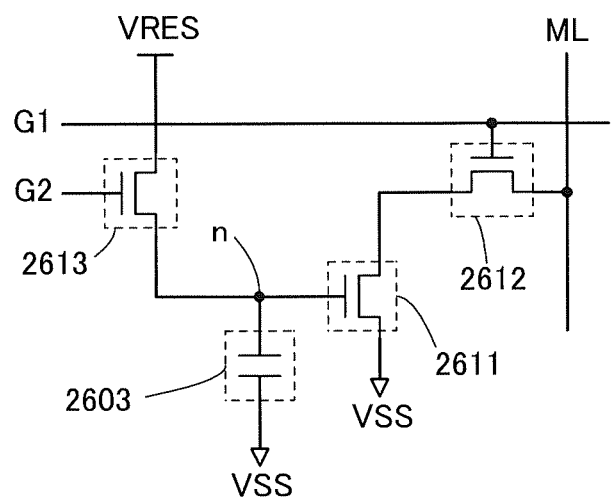
FIG. 13 is a circuit diagram of a touch sensor.

Although FIG. 12A illustrates a passive-type touch sensor in which only the capacitor 2603 is provided at the intersection of wirings as a touch sensor, an active-type touch sensor including a transistor and a capacitor may be used. FIG. 13 illustrates an example of a sensor circuit included in an active-type touch sensor.

The sensor circuit in FIG. 13 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 13 will be described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed depending on the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, it is preferable to use such a transistor as the transistor 2613 because the potential of the node n can be held for a long time and the frequency of operation of resupplying VRES to the node n (refresh operation) can be reduced.

Note that the structures described in this embodiment can be combined with any of the structures described in the other embodiments as appropriate.

Embodiment 9

In this embodiment, a display device that includes the light-emitting element of one embodiment of the present invention and a reflective liquid crystal element and that can display an image both in a transmissive mode and in a reflective mode will be described with reference to FIGS. 14A, 14B1, and 14B2, FIG. 15, and FIG. 16.

The display device described in this embodiment can be driven with extremely low power consumption for displaying an image using the reflective mode in a bright place such as outdoors. Meanwhile, in a dark place such as indoors or in a night environment, an image with a wide color gamut and high color reproducibility can be displayed with the use of the transmissive mode. Thus, by combination of these modes, the display device can display an image with low power consumption and high color reproducibility as compared with the case of a conventional display panel.

As an example of the display device of this embodiment, description will be made of a display device in which a liquid crystal element provided with a reflective electrode and a light-emitting element are stacked and an opening in the reflective electrode is provided in a position overlapping with the light-emitting element. Visible light is reflected by the reflective electrode in the reflective mode and light emitted from the light-emitting element is emitted through the opening in the reflective electrode in the transmissive mode. Note that transistors used for driving these elements (the liquid crystal element and the light-emitting element) are preferably formed on the same plane. It is preferable that the liquid crystal element and the light-emitting element be stacked with an insulating layer therebetween.

Figure 14A:
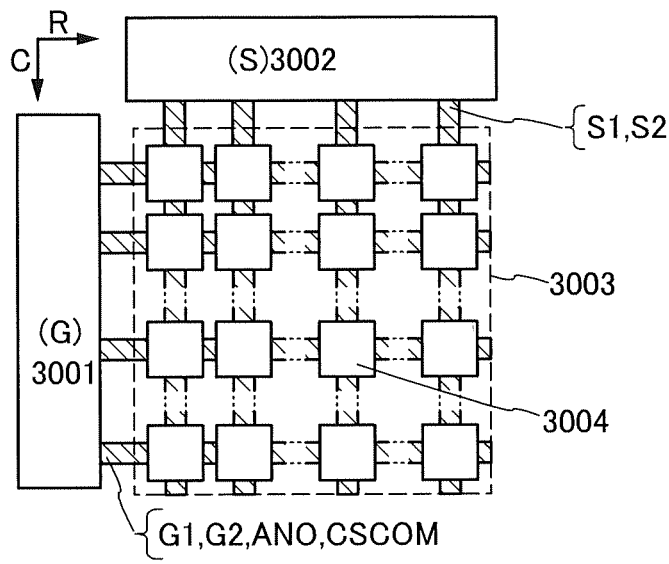
Figure 14A:
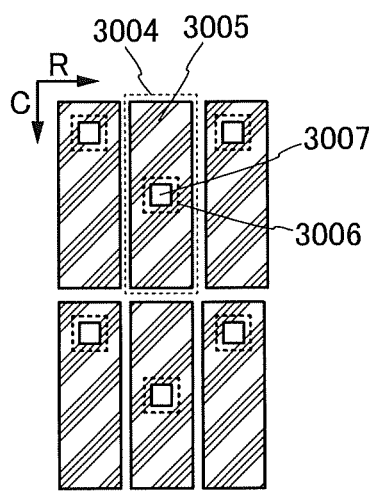
Figure 14A:
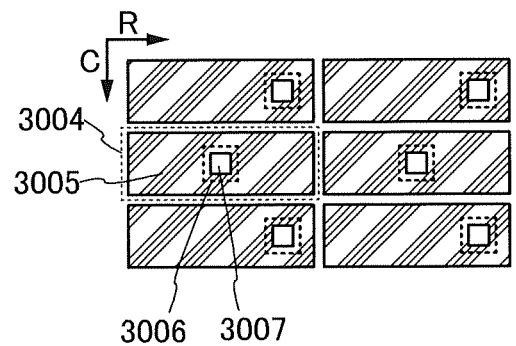

FIG. 14A is a block diagram illustrating a display device described in this embodiment. A display device 3000 includes a circuit (G) 3001, a circuit (S) 3002, and a display portion 3003. In the display portion 3003, a plurality of pixels 3004 are arranged in an R direction and a C direction in a matrix. A plurality of wirings G1, a plurality of wirings G2, a plurality of wirings ANO, and a plurality of wirings CSCOM are electrically connected to the circuit (G) 3001. These wirings are also electrically connected to the plurality of pixels 3004 arranged in the R direction. A plurality of wirings S1 and a plurality of wirings S2 are electrically connected to the circuit (S) 3002, and these wirings are also electrically connected to the plurality of pixels 3004 arranged in the C direction.

Each of the plurality of pixels 3004 includes a liquid crystal element and a light-emitting element. The liquid crystal element and the light-emitting element include portions overlapping with each other.

FIG. 14B1 shows the shape of a conductive film 3005 serving as a reflective electrode of the liquid crystal element included in the pixel 3004. Note that an opening 3007 is provided in a position 3006 which is part of the conductive film 3005 and which overlaps with the light-emitting element. That is, light emitted from the light-emitting element is emitted through the opening 3007.

The pixels 3004 in FIG. 14B1 are arranged such that the adjacent pixels 3004 in the R direction exhibit different colors. Furthermore, the openings 3007 are provided so as not to be arranged in a line in the R direction. Such arrangement has an effect of suppressing crosstalk between the light-emitting elements of adjacent pixels 3004. Furthermore, there is an advantage that element formation is facilitated owing to a reduction in the degree of miniaturization.

The opening 3007 can have a polygonal shape, a quadrangular shape, an elliptical shape, a circular shape, a cross shape, a stripe shape, or a slit-like shape, for example.

FIG. 14B2 illustrates another example of the arrangement of the conductive films 3005.

The ratio of the opening 3007 to the total area of the conductive film 3005 (excluding the opening 3007) affects the display of the display device. That is, a problem is caused in that as the area of the opening 3007 is larger, the display using the liquid crystal element becomes darker; in contrast, as the area of the opening 3007 is smaller, the display using the light-emitting element becomes darker. Furthermore, in addition to the problem of the ratio of the opening, a small area of the opening 3007 itself also causes a problem in that extraction efficiency of light emitted from the light-emitting element is decreased. The ratio of the opening 3007 to the total area of the conductive film 3005 (excluding the opening 3007) is preferably 5% or more and 60% or less because the display quality can be maintained even when the liquid crystal element and the light-emitting element are used in a combination.

Figure 15:
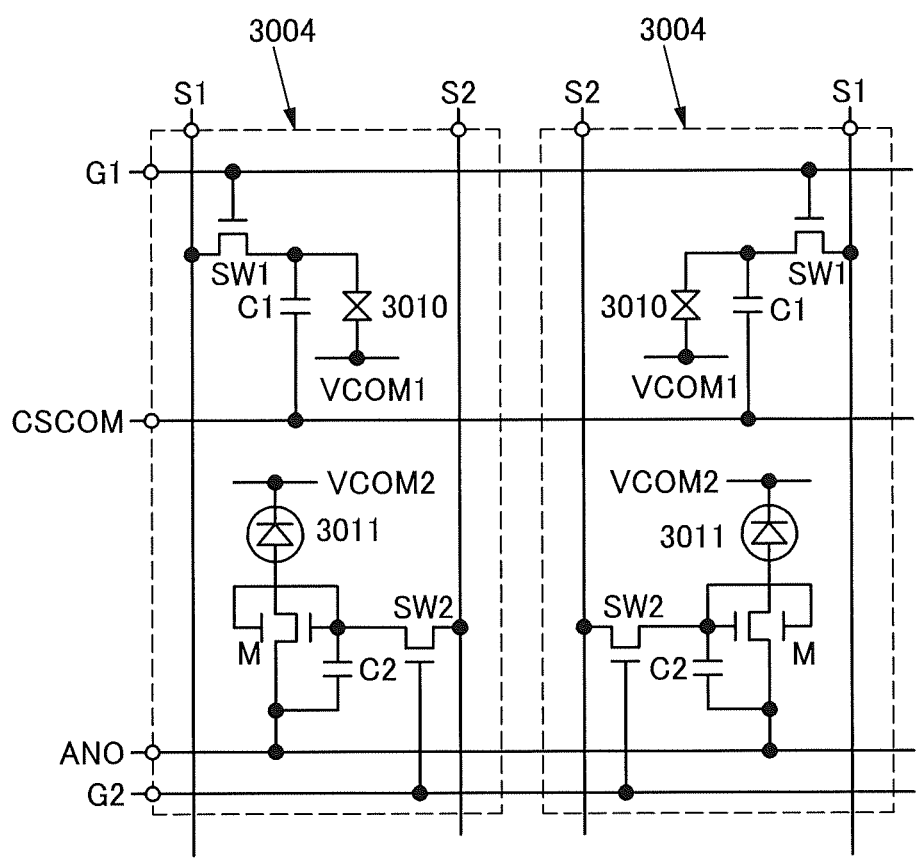
FIG. 15 illustrates a circuit configuration of a display device.

Next, an example of a circuit configuration of the pixel 3004 is described with reference to FIG. 15. FIG. 15 illustrates two adjacent pixels 3004.

The pixel 3004 includes a transistor SW1, a capacitor C1, a liquid crystal element 3010, a transistor SW2, a transistor M, a capacitor C2, a light-emitting element 3011, and the like. Note that these components are electrically connected to any of the wiring G1, the wiring G2, the wiring ANO, the wiring CSCOM, the wiring S1, and the wiring S2 in the pixel 3004. The liquid crystal element 3010 and the light-emitting element 3011 are electrically connected to a wiring VCOM1 and a wiring VCOM2, respectively.

A gate of the transistor SW1 is connected to the wiring G1. One of a source and a drain of the transistor SW1 is connected to the wiring Si, and the other of the source and the drain is connected to one electrode of the capacitor C1 and one electrode of the liquid crystal element 3010. The other electrode of the capacitor C1 is connected to the wiring CSCOM. The other electrode of the liquid crystal element 3010 is connected to the wiring VCOM1.

A gate of the transistor SW2 is connected to the wiring G2. One of a source and a drain of the transistor SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 3011. Furthermore, the other electrode of the light-emitting element 3011 is connected to the wiring VCOM2.

Note that the transistor M includes two gates between which a semiconductor is provided and which are electrically connected to each other. With such a structure, the amount of current flowing through the transistor M can be increased.

The on/off state of the transistor SW1 is controlled by a signal from the wiring G1. A predetermined potential is applied from the wiring VCOM1. Furthermore, orientation of liquid crystals of the liquid crystal element 3010 can be controlled by a signal from the wiring S1. A predetermined potential is applied from the wiring CSCOM.

The on/off state of the transistor SW2 is controlled by a signal from the wiring G2. By the difference between the potentials applied from the wiring VCOM2 and the wiring ANO, the light-emitting element 3011 can emit light. Furthermore, the conduction state of the transistor M can be controlled by a signal from the wiring S2.

Accordingly, in the structure of this embodiment, in the case of the reflective mode, the liquid crystal element 3010 is controlled by the signals supplied from the wiring G1 and the wiring Si and optical modulation is utilized, whereby an image can be displayed. In the case of the transmissive mode, the light-emitting element 3011 can emit light when the signals are supplied from the wiring G2 and the wiring S2. In the case where both modes are performed at the same time, desired driving can be performed on the basis of the signals from the wiring G1, the wiring G2, the wiring S1, and the wiring S2.

Figure 16:
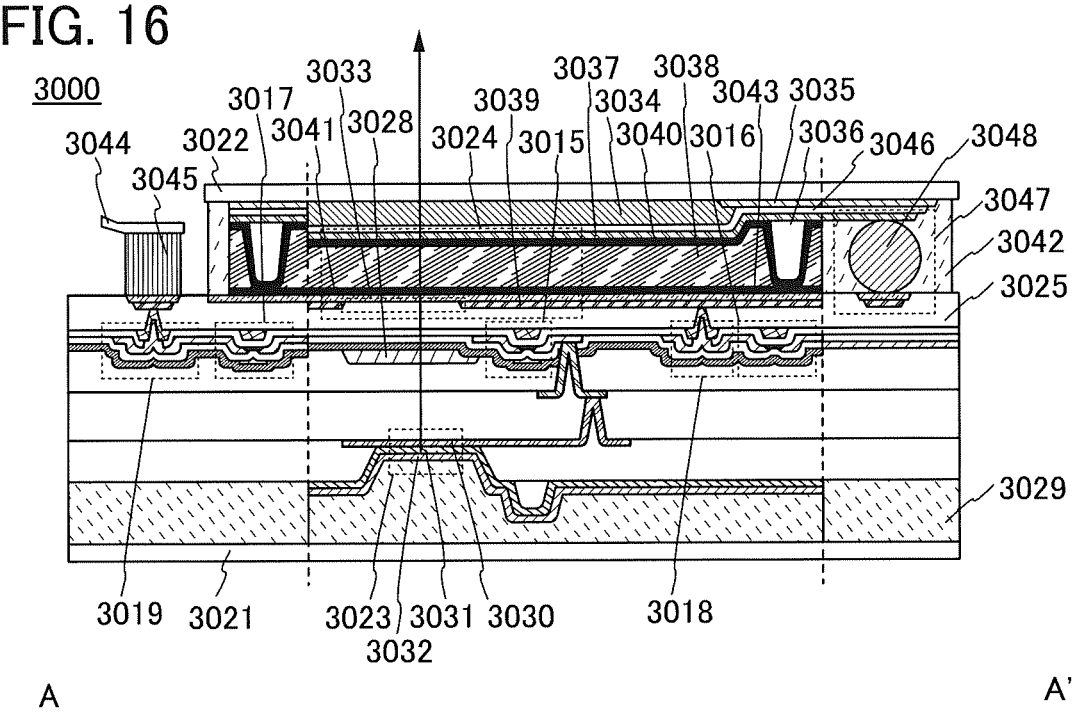
FIG. 16 illustrates a cross-sectional structure of a display device.

Next, specific description will be given with reference to FIG. 16, a schematic cross-sectional view of the display device 3000 described in this embodiment.

The display device 3000 includes a light-emitting element 3023 and a liquid crystal element 3024 between substrates 3021 and 3022. Note that the light-emitting element 3023 and the liquid crystal element 3024 are formed with an insulating layer 3025 positioned therebetween. That is, the light-emitting element 3023 is positioned between the substrate 3021 and the insulating layer 3025, and the liquid crystal element 3024 is positioned between the substrate 3022 and the insulating layer 3025.

A transistor 3015, a transistor 3016, a transistor 3017, a coloring layer 3028, and the like are provided between the insulating layer 3025 and the light-emitting element 3023.

A bonding layer 3029 is provided between the substrate 3021 and the light-emitting element 3023. The light-emitting element 3023 includes a conductive layer 3030 serving as one electrode, an EL layer 3031, and a conductive layer 3032 serving as the other electrode which are stacked in this order over the insulating layer 3025. In the light-emitting element 3023 that is a bottom emission light-emitting element, the conductive layer 3032 and the conductive layer 3030 contain a material that reflects visible light and a material that transmits visible light, respectively. Light emitted from the light-emitting element 3023 is transmitted through the coloring layer 3028 and the insulating layer 3025 and then transmitted through the liquid crystal element 3024 via an opening 3033, thereby being emitted to the outside of the substrate 3022.

In addition to the liquid crystal element 3024, a coloring layer 3034, a light-blocking layer 3035, an insulating layer 3046, a structure 3036, and the like are provided between the insulating layer 3025 and the substrate 3022. The liquid crystal element 3024 includes a conductive layer 3037 serving as one electrode, a liquid crystal 3038, a conductive layer 3039 serving as the other electrode, alignment films 3040 and 3041, and the like. Note that the liquid crystal element 3024 is a reflective liquid crystal element and the conductive layer 3039 serves as a reflective electrode; thus, the conductive layer 3039 is formed using a material with high reflectivity. Furthermore, the conductive layer 3037 serves as a transparent electrode, and thus is formed using a material that transmits visible light. The alignment films 3040 and 3041 are provided on the conductive layers 3037 and 3039 and in contact with the liquid crystal 3038. The insulating layer 3046 is provided so as to cover the coloring layer 3034 and the light-blocking layer 3035 and serves as an overcoat. Note that the alignment films 3040 and 3041 are not necessarily provided.

The opening 3033 is provided in part of the conductive layer 3039. A conductive layer 3043 is provided in contact with the conductive layer 3039. Since the conductive layer 3043 has a light-transmitting property, a material transmitting visible light is used for the conductive layer 3043.

The structure 3036 serves as a spacer that prevents the substrate 3022 from coming closer to the insulating layer 3025 than required. The structure 3036 is not necessarily provided.

One of a source and a drain of the transistor 3015 is electrically connected to the conductive layer 3030 in the light-emitting element 3023. For example, the transistor 3015 corresponds to the transistor M in FIG. 15.

One of a source and a drain of the transistor 3016 is electrically connected to the conductive layer 3039 and the conductive layer 3043 in the liquid crystal element 3024 through a terminal portion 3018. That is, the terminal portion 3018 has a function of electrically connecting the conductive layers provided on both surfaces of the insulating layer 3025. The transistor 3016 corresponds to the transistor SW1 in FIG. 15.

A terminal portion 3019 is provided in a region where the substrates 3021 and 3022 do not overlap with each other. The terminal portion 3019 electrically connects the conductive layers provided on both surfaces of the insulating layer 3025 like the terminal portion 3018. The terminal portion 3019 is electrically connected to a conductive layer obtained by processing the same conductive film as the conductive layer 3043. Thus, the terminal portion 3019 and an FPC 3044 can be electrically connected to each other through a connection layer 3045.

A connection portion 3047 is provided in part of a region where a bonding layer 3042 is provided. In the connection portion 3047, the conductive layer obtained by processing the same conductive film as the conductive layer 3043 and part of the conductive layer 3037 are electrically connected with a connector 3048. Accordingly, a signal or a potential input from the FPC 3044 can be supplied to the conductive layer 3037 through the connector 3048.

The structure 3036 is provided between the conductive layer 3037 and the conductive layer 3043. The structure 3036 has a function of maintaining a cell gap of the liquid crystal element 3024.

As the conductive layer 3043, a metal oxide, a metal nitride, or an oxide such as an oxide semiconductor whose resistance is reduced is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive layer 3043.

Note that the structures described in this embodiment can be combined with any of the structures described in the other embodiments as appropriate.

Example 1

Synthesis Example 1

In this example is described a method for synthesizing the organic compound of one embodiment of the present invention, 2-{3-[3-(benzo[b]naphtho[1,2-d]furan-8-yl)phenyl]phenyl}-4,6-diphenyl-1,3,5-triazine (abbreviation: mBnfBPTzn), which is represented by Structural Formula (100) in Embodiment 1. A structure of mBnfBPTzn is shown below.

[Chemical Formula 24]

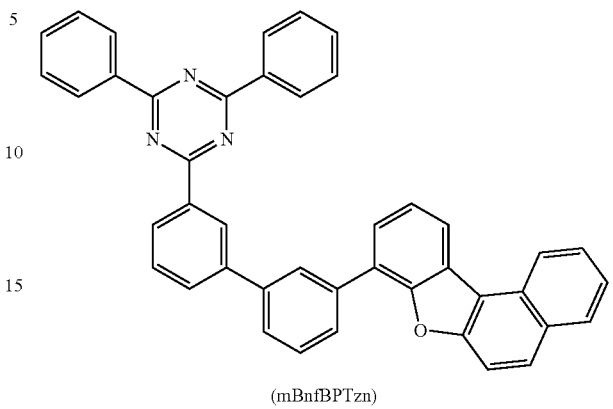

(100)

(mBnfBPTzn)

Step 1: Synthesis of
1-(3-chloro-2-fluorophenyl)-2-naphthol

Into a 200 mL three-neck flask were put 3.4 g (19 mmol) of 3-chloro-2-fluorophenylboronic acid, 4.0 g (18 mmol) of 1-bromo-2-naphthol, 0.13 g (0.36 mmol) of di(1-adamantyl)-n-butylphosphine, and 7.6 g (72 mmol) of sodium carbonate, and the atmosphere in the flask was replaced with nitrogen. To the mixture were added 90 mL of toluene and 36 mL of water, and the resulting mixture was degassed by being stirred while the pressure was reduced. After the degasification, 40 mg (0.18 mmol) of palladium(II) acetate was added to the mixture, and the resulting mixture was stirred at approximately 80° C. for 15 hours. After the stirring, the aqueous layer of this mixture was subjected to extraction with toluene, and the solution of the obtained extract and the organic layer were combined and washed with a saturated aqueous solution of sodium chloride. The obtained organic layer was dried with magnesium sulfate. This mixture was gravity-filtered, and the obtained filtrate was concentrated to give a brown oily substance. This oily substance was purified by silica gel column chromatography (using a developing solvent of toluene) to give 4.5 g of a target brown oily substance in a yield of 91%. The synthesis scheme of Step 1 is shown in (a-1) below.

[Chemical Formula 25]

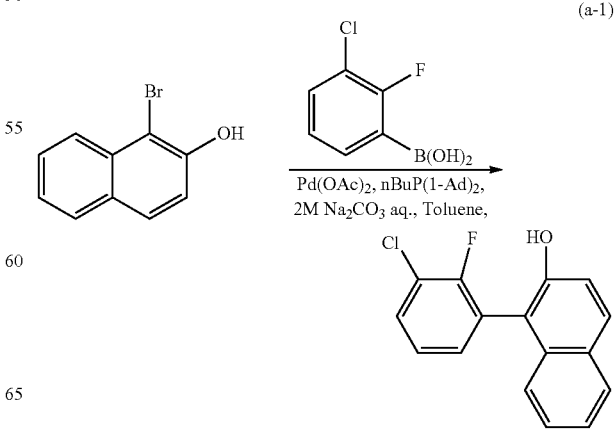

(a-1)

Step 2: Synthesis of 8-chlorobenzo[b]naphtho[1,2-d]furan

Next, 4.5 g (16 mmol) of 1-(3-chloro-2-fluorophenyl)-2-naphthol, 80 mL of N-methyl-2-pyrrolidone (NMP), and 4.4 g (32 mmol) of potassium carbonate were put into a 500 mL three-neck flask. This flask was subjected to stirring at 150° C. for 2 hours under a nitrogen stream. After the stirring, this mixture was cooled down to room temperature and added to approximately 200 mL of toluene, and approximately 100 mL of water was added to the mixture. The aqueous layer of the mixture was subjected to extraction with toluene, and the solution of the extract and the organic layer were combined and washed with dilute hydrochloric acid (1.0 mol/L) and a saturated aqueous solution of sodium chloride. The organic layer was dried with magnesium sulfate, and after the drying, this mixture was gravity-filtered. The obtained filtrate was concentrated to give an oily substance. The obtained oily substance was dissolved in approximately 50 mL of toluene, and this solution was subjected to suction filtration through Celite, alumina, and Florisil. A solid obtained by concentrating the resulting filtrate was recrystallized from toluene/hexane to give 3.2 g of target white needle-like crystals in a yield of 79%. The synthesis scheme of Step 2 is shown in (a-2) below.

[Chemical Formula 26]

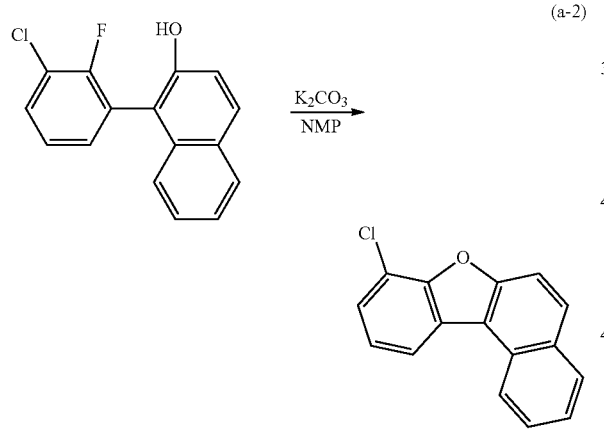

(a-2)

Step 3: Synthesis of 4,4,5,5-tetramethyl-2-(benzo[b]naphtho[1,2-d]furan-8-yl)-1,3,2-dioxaborolane Next, 2.5 g (10 mmol) of 8-chlorobenzo[b]naphtho[1,2-d]furan, 3.0 g (12 mmol) of bis(pinacolato)diboron, 72 mg (0.20 mmol) of di(1-adamantyl)-n-butylphosphine, and 3.0 g (30 mmol) of potassium acetate were put into a 200 mL three-neck flask, and the atmosphere in the flask was replaced with nitrogen. To this mixture was added 50 mL of xylene, and the resulting mixture was degassed by being stirred while the pressure was reduced. To this mixture was added 82 mg (0.10 mmol) of [1,1'-bis(diphenylphosphino)ferrocene]palladium(II) dichloride dichloromethane adduct, and the resulting mixture was stirred at 130° C. for 4 hours under a nitrogen stream. After the stirring, this mixture was suction-filtered, and the obtained filtrate was concentrated to give an oily substance. The obtained oily substance was purified by silica gel column chromatography (using a developing solvent of hexane:toluene=9:1) to give a solid. The obtained solid was washed with hexane to give 2.0 g of a target white solid in a yield of 59%. The synthesis scheme of Step 3 is shown in (a-3) below.

[Chemical Formula 27]

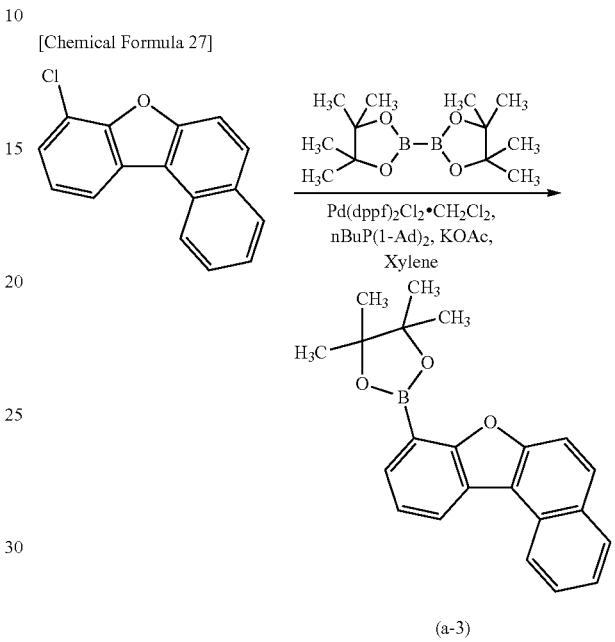

(a-3)

Step 4: Synthesis of 2-(3-chlorophenyl)-4,6-diphenyl-1,3,5-triazine

Into a 200 mL three-neck flask were added 10 g (37 mmol) of 2-chloro-4,6-diphenyl-1,3,5-triazine, 5.8 g (37 mmol) of 3-chlorophenylboronic acid, and 7.8 g (74 mmol) of sodium carbonate, and the atmosphere in the flask was replaced with nitrogen. To the mixture were added 150 mL of toluene, 35 mL of ethanol, and 37 mL of water, and the resulting mixture was degassed by being stirred while the pressure was reduced. After the degasification, 0.43 g (0.37 mmol) of tetrakis(triphenylphosphine)palladium(0) was added to the mixture, and the resulting mixture was stirred at approximately 80° C. for 3 hours. After the stirring, the aqueous layer of this mixture was subjected to extraction with toluene, and the solution of the obtained extract and the organic layer were combined and washed with a saturated aqueous solution of sodium chloride. The obtained organic layer was dried with magnesium sulfate. This mixture was gravity-filtered, and the obtained filtrate was concentrated to give a solid. The obtained solid was dissolved in approximately 30 mL of hot toluene, and this solution was subjected to suction filtration through Celite, alumina, and Florisil. A solid obtained by concentration of the obtained filtrate was washed with methanol, and the solid was collected by suction filtration to give 11 g of a target white solid in a yield of 86%. The synthesis scheme of Step 4 is shown in (a-4) below.

[Chemical Formula 28]

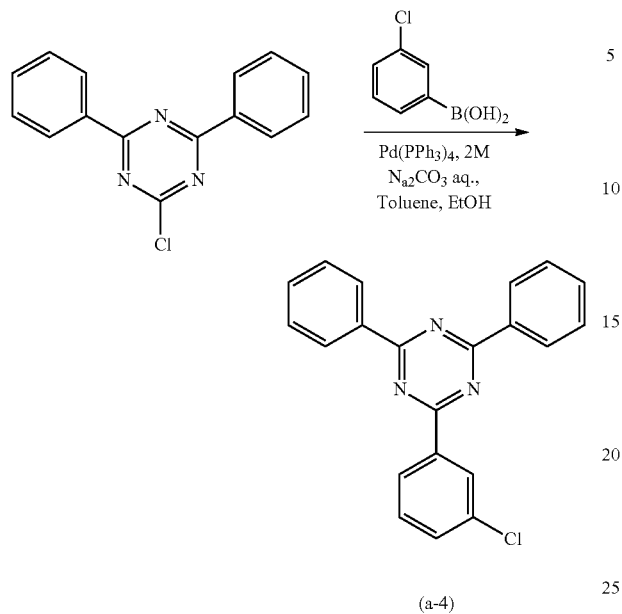

(a-4)

Step 5: Synthesis of 4,4,5,5-tetramethyl-2-[3-(4,6-diphenyl-1,3,5-triazin-2-yl)phenyl]-1,3,2-dioxaborolane Into a 200 mL three-neck flask were put 5.0 g (15 mmol) of 2-(3-chlorophenyl)-4,6-diphenyl-1,3,5-triazine, 4.1 g (16 mmol) of bis(pinacolato)diboron, 0.21 g (0.60 mmol) of di(1-adamantyl)-n-butylphosphine, and 4.4 g (45 mmol) of potassium acetate, and the atmosphere in the flask was replaced with nitrogen. To this mixture was added 74 mL of xylene, and the resulting mixture was degassed by being stirred while the pressure was reduced. To this mixture heated to 40° C. was added 0.12 g (0.15 mmol) of [1,1'-bis(diphenylphosphino)ferrocene]palladium(II) dichloride dichloromethane adduct, and the resulting mixture was stirred at 130° C. for 24 hours under a nitrogen stream. After the stirring, this mixture was suction-filtered, and the obtained filtrate was concentrated to give an oily substance. The obtained oily substance was purified by silica gel column chromatography (using a developing solvent of hexane:toluene=6:1) to give a white solid. The obtained solid was washed with hexane to give 3.4 g of a target white solid in a yield of 53%. The synthesis scheme of Step 5 is shown in (a-5) below.

[Chemical Fomula 29]

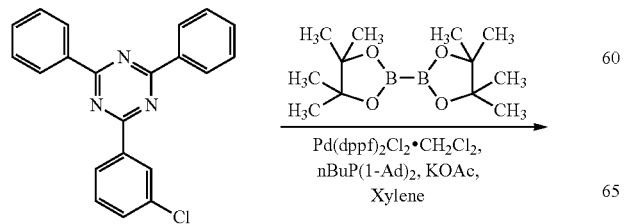

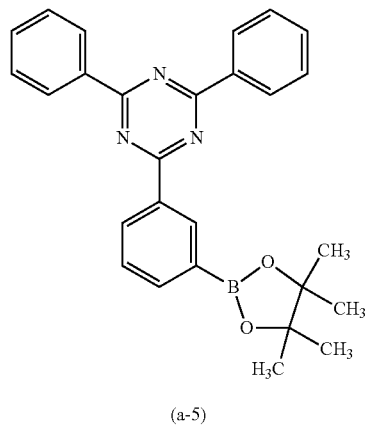

(a-5)

Step 6: Synthesis of 2-[3-(3-chlorophenyl)phenyl]-4,6-diphenyl-1,3,5-triazine

Into a 200 mL three-neck flask were added 3.0 g (6.9 mmol) of 4,4,5,5-tetramethyl-2-[3-(4,6-diphenyl-1,3,5-triazin-2-yl)phenyl]-1,3,2-dioxaborolane, 2.4 g (10 mmol) of 3-chloroiodobenzene, 43 mg (0.14 mmol) of tri(o-tolyl)phosphine, and 1.9 g (14 mmol) of potassium carbonate, and the atmosphere in the flask was replaced with nitrogen. To the mixture were added 25 mL of toluene, 10 mL of ethanol, and 7.0 mL of water, and the resulting mixture was degassed by being stirred while the pressure was reduced. After the degasification, 16 mg (0.070 mmol) of palladium(II) acetate was added to the mixture heated at 40° C., and the resulting mixture was stirred at approximately 80° C. for 7 hours, whereby a solid was precipitated. The precipitated solid was collected by suction filtration and dissolved in approximately 30 mL of hot toluene, and this solution was subjected to suction filtration through Celite, alumina, and Florisil. A solid obtained by concentration of the obtained filtrate was recrystallized from toluene to give 2.2 g of a target white solid in a yield of 77%. The synthesis scheme of Step 6 is shown in (a-6) below.

[Chemical Formula 30]

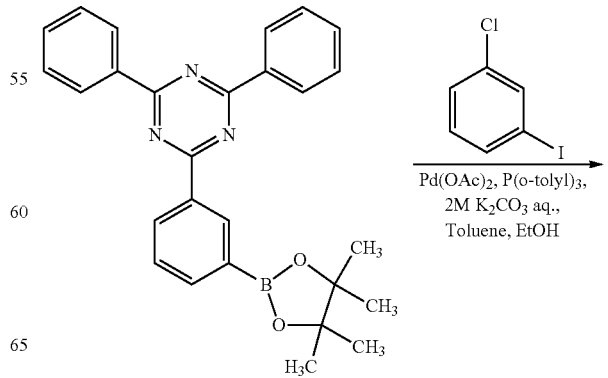

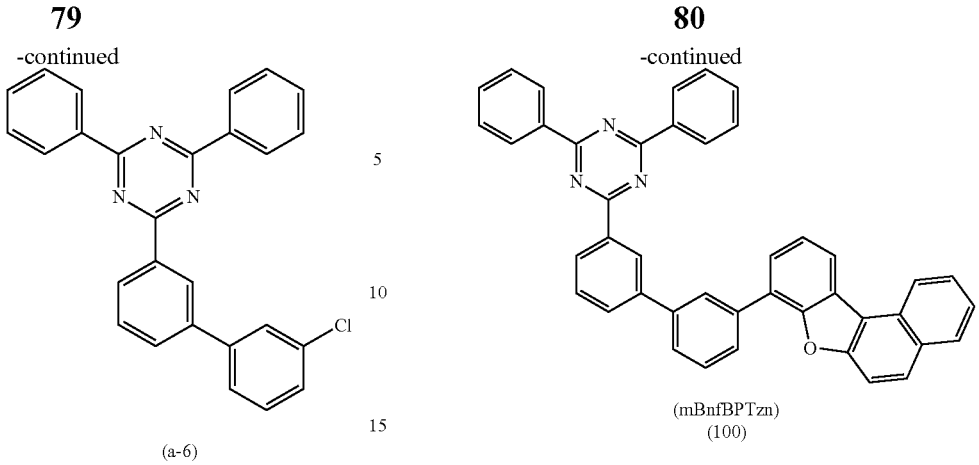

(a-6)

Step 7: Synthesis of 2-{3-[3-(benzo[b]naphtho[1,2-d]furan-8-yl)phenyl]phenyl}-4,6-diphenyl-1,3,5-triazine Into a 200 mL three-neck flask were added 2.1 g (5.0 mmol) of 2-[3-(3-chlorophenyl)phenyl]-4,6-diphenyl-1,3,5-triazine, 1.7 g (5.0 mmol) of 4,4,5,5-tetramethyl-2-(benzo[b]naphtho[1,2-d]furan-8-yl)-1,3,2-dioxaborolane, 3.2 g (15 mmol) of tripotassium phosphate, and 36 mg (0.10 mmol) of di(1-adamantyl)-n-butylphosphine, and the atmosphere in the flask was replaced with nitrogen.

To this mixture, 25 mL of diethylene glycol dimethyl ether and 1.2 g (15 mmol) of tert-butyl alcohol were added. The resulting mixture was degassed by being stirred while the pressure was reduced. To this mixture was added 12 mg (0.050 mmol) of palladium(II) acetate, and the resulting mixture was stirred at 80° C. for 7 hours under a nitrogen stream, whereby a solid was precipitated.

After the stirring, water was added to the mixture, and the resulting mixture was stirred and suction-filtered to collect a solid. The collected solid was dissolved in approximately 500 mL of hot toluene, and this solution was subjected to suction filtration through Celite, alumina, and Florisil. A solid obtained by concentration of the obtained filtrate was recrystallized from toluene to give 1.8 g of a target white powder in a yield of 58%. The synthesis scheme of Step 7 is shown in (a-7) below.

[Chemical Formula 31]

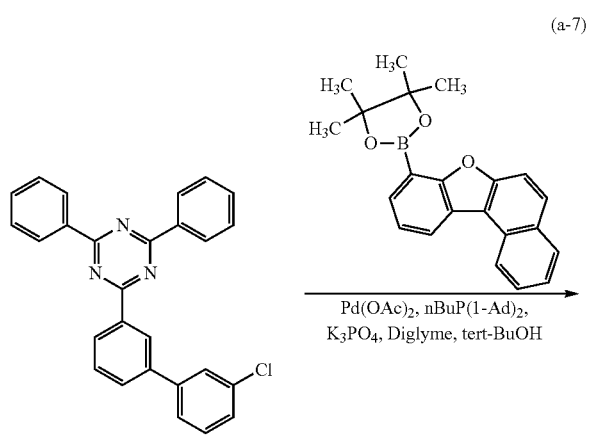

(a-7)

By a train sublimation method, 1.7 g of the obtained white powder was purified under a pressure of 0.018 Pa at 280° C. After the sublimation purification, 0.76 g of a white solid of mBnfBPTzn was obtained at a collection rate of 44%.

Figure 17:
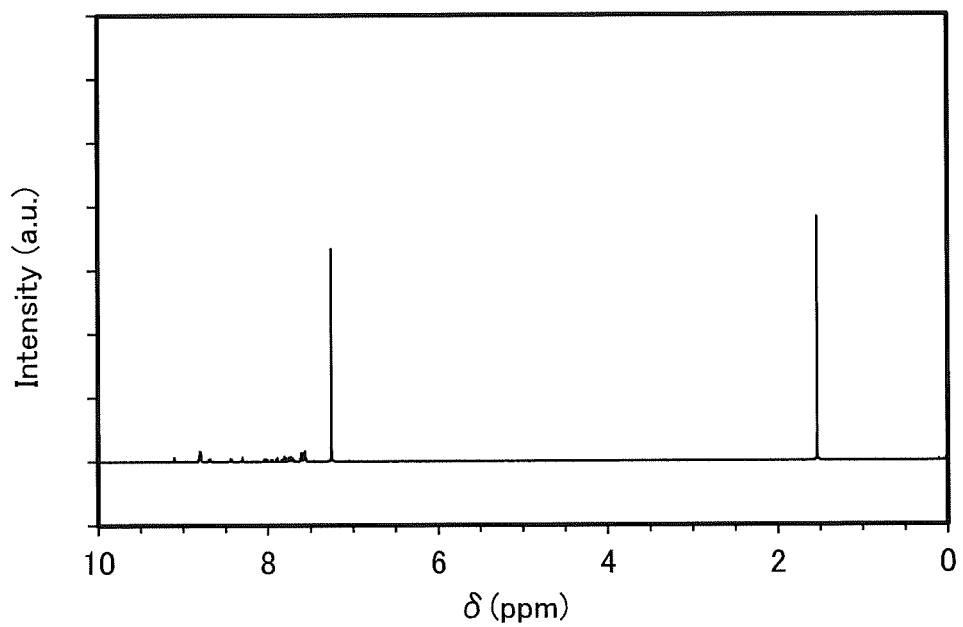
FIG. 17 shows a $^1$H-NMR chart of an organic compound represented by Structural Formula (100).

Analysis results by nuclear magnetic resonance ($^1$H-NMR) spectroscopy of the white solid obtained by Step 7 are shown below. FIG. 17 shows the $^1$H-NMR chart. These results reveal that the organic compound of one embodiment of the present invention, mBnfBPTzn represented by Structural Formula (100), was obtained in this example.

$^1$H NMR (CDCl$_3$, 500 MHz): δ=7.56-7.64 (m, 8H), 7.79-7.85 (m, 6H), 7.90 (d, J=9.0 Hz, 1H), 7.96 (d, J=8.5 Hz, 1H), 8.01-8.05 (m, 2H), 8.31 (s, 1H), 8.45 (d, J=8.5 Hz, 1H), 8.70 (d, J=8.0 Hz, 1H), 8.80-8.83 (m, 5H), 9.11 (s, 1H).

Figure 18A:
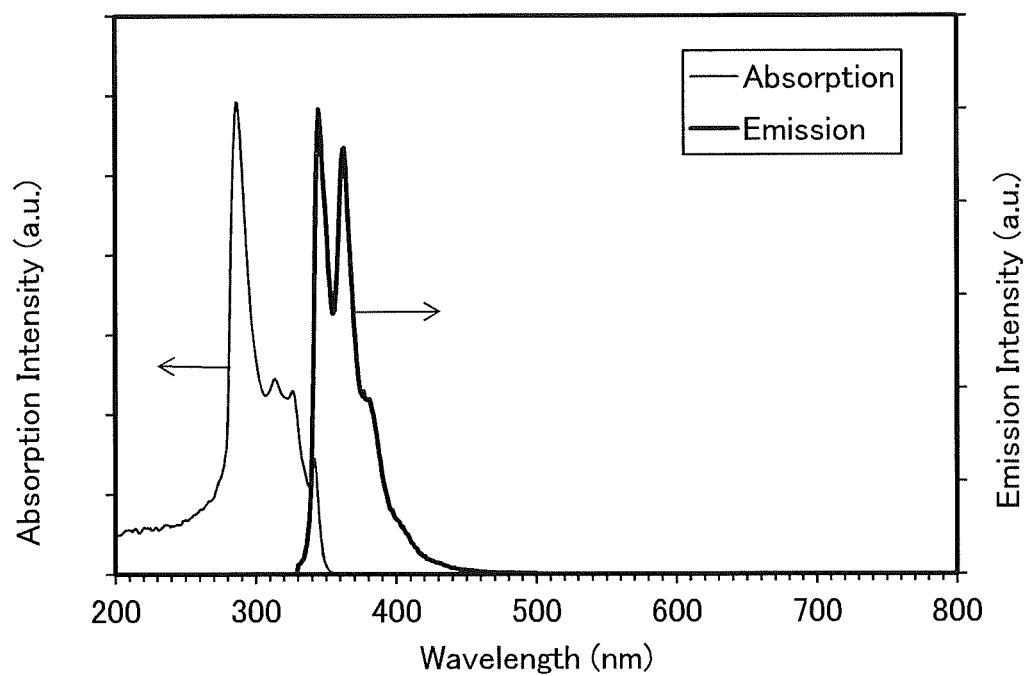
FIGS. 18A and 18B each show an ultraviolet-visible absorption spectrum and an emission spectrum of the organic compound represented by Structural Formula (100).
Figure 18B:
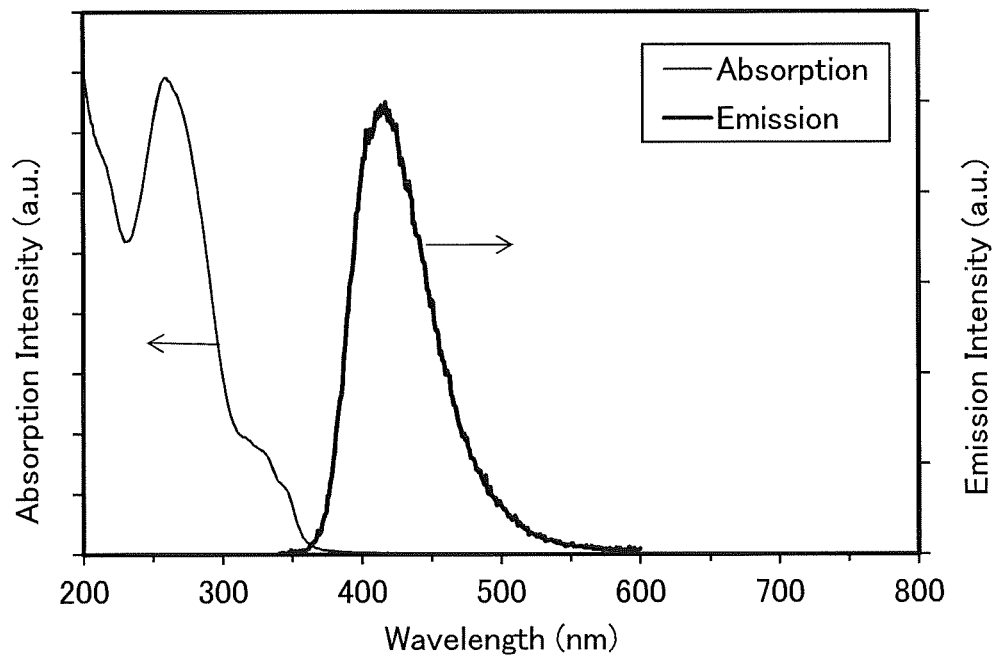

Next, ultraviolet-visible absorption spectra (hereinafter, simply referred to as "absorption spectra") of mBnfBPTzn in a toluene solution and that in a solid thin film and emission spectra thereof were measured. The solid thin film was formed over a quartz substrate by a vacuum evaporation method. The absorption spectra were measured using ultraviolet-visible spectrophotometers (V-550 manufactured by JASCO Corporation for the solution and U-4100 manufactured by Hitachi, Ltd. for the thin film). Note that the absorption spectrum in the solution was calculated by subtraction of the measured absorption spectrum of only toluene in a quartz cell, and the absorption spectrum in the thin film was calculated using an absorbance (−log$_{10}$ [% T/(100−% R)]) obtained from a transmittance and a reflectance of a substrate and the thin film. Note that % T represents transmittance and % R represents reflectance. The emission spectra were measured using a fluorescence spectrophotometer (FS920 manufactured by Hamamatsu Photonics K.K.). Measurement results of the obtained absorption and emission spectra in the toluene solution are shown in FIG. 18A, in which the horizontal axis represents wavelength and the vertical axes represent absorption intensity and emission intensity. Measurement results of the absorption and emission spectra in the solid thin film are shown in FIG. 18B, in which the horizontal axis represents wavelength and the vertical axes represent absorption intensity and emission intensity.

FIG. 18A shows that mBnfBPTzn in the toluene solution has absorption peaks at around 284 nm, 314 nm, 327 nm, and 342 nm, and emission wavelength peaks at 348 nm, 362 nm, and 379 nm. FIG. 18B shows that mBnfBPTzn in the solid thin film has absorption peaks at around 217 nm, 260 nm, 316 nm, 330 nm, and 347 nm, and an emission wavelength peak at 416 nm (an excitation wavelength of 330 nm).

The ionization potential of mBnfBPTzn in the thin film state was measured in the air with a photoelectron spectrometer (AC-3 manufactured by Riken Keiki Co., Ltd.). The obtained value was converted into a negative value, so that the HOMO level of mBnfBPTzn was −6.17 eV. From the data of the absorption spectrum in the thin film in FIG. 18B, the absorption edge of mBnfBPTzn, which was obtained from Tauc plot with an assumption of direct transition, was 3.49 eV. Thus, the optical energy gap of mBnfBPTzn in the solid state can be estimated to be 3.49 eV; from the values of the HOMO level obtained above and this energy gap, the LUMO level of mBnfBPTzn can be estimated to be −2.68 eV. This reveals that mBnfBPTzn in the solid state has an energy gap as wide as 3.49 eV.

Next, mBnfBPTzn obtained in this example was subjected to an analysis by liquid chromatography-mass spectrometry (LC-MS). In the LC-MS analysis, liquid chromatography (LC) separation was carried out with UltiMate 3000 manufactured by Thermo Fisher Scientific K.K., and mass spectrometry (MS) was carried out with Q Exactive manufactured by Thermo Fisher Scientific K.K. In the LC separation, a given column was used at a column temperature of 40° C., and solution sending was performed in such a manner that an appropriate solvent was selected, the sample was prepared by dissolving mBnfBPTzn in an organic solvent at an arbitrary concentration, and the injection amount was 5.0 μL. In the MS analysis, ionization was carried out by an electrospray ionization (ESI) method, and measurement was carried out using Full MS-SIM. The Full MS-SIM measurement was carried out in a mass range of m/z=150 to m/z=2000, and detection was performed in a positive mode. The obtained MS spectrum is shown in FIG. 19.

Figure 19:
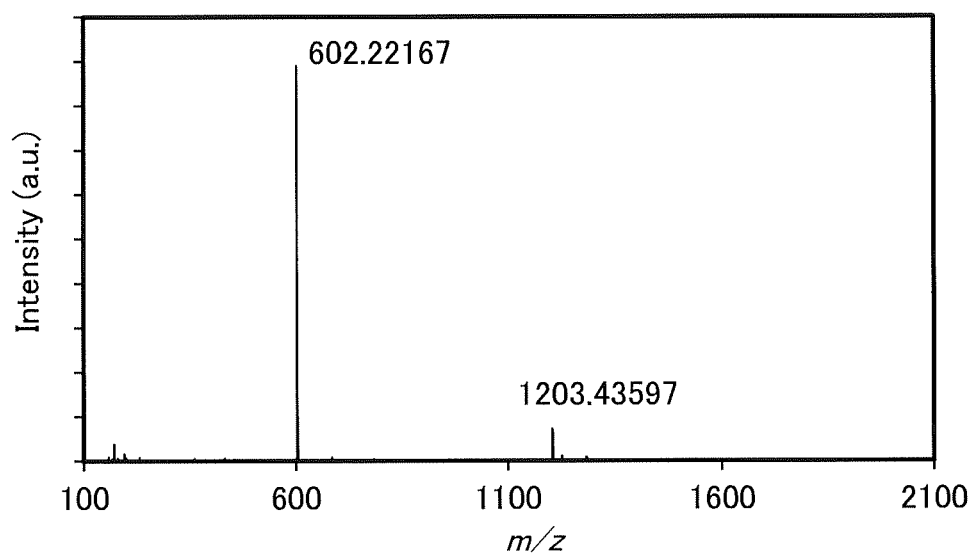
FIG. 19 shows an MS spectrum of the organic compound represented by Structural Formula (100).

The results in FIG. 19 show m/z=602, which corresponds to the sum of the exact mass of mBnfBPTzn and the mass of a proton. This confirms that mBnfBPTzn was obtained.

Thermogravimetry-differential thermal analysis (TG-DTA) of mBnfBPTzn was performed. A high vacuum differential type differential thermal balance (TG/DTA 2410SA, manufactured by Bruker AXS K.K.) was used for the measurement. The measurement was carried out under a nitrogen stream (a flow rate of 200 mL/min) and a normal pressure at a temperature rising rate of 10° C./min. From the relationship between weight and temperature (thermogravimetry), it has been found that mBnfBPTzn has a 5% weight-loss temperature of 462° C., which is indicative of high heat resistance of mBnfBPTzn.

Differential scanning calorimetry (DSC) was also performed on mBnfBPTzn. For the calorimetry, Pyris 1 DSC manufactured by PerkinElmer, Inc. was used. In the differential scanning calorimetry, after the temperature was raised from −10° C. to 300° C. at a temperature rising rate of 40° C./min, the temperature was held for a minute and then lowered to −10° C. at a temperature decreasing rate of 40° C./min. This operation was the first measurement. Then, the same operation with the temperature rising and decreasing rates changed to 10° C./min was performed as the second measurement, and the second measurement result was employed. The DSC measurement shows that the glass transition point of mBnfBPTzn is 97° C. In addition, the measurement was also performed on 2-{3-[3-(dibenzothiophen-4-yl)phenyl]phenyl}-4,6-diphenyl-1,3,5-triazine (abbreviation: mDBtBPTzn). The measurement shows that the glass transition point of mDBtBPTzn is 81° C. and is lower than that of mBnfBPTzn. This reveals that mBnfBPTzn has higher heat resistance than mDBtBPTzn.

Example 2

Synthesis Example 2

In this example is described a method for synthesizing the organic compound of one embodiment of the present invention, 2-{3-[3-(benzo[b]naphtho[1,2-d]furan-6-yl)phenyl]phenyl}-4,6-diphenyl-1,3,5-triazine (abbreviation: mBnfBPTzn-02), which is represented by Structural Formula (121) in Embodiment 1. A structure of mBnfBPTzn-02 is shown below.

[Chemical Formula 32]

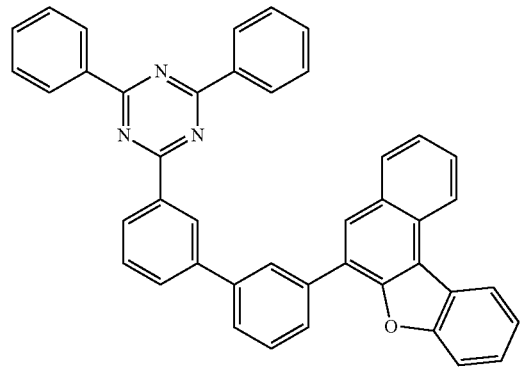

(121)

(mBnfBPTzn-02)

Into a 200 mL three-neck flask were added 0.54 g (1.3 mmol) of 2-[3-(3-chlorophenyl)phenyl]-4,6-diphenyl-1,3,5-triazine, 0.36 g (1.4 mmol) of (benzo[b]naphtho[1,2-d]furan-6-yl)boronic acid, 0.85 g (4.0 mmol) of tripotassium phosphate, and 47 mg (0.13 mmol) of di(1-adamantyl)-n-butylphosphine, and the atmosphere in the flask was replaced with nitrogen. To this mixture, 7.0 mL of diethylene glycol dimethyl ether and 0.30 g (4.0 mmol) of tert-butyl alcohol were added. The resulting mixture was degassed by being stirred while the pressure was reduced. To this mixture was added 15 mg (0.065 mmol) of palladium(II) acetate, and the resulting mixture was stirred at 160° C. for 7 hours under a nitrogen stream.

After the stirring, toluene and water were added to the mixture, and the resulting mixture was stirred. Then, the aqueous layer of the mixture was subjected to extraction with toluene. The solution of the obtained extract and the organic layer were combined and washed with a saturated aqueous solution of sodium chloride. The obtained organic layer was dried with magnesium sulfate. This mixture was gravity-filtered, and the obtained filtrate was concentrated to give a black oily substance. The oily substance was purified by silica gel column chromatography (using a developing solvent of toluene:hexane=5:1) to give a solid. The obtained solid was purified by HPLC and washed with hexane to give 0.19 g of a target white solid in a yield of 24%.

By a train sublimation method, 0.19 g of the obtained white solid was purified under a pressure of 3.4 Pa at 280° C. After the sublimation purification, 0.15 g of a white solid of mBnfBPTzn-02 was obtained at a collection rate of 79%. The synthesis scheme of the above synthesis method is shown in (b-1) below.

[Chemical Formula 33]

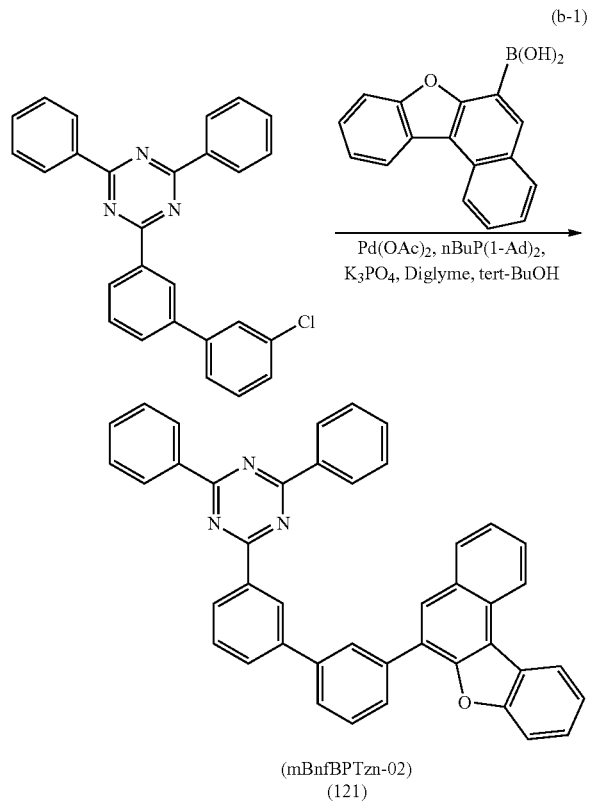

Figure 20A:
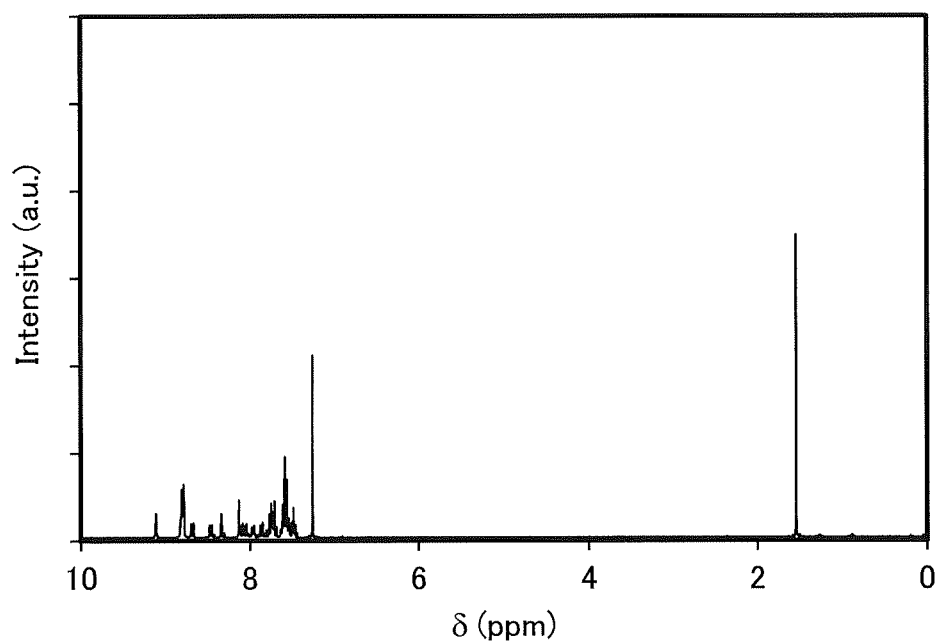
FIGS. 20A and 20B show a $^1$H-NMR chart of an organic compound represented by Structural Formula (121).
Figure 20B:
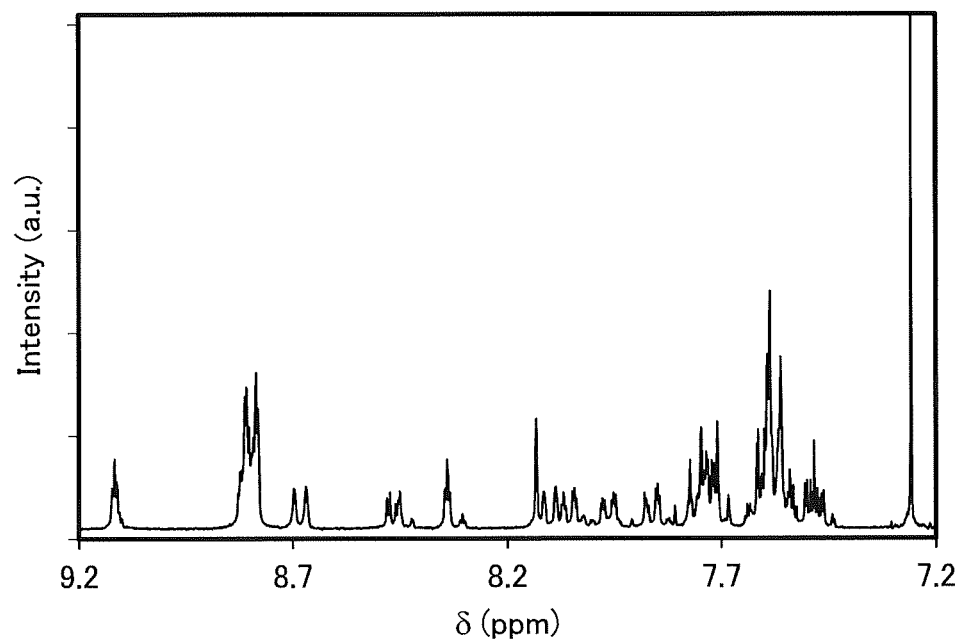

Analysis results by nuclear magnetic resonance ($^1$H-NMR) spectroscopy of the white solid obtained by the above synthesis method are shown below. FIGS. 20A and 20B show the $^1$H-NMR chart. Note that FIG. 20B is a chart where the range of from 7.20 ppm to 9.20 ppm in FIG. 20A is enlarged. These results reveal that the organic compound of one embodiment of the present invention, mBnfBPTzn-02 represented by Structural Formula (121), was obtained in this example.

$^1$H NMR (CDCl$_3$, 300 MHz): δ=7.44-7.64 (m, 9H), 7.68-7.82 (m, 4H), 7.84-8.07 (m, 3H), 8.10 (d, J=8.4 Hz, 1H), 8.13 (s, 1H), 8.34 (t, d=1.5 Hz, 1H), 8.47 (dd, J$_1$=5.7 Hz, J$_2$=1.8 Hz, 1H), 8.68 (d, J=8.1 Hz, 1H), 8.78-8.82 (m, 5H), 9.12 (t, d=2.1 Hz, 1H).

Next, an ultraviolet-visible absorption spectrum (hereinafter, simply referred to as "absorption spectrum") of mBnfBPTzn-02 in a toluene solution and an emission spectrum thereof were measured. The absorption spectrum was measured using an ultraviolet-visible spectrophotometer (V-550 manufactured by JASCO Corporation). Note that the absorption spectrum in the solution was calculated by subtraction of the measured absorption spectrum of only toluene in a quartz cell. The emission spectrum was measured using a fluorescence spectrophotometer (FS920 manufactured by Hamamatsu Photonics K.K.). Measurement results of the obtained absorption and emission spectra in the toluene solution are shown in FIG. 21, in which the horizontal axis represents wavelength and the vertical axes represent absorption intensity and emission intensity.

Figure 21:
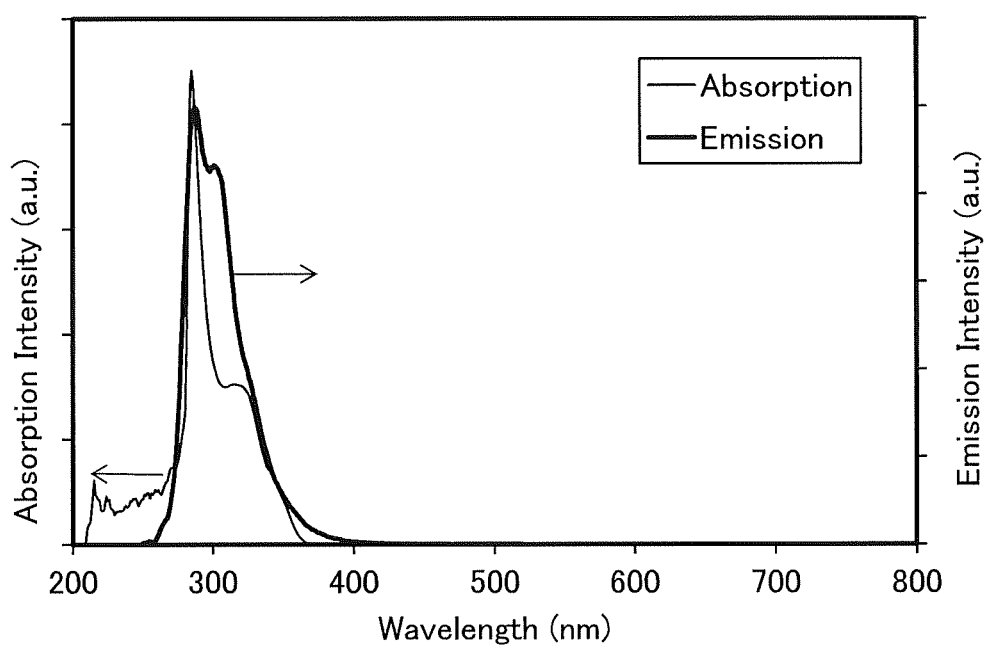
FIG. 21 shows an ultraviolet-visible absorption spectrum and an emission spectrum of the organic compound represented by Structural Formula (121).

FIG. 21 shows that mBnfBPTzn-02 in the toluene solution has absorption peaks at around 285 nm, 317 nm, and 342 nm, and emission wavelength peaks at 368 nm and 381 nm.

Thermogravimetry-differential thermal analysis (TG-DTA) of mBnfBPTzn-02 was performed. The measurement was carried out under a nitrogen stream (a flow rate of 200 mL/min) and a normal pressure at a temperature rising rate of 10° C./min. From the relationship between weight and temperature (thermogravimetry), it has been found that rBnfBPTzn-02 has a 5% weight-loss temperature of 444° C., which is indicative of high heat resistance of mBnfBPTzn-02.

Differential scanning calorimetry (DSC) was also performed on mBnfBPTzn-02 using Pyris 1 DSC manufactured by PerkinElmer, Inc. In the differential scanning calorimetry, after the temperature was raised from −10° C. to 300° C. at a temperature rising rate of 40° C./min, the temperature was held for a minute and then lowered to −10° C. at a temperature decreasing rate of 40° C./min. This operation was the first measurement. The same operation with the temperature rising and decreasing rates changed to 10° C./min was performed as the second measurement, and the second measurement result was employed. The DSC measurement shows that the glass transition point of mBnfBPTzn-02 is 111° C. In contrast, the glass transition point of mDBtBPTzn is 81° C. and is lower than that of mBnfBPTzn-02. This reveals that mBnfBPTzn-02 has higher heat resistance than mDBtBPTzn.

Example 3

Figure 22:
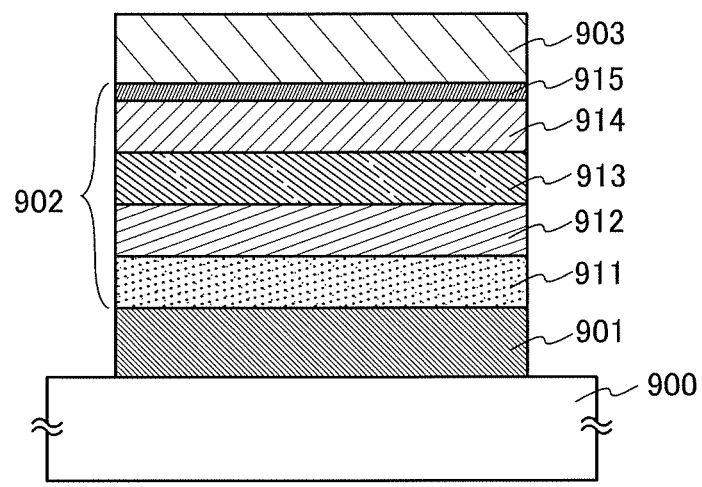
FIG. 22 illustrates a light-emitting element.
Figure 23:
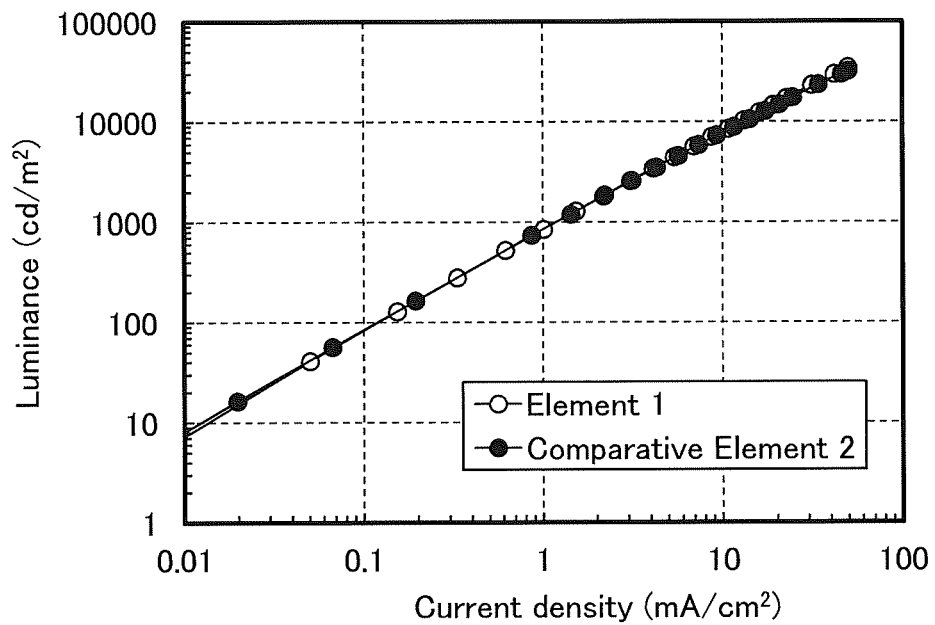
FIG. 23 shows current density-luminance characteristics of a light-emitting element 1 and a comparative light-emitting element 2.
Figure 24:
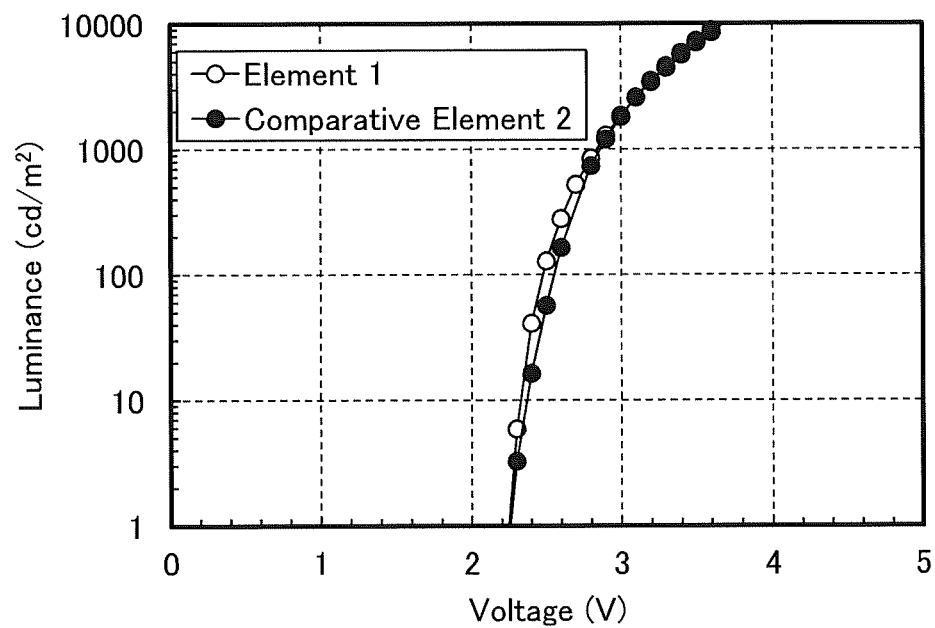
FIG. 24 shows voltage-luminance characteristics of the light-emitting element 1 and the comparative light-emitting element 2.
Figure 25:
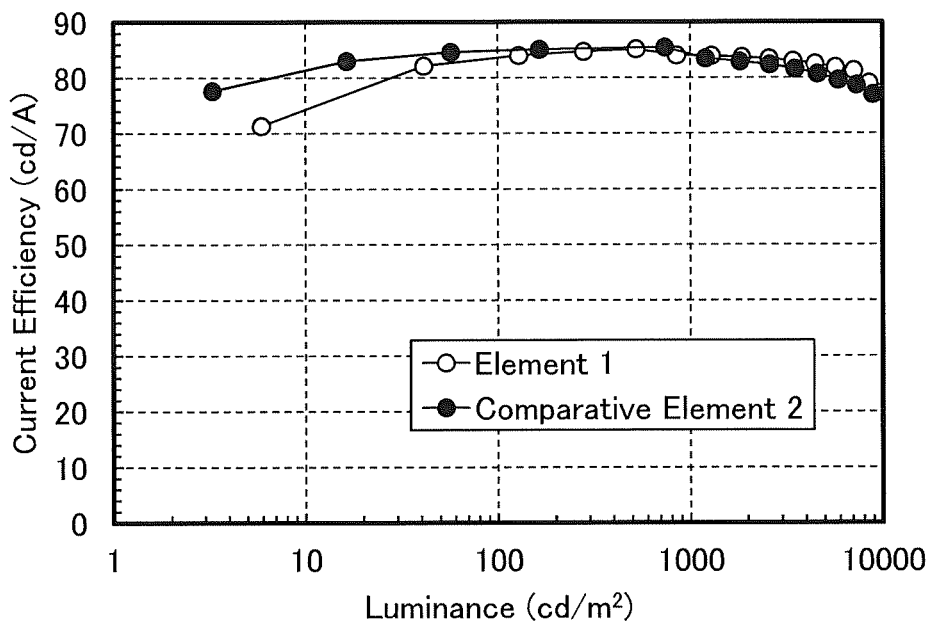
FIG. 25 shows luminance-current efficiency characteristics of the light-emitting element 1 and the comparative light-emitting element 2.
Figure 26:
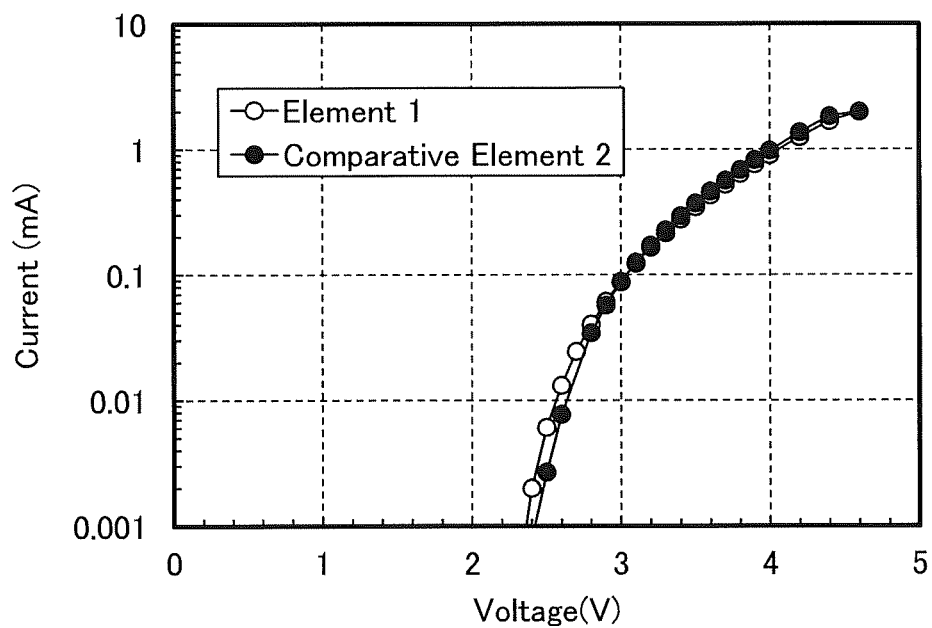
FIG. 26 shows voltage-current characteristics of the light-emitting element 1 and the comparative light-emitting element 2.

In this example, element structures, fabrication methods, and properties of a light-emitting element 1 (a light-emitting element of one embodiment of the present invention) in which mBnfBPTzn (Structural Formula (100)) described in Example 1 is used in a light-emitting layer and a comparative light-emitting element 2 in which the comparative organic compound 2-{3-[3-(dibenzothiophen-4-yl)phenyl]phenyl}-4,6-diphenyl-1,3,5-triazine (abbreviation: mDBtBPTzn) (Structural Formula (200)) is used in a light-emitting layer will be described. Note that FIG. 22 illustrates an element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transpor layer | | Electron-injection layer | Second electrode |
|---|---|---|---|---|---|---|---|---|
| Light-emitting element 1 | ITSO (70 nm) | DBT3P-II:MoOx (4:2, 60 nm) | BPAFLP (20 nm) | * | mBnfBPTzn (20 nm) | Bphen (10 nm) | LiF (1 nm) | Al (200 nm) |
| Comparative light-emitting element 2 | ITSO (70 nm) | DBT3P-II:MoOx (4:2, 60 nm) | BPAFLP (20 nm) | ** | mDBtBPTzn (20 nm) | Bphen (10 nm) | LiF (1 nm) | Al (200 nm) |

\* mBnfBPTzn:PCBBiF:[Ir(dppm)$_2$(acac)] (0.7:0.3:0.05 (20 nm)\0.8:0.2:0.05 (20 nm))
\*\* mDBtBPTzn:PCBBiF:[Ir(dppm)$_2$(acac)] (0.7:0.3:0.05 (20 nm)\0.8:0.2:0.05 (20 nm))

[Chemical Formula 34]
(100)
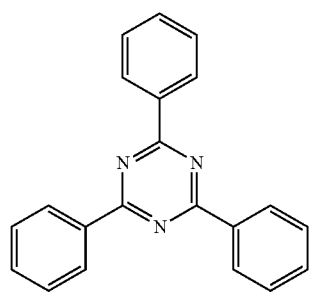
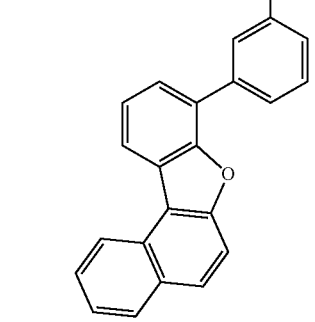
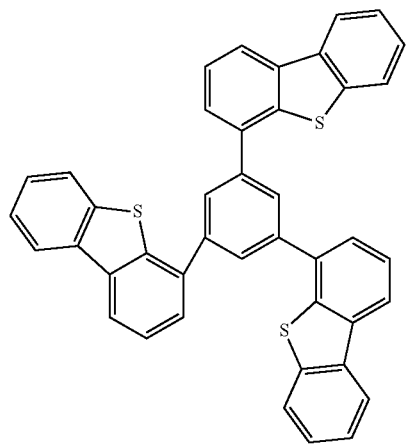
DBT3P-II
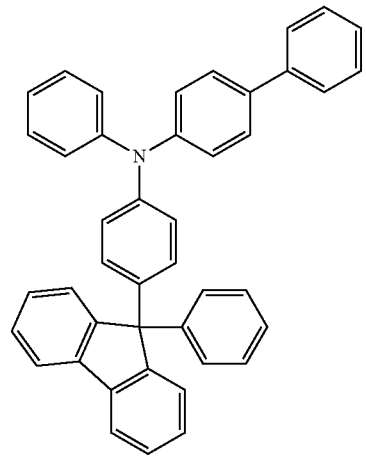
BPAFLP
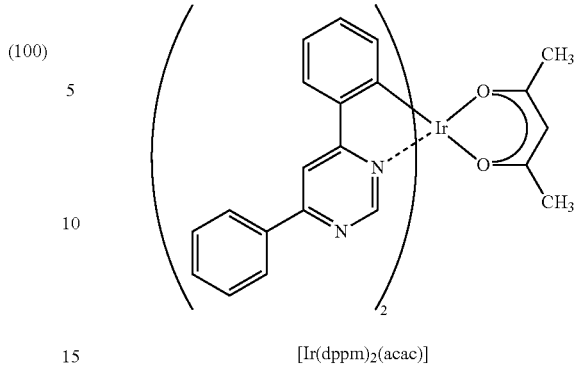
[Ir(dppm)₂(acac)]
(200)
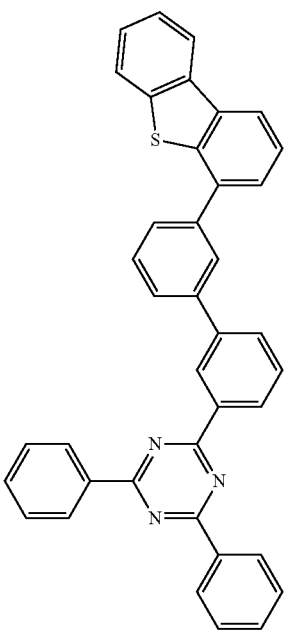
mDBtBPTzn
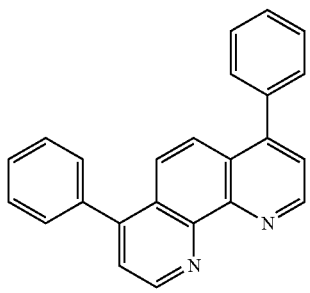
Bphen

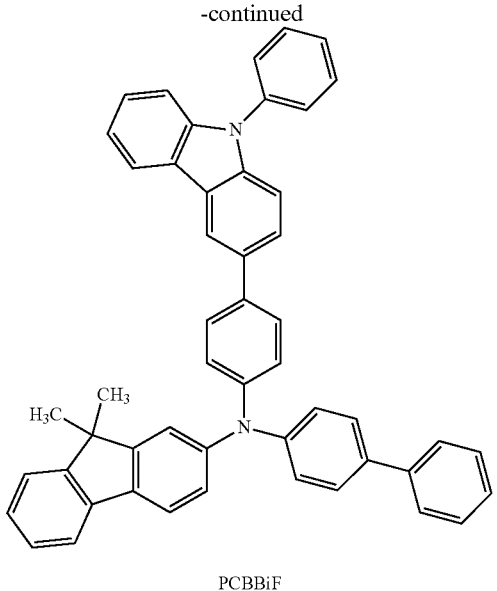

PCBBiF

<<Fabrication of Light-Emitting Elements>>

In each of the light-emitting elements described in this example, as illustrated in FIG. 22, a hole-injection layer 911, a hole-transport layer 912, a light-emitting layer 913, an electron-transport layer 914, and an electron-injection layer 915 were stacked in this order over a first electrode 901 formed over a substrate 900, and a second electrode 903 was stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately 10$^{-4}$ Pa, and was subjected to vacuum baking at 170° C. for 60 minutes in a heating chamber of the vacuum evaporation apparatus, and then the substrate was cooled down for about 30 minutes.

Next, the hole-injection layer 911 was formed over the first electrode 901. After the pressure in the vacuum evaporation apparatus was reduced to 10$^{-4}$ Pa, the hole-injection layer 911 was formed by co-evaporation to have a mass ratio of 1,3,5-tri(dibenzothiophen-4-yl)benzene (abbreviation: DBT3P-II) to molybdenum oxide of 4:2 and a thickness of 60 nm.

Then, the hole-transport layer 912 was formed over the hole-injection layer 911. The hole-transport layer 912 was formed to a thickness of 20 nm by evaporation of 4-phenyl-4'-(9-phenylfluoren-9-yl)triphenylamine (abbreviation: BPAFLP).

Next, the light-emitting layer 913 was formed over the hole-transport layer 912.

The light-emitting layer 913 in the light-emitting element 1 was formed by co-evaporation using mBnfBPTzn as a host material, using PCBBiF as an assist material, and using [Ir(dppm)$_2$(acac)] as a guest material (phosphorescent material) to have a weight ratio of mBnfBPTzn to PCBBiF and [Ir(dppm)$_2$(acac)] of 0.7:0.3:0.05. The thickness was set to 20 nm. Furthermore, mBnfBPTzn, PCBBiF, and [Ir(dppm)$_2$(acac)] were deposited by co-evaporation to have a mass ratio of mBnfBPTzn:PCBBiF:[Ir(dppm)$_2$(acac)] of 0.8:0.2:0.05. The thickness was set to 20 nm. Accordingly, the light-emitting layer 913 had a stacked-layer structure with a thickness of 40 nm.

The light-emitting layer 913 in the comparative light-emitting element 2 was formed by co-evaporation using mDBtBPTzn as a host material, using PCBBiF as an assist material, and using [Ir(dppm)$_2$(acac)] as a guest material (phosphorescent material) to have a weight ratio of mDBtBPTzn to PCBBiF and [Ir(dppm)$_2$(acac)] of 0.7:0.3:0.05. The thickness was set to 20 nm. Furthermore, mDBtBPTzn, PCBBiF, and [Ir(dppm)$_2$(acac)] were deposited by co-evaporation to have a mass ratio of mDBtBPTzn:PCBBiF:[Ir(dppm)$_2$(acac)] of 0.8:0.2:0.05. The thickness was set to 20 nm. Accordingly, the light-emitting layer 913 had a stacked-layer structure with a thickness of 40 nm.

Next, the electron-transport layer 914 was formed over the light-emitting layer 913. The electron-transport layer 914 in the light-emitting element 1 was formed in the following manner: mBnfBPTzn and bathophenanthroline (abbreviation: Bphen) were sequentially deposited by evaporation to thicknesses of 20 nm and 10 nm, respectively. The electron-transport layer 914 in the comparative light-emitting element 2 was formed in the following manner: mDBtBPTzn and bathophenanthroline (abbreviation: Bphen) were sequentially deposited by evaporation to thicknesses of 20 nm and 10 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed using aluminum to a thickness of 200 nm by an evaporation method. In this example, the second electrode 903 functioned as a cathode.

Through the above steps, the light-emitting elements in each of which the EL layer was provided between a pair of electrodes over the substrate 900 were fabricated. The hole-injection layer 911, the hole-transport layer 912, the light-emitting layer 913, the electron-transport layer 914, and the electron-injection layer 915 described above were functional layers forming the EL layer of one embodiment of the present invention. Furthermore, in all the evaporation steps in the above fabrication method, evaporation was performed by a resistance-heating method.

Each of the light-emitting elements fabricated as described above was sealed using another substrate (not illustrated) in such a manner that the substrate (not illustrated) was fixed to the substrate 900 with a sealing material in a glove box containing a nitrogen atmosphere, a sealant was applied so as to surround the light-emitting element formed over the substrate 900, and then irradiation with 365-nm ultraviolet light at 6 J/cm$^2$ was performed and heat treatment was performed at 80° C. for 1 hour.

<<Operation Characteristics of Light-Emitting Elements>>

Operation characteristics of the fabricated light-emitting elements were measured. Note that the measurement was performed at room temperature (in an atmosphere kept at 25° C.). The results are shown in FIGS. 23 to 26.

Table 2 shows initial values of main characteristics of the light-emitting elements at around 1000 cd/m$^2$.

TABLE 2

|  | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 1 | 2.8 | 0.040 | 1.0 | (0.56, 0.44) | 850 | 84 | 94 | 32 |
| Comparative light-emitting element 2 | 2.9 | 0.058 | 1.4 | (0.56, 0.44) | 1200 | 84 | 90 | 32 |

The above results show that the light-emitting element 1 fabricated in this example has high current efficiency and high external quantum efficiency. Note that the comparative light-emitting element 2 exhibits comparably favorable characteristics. The results reveal that favorable element characteristics can be obtained in the case of having not only a structure common to mBnfBPTzn and mDBtBPTzn but also a structure in which two benzene rings are fused to a heteroaromatic ring.

Figure 27:
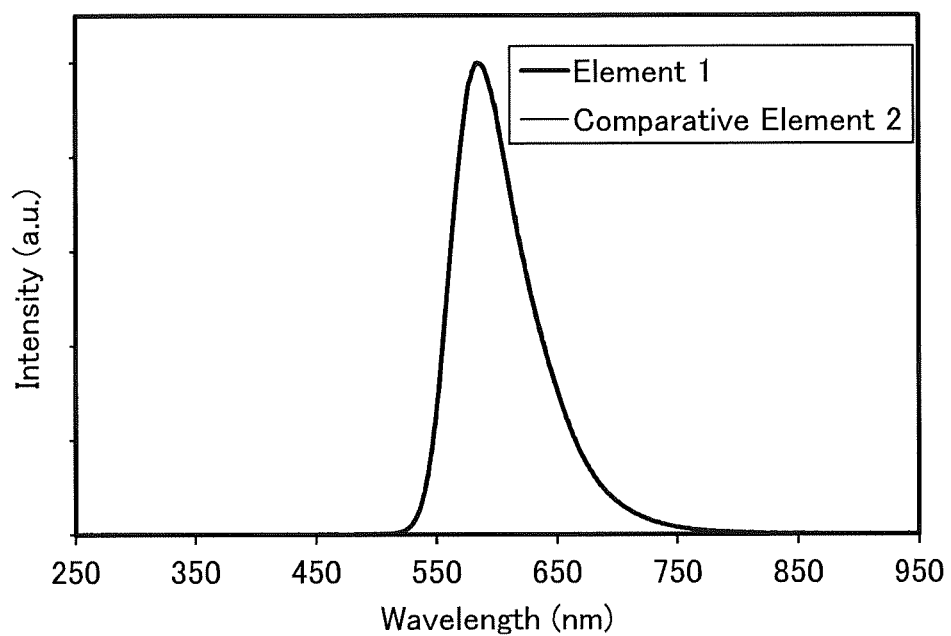
FIG. 27 shows emission spectra of the light-emitting element 1 and the comparative light-emitting element 2.

FIG. 27 shows emission spectra when current at a current density of 25 mA/cm² was applied to the light-emitting element 1 and the comparative light-emitting element 2. As shown in FIG. 27, the emission spectrum of each of the light-emitting element 1 and the comparative light-emitting element 2 has a peak at around 584 nm that is derived from light emission of the organometallic complex [Ir(dppm)₂(acac)] contained in the light-emitting layer 913.

Figure 28:
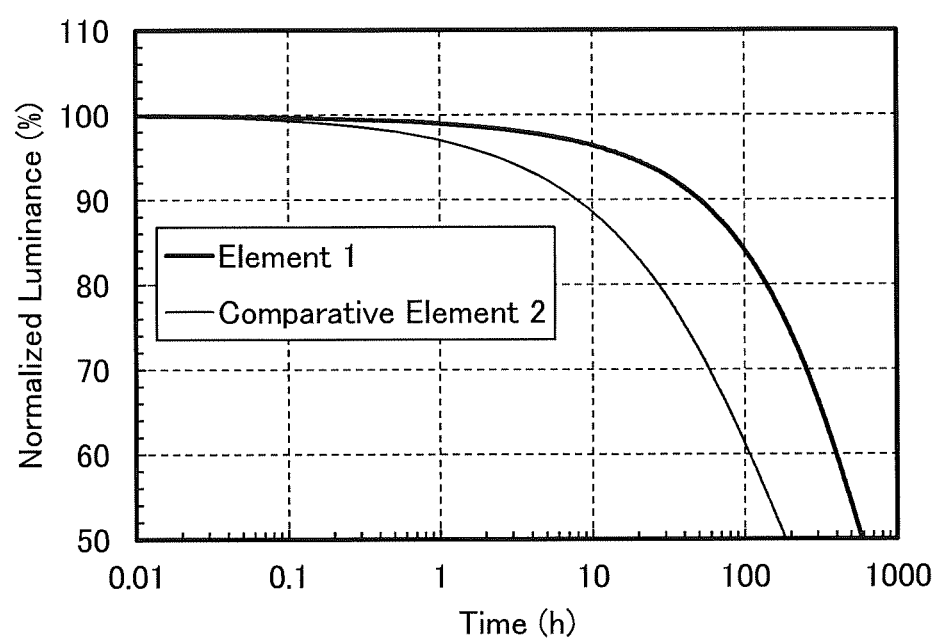
FIG. 28 shows reliability of the light-emitting element 1 and the comparative light-emitting element 2.
Figure 29:
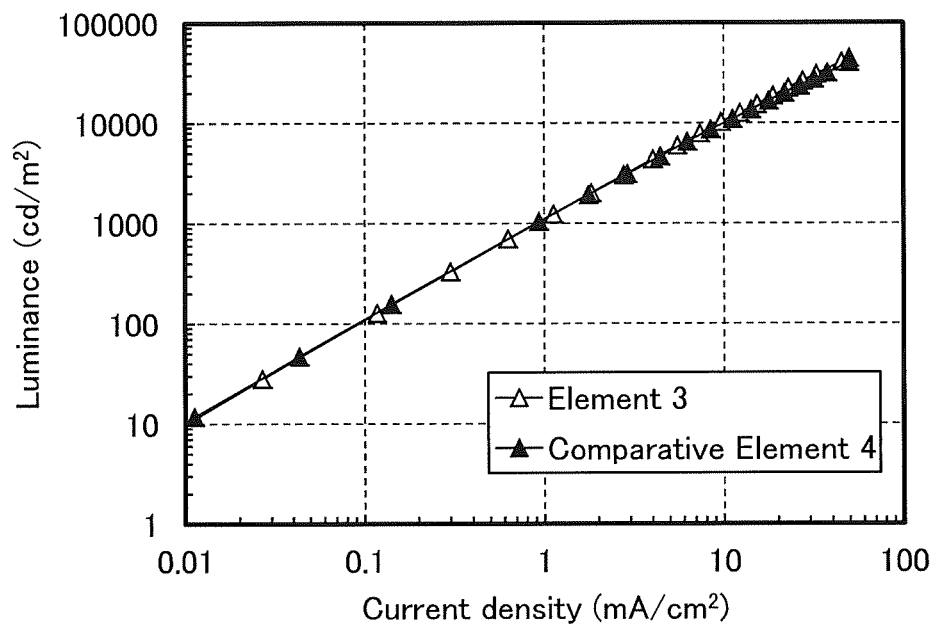
FIG. 29 shows current density-luminance characteristics of a light-emitting element 3 and a comparative light-emitting element 4.
Figure 30:
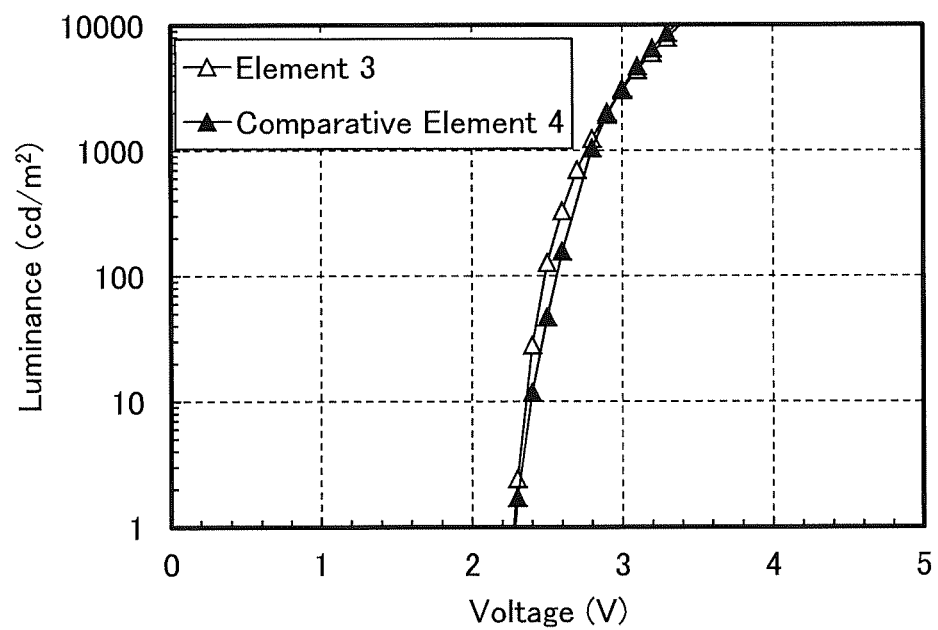
FIG. 30 shows voltage-luminance characteristics of the light-emitting element 3 and the comparative light-emitting element 4.
Figure 31:
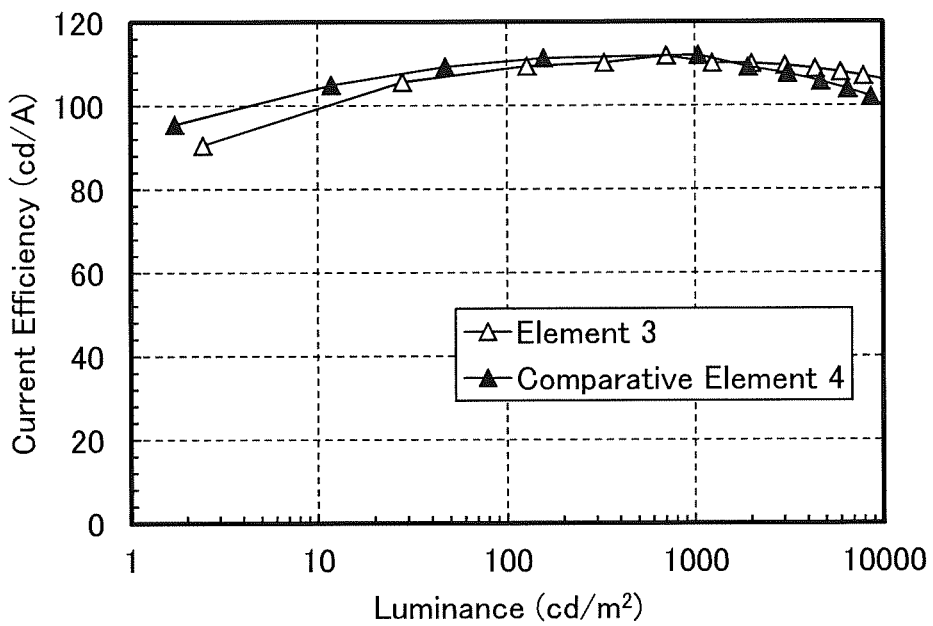
FIG. 31 shows luminance-current efficiency characteristics of the light-emitting element 3 and the comparative light-emitting element 4.
Figure 32:
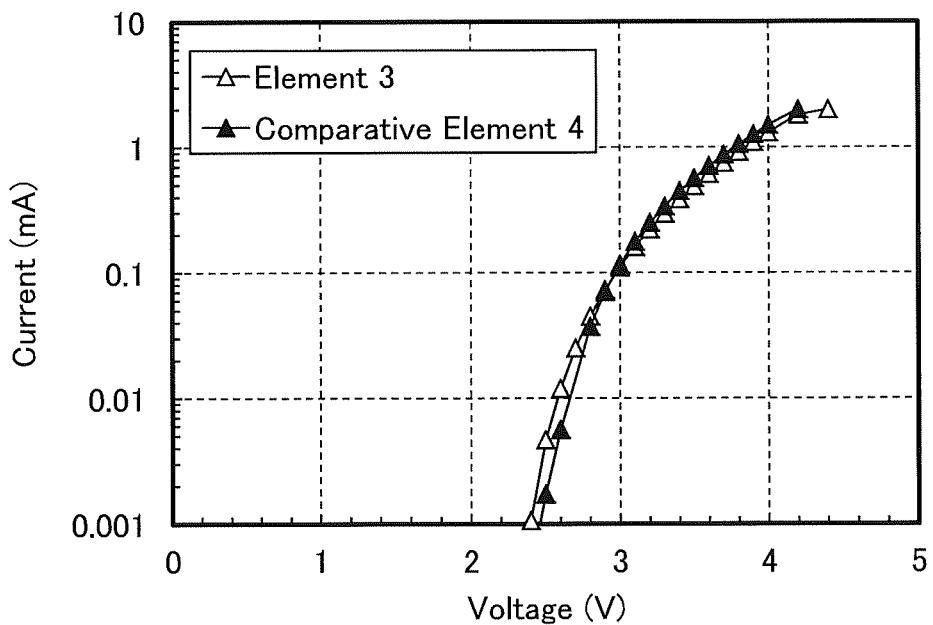
FIG. 32 shows voltage-current characteristics of the light-emitting element 3 and the comparative light-emitting element 4.

Next, reliability tests were performed on the light-emitting element 1 and the comparative light-emitting element 2. FIG. 28 shows results of the reliability tests. In FIG. 28, the vertical axis represents normalized luminance (%) with an initial luminance of 100%, and the horizontal axis represents driving time (h) of the elements. Note that in the reliability tests, the light-emitting elements were driven under the conditions where the initial luminance was set to 5000 cd/m² and the current density was constant.

These results reveal that the light-emitting element of one embodiment of the present invention (the light-emitting element 1) is comparable to the comparative light-emitting element 2 in current efficiency and external quantum efficiency, but is superior thereto in reliability.

As a result of a comparison between structures of mBnfBPTzn and mDBtBPTzn, it can be understood that the improvement in reliability of mBnfBPTzn is attributable to the benzonaphthofuran structure in which dibenzofuran (where two benzene rings are fused to a heteroaromatic ring) is further fused.

Example 4

In this example, element structures, fabrication methods, and properties of a light-emitting element 3 (a light-emitting element of one embodiment of the present invention) in which mBnfBPTzn (Structural Formula (100)) described in Example 1 is used in a light-emitting layer and a comparative light-emitting element 4 in which the comparative organic compound mDBtBPTzn (Structural Formula (200)) is used in a light-emitting layer will be described. Note that the light-emitting elements described in this example are similar to those described in Example 3 except for the light-emitting substance (dopant) used in the light-emitting layers; thus, FIG. 22 can be referred to, and the fabrication method is not described. Table 3 shows the specific structures of the light-emitting element 3 and the comparative light-emitting element 4 described in this example. Chemical formulae of materials used in this example are shown below.

TABLE 3

|  | First electrode | Hole-injection layer | Hole-transport layer | Light-emitting layer | Electron-transpor layer | Electron-injection layer | Second electrode |
|---|---|---|---|---|---|---|---|
| Light-emitting element 3 | ITSO (70 nm) | DBT3P-II:MoOx (4:2, 60 nm) | BPAFLP (20 nm) | * | mBnfBPTzn (20 nm) | Bphen (10 nm) | LiF (1 nm) | Al (200 nm) |
| Comparative light-emitting element 4 | ITSO (70 nm) | DBT3P-II:MoOx (4:2, 60 nm) | BPAFLP (20 nm) | ** | mDBtBPTzn (20 nm) | Bphen (10 nm) | LiF (1 nm) | Al (200 nm) |

* mBnfBPTzn:PCBBiF:[Ir(tBuppm)₂(acac)] (0.7:0.3:0.05 (20 nm)\0.8:0.2:0.05 (20 nm))
** mDBtBPTzn:PCBBiF:[Ir(tBuppm)₂(acac)] (0.7:0.3:0.05 (20 nm)\0.8:0.2:0.05 (20 nm))

[Chemical Formula 35]

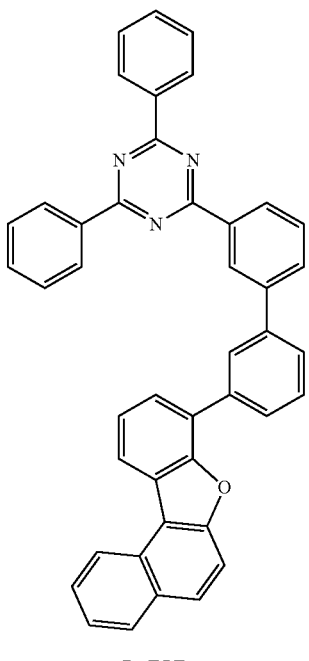

(100)

mBnfBPTzn

-continued
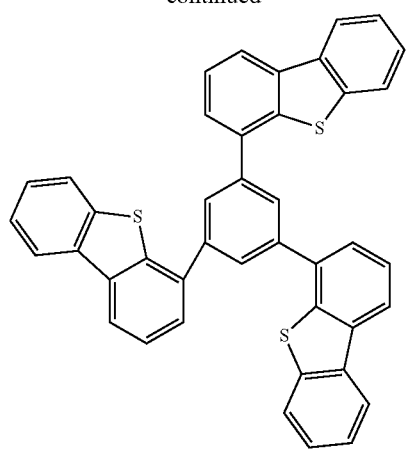
DBT3P-II
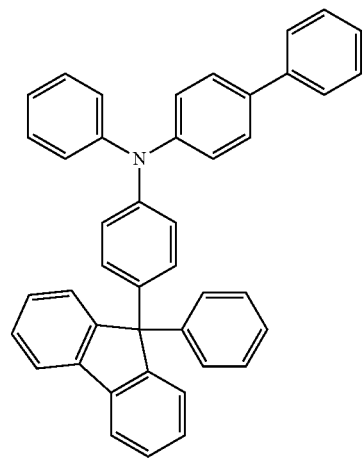
BPAFLP
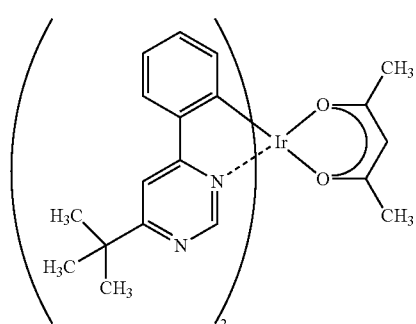
[Ir(tBuppm)₂(acac)]
-continued
(200)
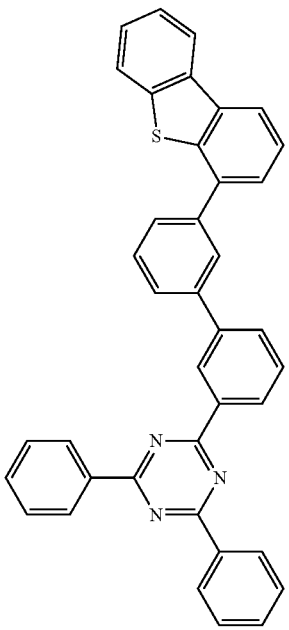
mDBtBPTzn
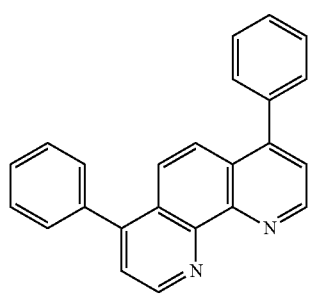
Bphen
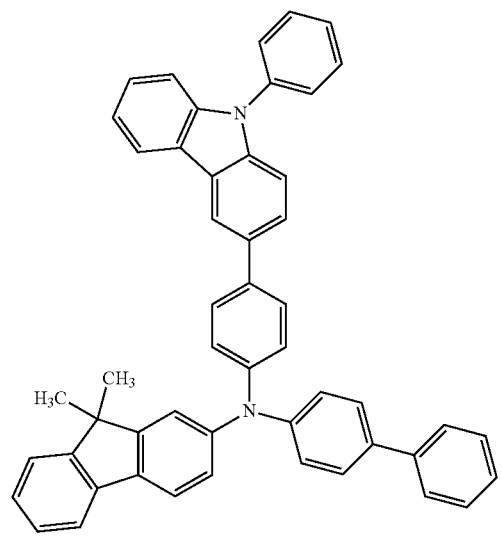
PCBBiF <<Operation Characteristics of Light-Emitting Elements>>

Operation characteristics of the fabricated light-emitting elements were measured. Note that the measurement was performed at room temperature (in an atmosphere kept at 25° C.). The results are shown in FIGS. 29 to 32.

Table 4 shows initial values of main characteristics of the light-emitting elements at around 1000 cd/m².

TABLE 4

|  | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
| --- | --- | --- | --- | --- | --- | --- | --- | --- |
| Light-emitting element 3 | 2.8 | 0.045 | 1.1 | (0.41, 0.58) | 1200 | 110 | 120 | 29 |
| Comparative light-emitting element 4 | 2.8 | 0.037 | 0.9 | (0.41, 0.58) | 1000 | 110 | 130 | 30 |

The above results show that the light-emitting element 3 fabricated in this example has high current efficiency and high external quantum efficiency. Note that the comparative light-emitting element 4 exhibits comparably favorable characteristics. The results reveal that favorable element characteristics can be obtained in the case of having not only a structure common to mBnfBPTzn and mDBtBPTzn but also a structure in which two benzene rings are fused to a heteroaromatic ring (dibenzofuran or dibenzothiophene).

Figure 33:
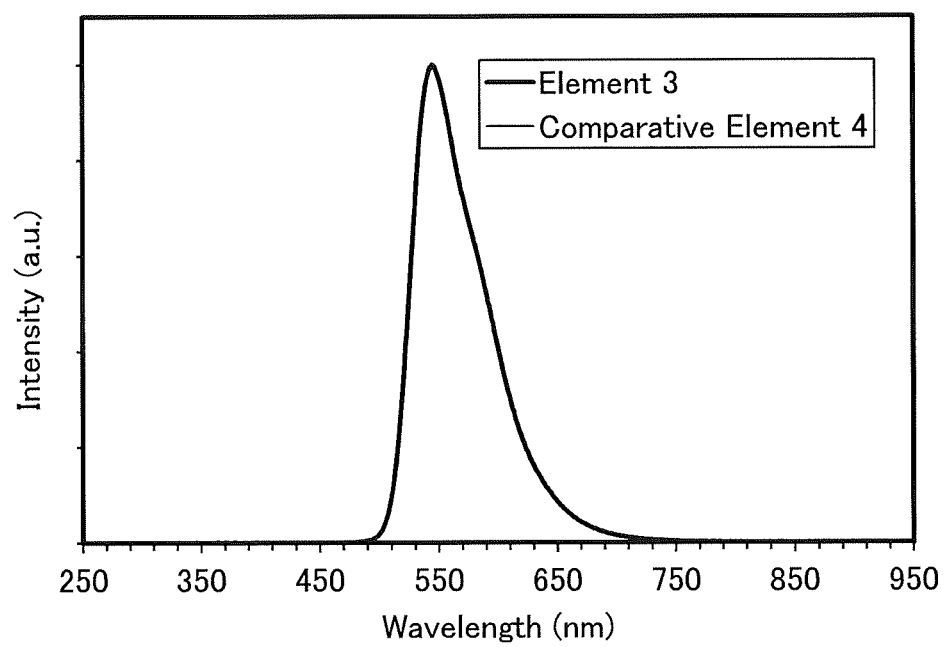
FIG. 33 shows emission spectra of the light-emitting element 3 and the comparative light-emitting element 4.

FIG. 33 shows emission spectra when current at a current density of 25 mA/cm² was applied to the light-emitting element 3 and the comparative light-emitting element 4. As shown in FIG. 33, the emission spectrum of each of the light-emitting element 3 and the comparative light-emitting element 4 has a peak at around 546 nm that is derived from light emission of the organometallic complex [Ir(tBuppm)$_2$(acac)] contained in the light-emitting layer 913.

Figure 34:
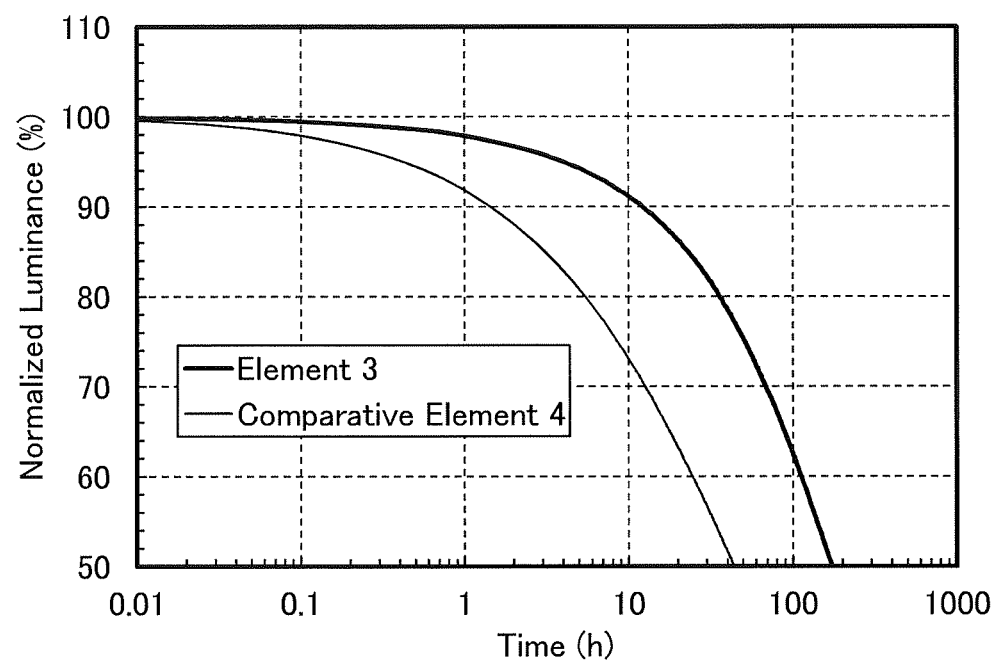
FIG. 34 shows reliability of the light-emitting element 3 and the comparative light-emitting element 4.

Next, reliability tests were performed on the light-emitting element 3 and the comparative light-emitting element 4. FIG. 34 shows results of the reliability tests. In FIG. 34, the vertical axis represents normalized luminance (%) with an initial luminance of 100%, and the horizontal axis represents driving time (h) of the elements. Note that in the reliability tests, the light-emitting elements were driven under the conditions where the initial luminance was set to 5000 cd/m² and the current density was constant.

These results reveal that the light-emitting element of one embodiment of the present invention (the light-emitting element 3) is comparable to the comparative light-emitting element 4 in current efficiency and external quantum efficiency, but is superior thereto in reliability.

As a result of a comparison between structures of mBnfBPTzn and mDBtBPTzn, it can be understood that the improvement in reliability of mBnfBPTzn is attributable to the benzonaphthofuran structure in which dibenzofuran (where two benzene rings are fused to a heteroaromatic ring) is further fused.

This application is based on Japanese Patent Application Serial No. 2016-202251 filed with Japan Patent Office on Oct. 14, 2016, the entire contents of which are hereby incorporated by reference.

What is claimed is:

1. An organic compound represented by General Formula (G1):

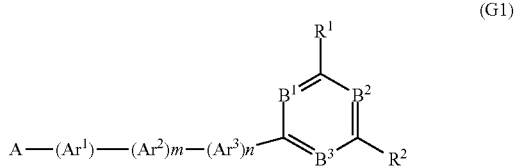

(G1)

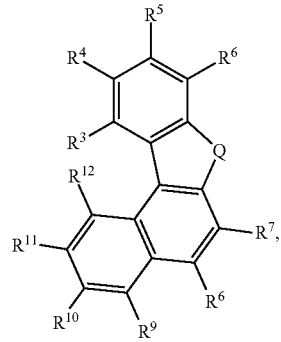

(G1-1)

where Ar¹ represents a substituted or unsubstituted phenylene group, wherein Ar² and Ar³ represent a substituted or unsubstituted meta phenylene group, where each of m and n is independently 0 or 1; when n or m is 0 the corresponding Ar2 or Ar3 is a single bond, wherein at least one of Ar2 or Ar3 is a substituted or unsubstituted meta phenylene group, where R¹ and R² separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group, where B¹ to B³ separately represent nitrogen or carbon, and at least one of B¹ to B³ represents nitrogen, where A is represented by General Formula (G1-1), where any one of R³ to R⁶ is bonded to Ar¹, and the others separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group, and where Q represents S or O.

2. The organic compound according to claim 1, wherein the organic compound is represented by General Formula (G2):

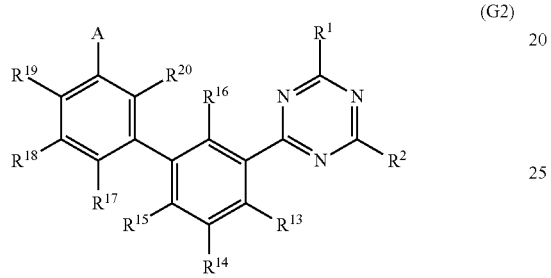

(G2)

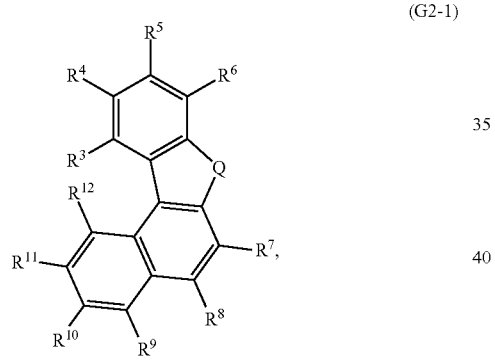

(G2-1)

where $R^{13}$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group, where A is represented by General Formula (G2-1), and wherein any one of $R^3$ to $R^6$ is bonded to A.

3. The organic compound according to claim 1, wherein the organic compound is represented by General Formula (G3):

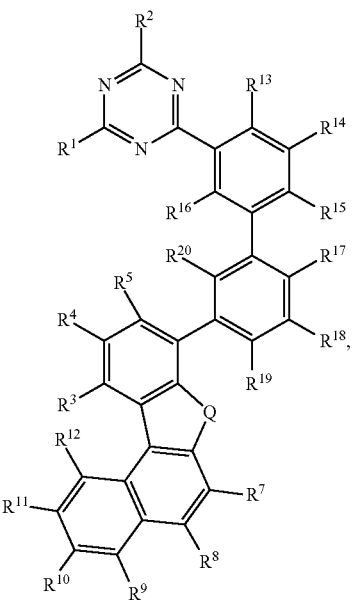

(G3)

where $R^{13}$ to $R^{20}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group.

4. The organic compound according to claim 1, wherein the organic compound is represented by General Formula (G5):

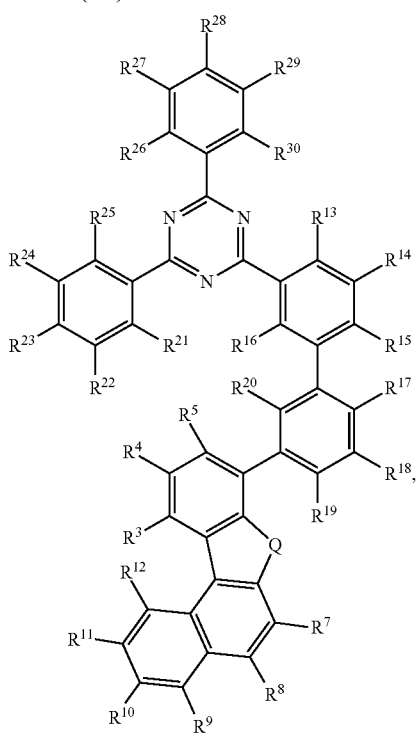

(G5)

where $R^{13}$ to $R^{30}$ separately represent hydrogen, an alkyl group having 1 to 6 carbon atoms, a substituted or unsubstituted phenyl group, a substituted or unsubstituted biphenyl group, a substituted or unsubstituted terphenyl group, a substituted or unsubstituted fluorenyl group, a substituted or unsubstituted methylfluorenyl group, a substituted or unsubstituted dimethylfluorenyl group, a substituted or unsubstituted spirofluorenyl group, a substituted or unsubstituted naphthyl group, or a substituted or unsubstituted phenanthrenyl group.

5. The organic compound according to claim 1, wherein the organic compound is represented by Structural Founula (100):

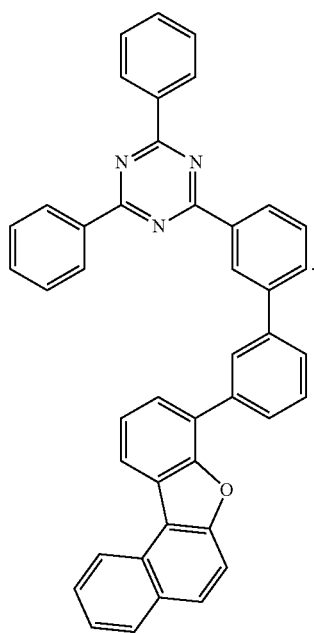

(100)

6. A light-emitting element comprising the organic compound according to claim 1.

7. A light-emitting element comprising an electroluminescent layer between a pair of electrodes, wherein the electroluminescent layer comprises the organic compound according to claim 1.

8. A light-emitting element comprising an electroluminescent layer between a pair of electrodes, wherein the electroluminescent layer comprises a light-emitting layer, and wherein the light-emitting layer comprises the organic compound according to claim 1.

9. A light-emitting device comprising:

the light-emitting element according to claim 8; and a transistor or a substrate.

10. A lighting device comprising:

the light-emitting device according to claim 9; and a housing, a cover, or a support.

11. A light-emitting element comprising:

an organic compound comprising a benzonaphthofuran skeleton and a triazine skeleton; and a thermally activated delayed fluorescence material.

12. A light-emitting device comprising:

the light-emitting element according to claim 11; and a transistor or a substrate.

* * * * *